US006345528B2

(12) United States Patent
Petro et al.

(10) Patent No.: US 6,345,528 B2
(45) Date of Patent: Feb. 12, 2002

(54) HIGH-TEMPERATURE CHARACTERIZATION OF POLYMERS WITH HPLC SYSTEM HAVING MULTIPLE MOBILE-PHASE RESERVOIRS

(75) Inventors: Miroslav Petro, Sunnyvale; Adam Safir, Oakland; Ralph B. Nielsen, San Jose; Eric D. Carlson, Palo Alto, all of CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/866,428

(22) Filed: May 24, 2001

Related U.S. Application Data

(62) Division of application No. 09/285,333, filed on Apr. 2, 1999, now Pat. No. 6,260,407
(60) Provisional application No. 60/080,652, filed on Apr. 3, 1998.

(51) Int. Cl.[7] .................. G01N 30/30; G01N 31/08; G01N 01/10; B01D 15/08
(52) U.S. Cl. .................. 73/61.52; 73/61.57; 73/61.56; 422/70; 210/663; 95/87
(58) Field of Search .................. 73/61.52, 61.55, 73/61.57, 61.56, 61.59, 23.26, 23.42; 422/70, 89; 95/84, 82, 87; 210/663, 656, 96.1, 93

(56) References Cited

U.S. PATENT DOCUMENTS

| | | | | |
|---|---|---|---|---|
| 4,239,623 A | * | 12/1980 | Schrenker | 210/96.1 |
| 4,271,703 A | | 6/1981 | Roof | 73/863.11 |
| 4,294,799 A | * | 10/1981 | Stephens et al. | 422/62 |
| 4,406,158 A | * | 9/1983 | Allington | 73/61.1 C |
| 4,534,941 A | | 8/1985 | Stephens et al. | 422/70 |
| 4,728,344 A | * | 3/1988 | Stacy | 55/67 |
| 4,775,476 A | * | 10/1988 | Melcher et al. | 210/635 |
| 4,798,081 A | | 1/1989 | Hazlitt et al. | 73/53 |
| 4,942,018 A | | 7/1990 | Munk | 422/70 |

(List continued on next page.)

FOREIGN PATENT DOCUMENTS

| | | |
|---|---|---|
| DE | 39 09 599 | 9/1990 |
| EP | 0 380 864 | 8/1990 |
| JP | 63-135857 | 6/1988 |
| JP | 1-98963 | 4/1989 |
| WO | WO98/10279 | 3/1998 |

OTHER PUBLICATIONS

Barth et al., 1998, Analytical Chemistry, 70 (12): 251–278 "Size Exclusion Chromatography and Related Separation Techniques".

Cools, P.J.C.H., et al., "Determination of the Chemical Composition Distribution of Copolymers of Styrene and Butadiene by Gradient Polymer Elution Chromatography," Journal of Chromatography, A, NL, Elsevier Science, vol. 736, No. 1, Jun. 7, 1996, pp. 125–130.

Fotheringham et al., 1998, American Laboratory: 25–32 "An integrated GPC–SEC system for room–temperature and high–temperature polymer characterization".

(List continued on next page.)

Primary Examiner—Hezron Williams
Assistant Examiner—David J. Wiggins

(57) ABSTRACT

Rapid characterization and screening of polymer samples to determine average molecular weight, molecular weight distribution and other properties is disclosed. Rapid flow characterization systems and methods, including liquid chromatography and flow-injection analysis systems and methods are preferably employed. High throughput, automated sampling systems and methods, high-temperature characterization systems and methods, and rapid, indirect calibration compositions and methods are also disclosed. The described methods, systems, and devices have primary applications in combinatorial polymer research and in industrial process control.

25 Claims, 25 Drawing Sheets

U.S. PATENT DOCUMENTS

| | | | | |
|---|---|---|---|---|
| 4,962,662 A | * | 10/1990 | Berger | 73/23.42 |
| 4,966,695 A | | 10/1990 | Joshua | 210/198.2 |
| 4,982,597 A | * | 1/1991 | Berger | 73/23.1 |
| 4,992,168 A | | 2/1991 | Takayama et al. | 210/198.2 |
| 5,008,204 A | | 4/1991 | Stehling | 436/85 |
| 5,238,653 A | * | 8/1993 | Bourne | 422/70 |
| 5,287,758 A | | 2/1994 | Geiss et al. | 73/864.01 |
| 5,290,520 A | * | 3/1994 | Maystre | 422/82.05 |
| 5,508,204 A | | 4/1996 | Norman | 436/161 |
| 5,597,733 A | | 1/1997 | Bell et al. | 436/54 |
| 5,738,783 A | | 4/1998 | Shirota et al. | 210/198.2 |
| 6,063,283 A | * | 5/2000 | Shirota et al. | 210/656 |

OTHER PUBLICATIONS

Petro et al., 1996, I.J. Chromotography A, 752: 59–66 Molded continuous poly (styrene–co–divinylbenzene) rod as a separation medium for the very fast separation of polymers Comparison of the chromatographic properties of the monolithic rod with columns packed with porous and non–porous beads in high–performance liquid chromatography of polystyrenes.

Petro et al., Analytical Chemistry, 1996, vol. 68: 315–321 Molded monolithic rod of macroporous Poly(styrene–co–divinylbenzene) as a Separation Medium for HPLC of Synthetic Polymers: "on–Column" Percipitation–Redissolution Chromatography as an Alternative to Size Exclusion Chromatography of Styrene Oligomers and Polymers.

Philipsen, H.J. et al., "Characterization of Low–Molar–Mass Polymers by Gradient Polymer Elution Chromatography I. Practical Parameters and Applications of The Analysis of Polyester Resins Under Reversed Phase Conditions," Journal of Chromatography A, NL, Elsevier Science, vol. 746, No. 2, Oct. 11, 1996, pp. 211–224.

Poche et al., 1997, J. Appl. Polym. Sci. 64(8): 1613–1623 "Use of Laboratory Robotics for Gel Permeation Chromatography Sample Preparation: Automation of High–Temperature Polymer Dissolution".

Staal, W.J., et al., "Monitoring of Orignated Polymer in Pure Monomer With Gradient Polymer Elution Chromatorgraphy (GPEC)," Journal of Liquid Chromatorgraphy, New York, NY US, vol. 17, No. 14/15, 1994, pp. 3191–3199.

* cited by examiner

FIG 1A
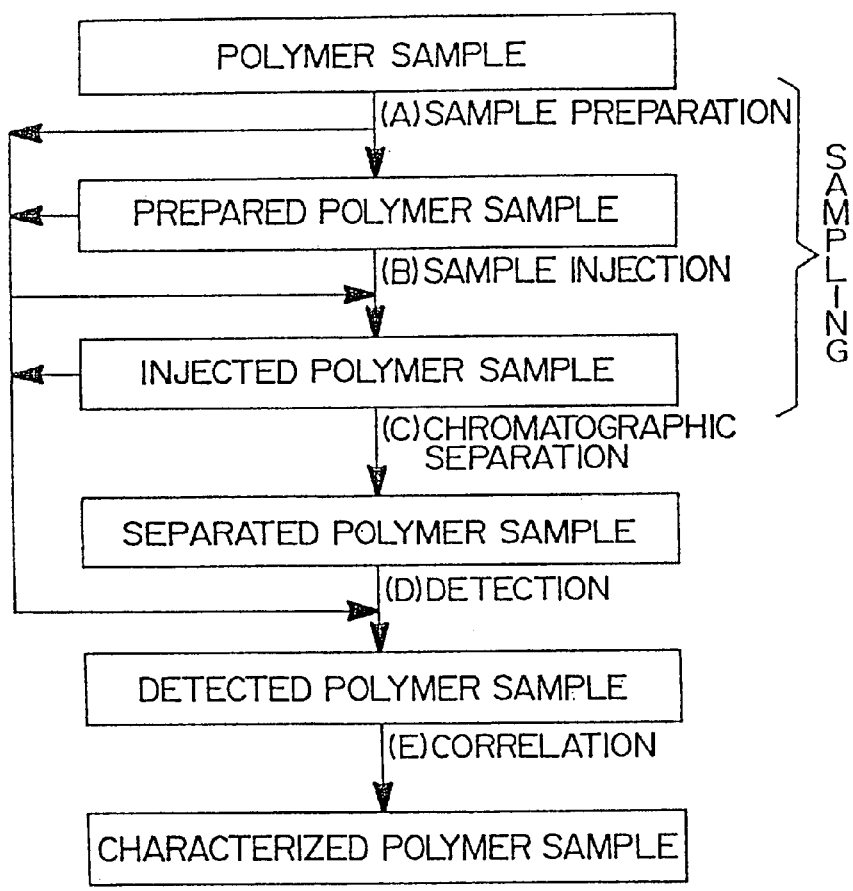
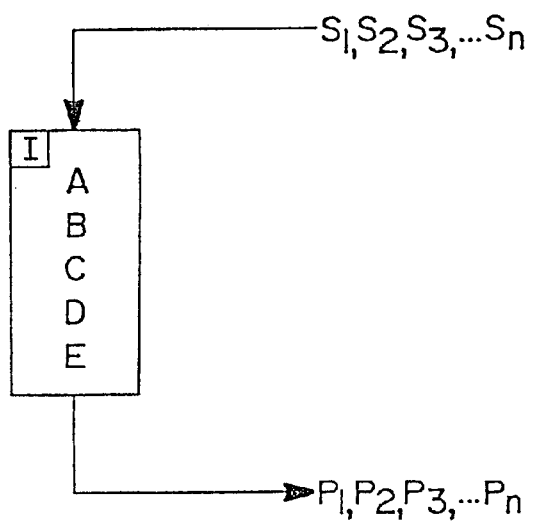
FIG 1B

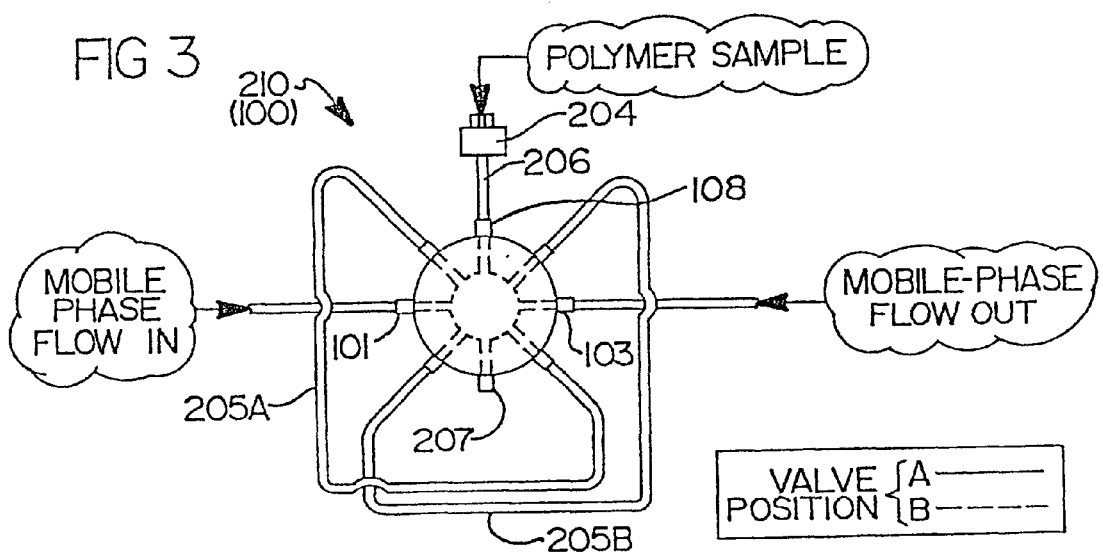
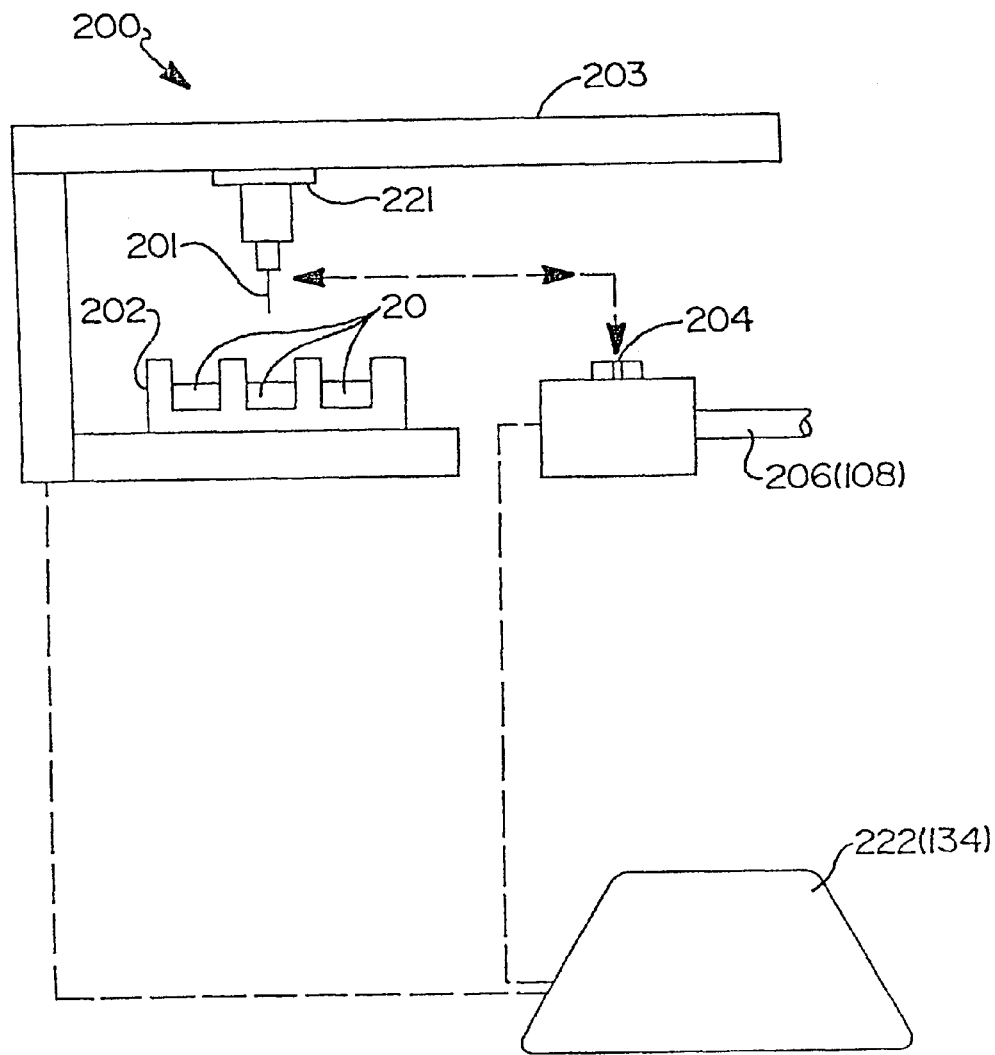

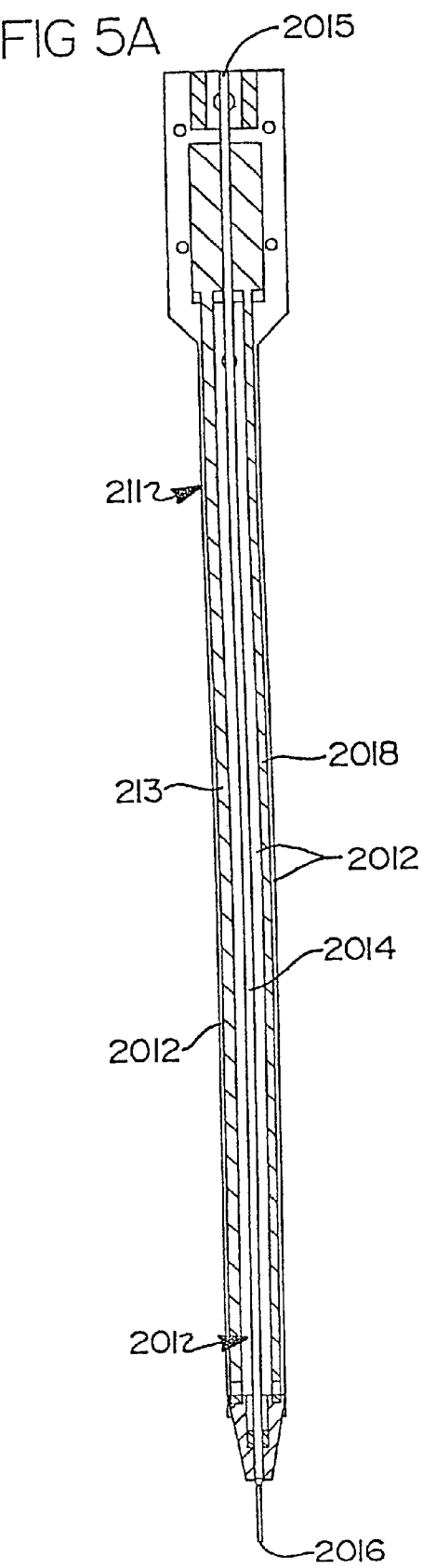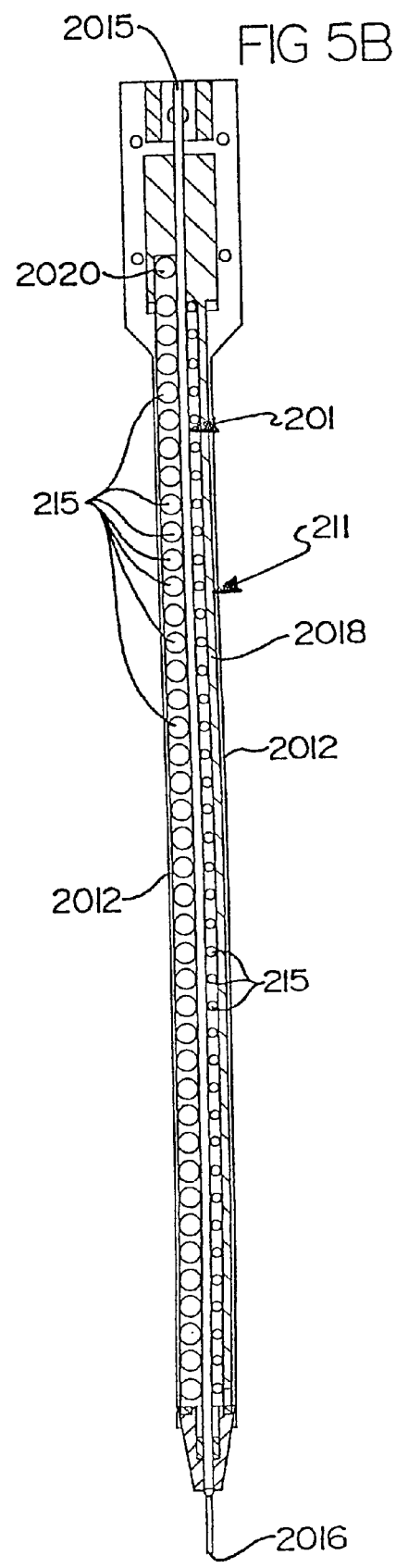

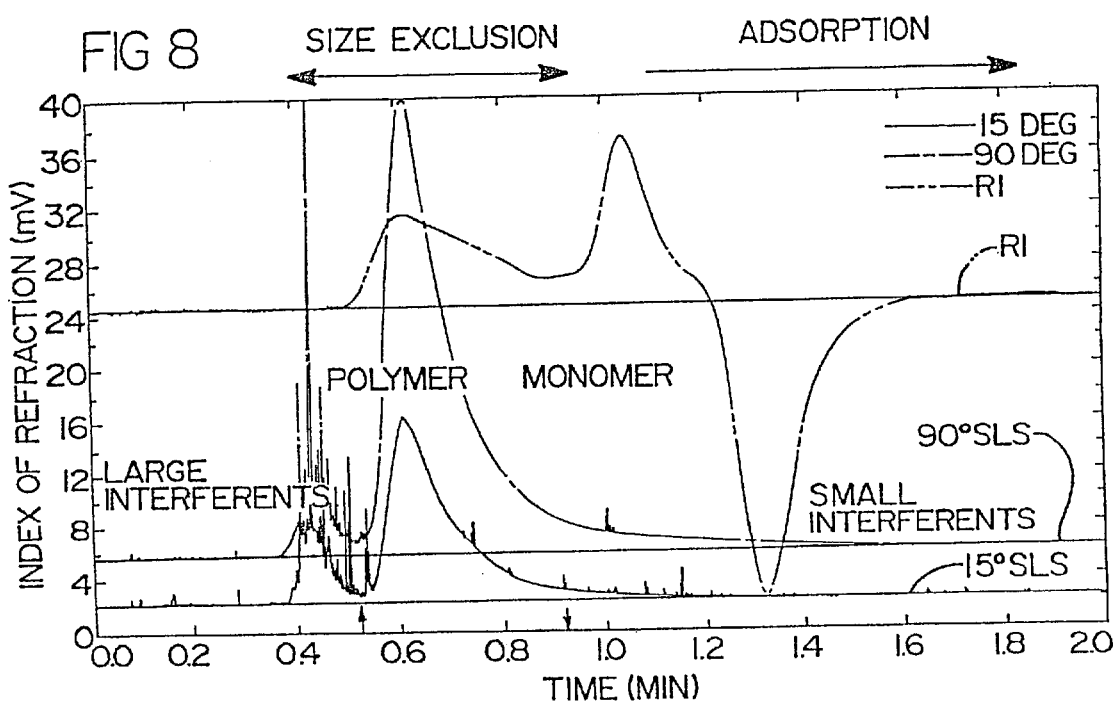
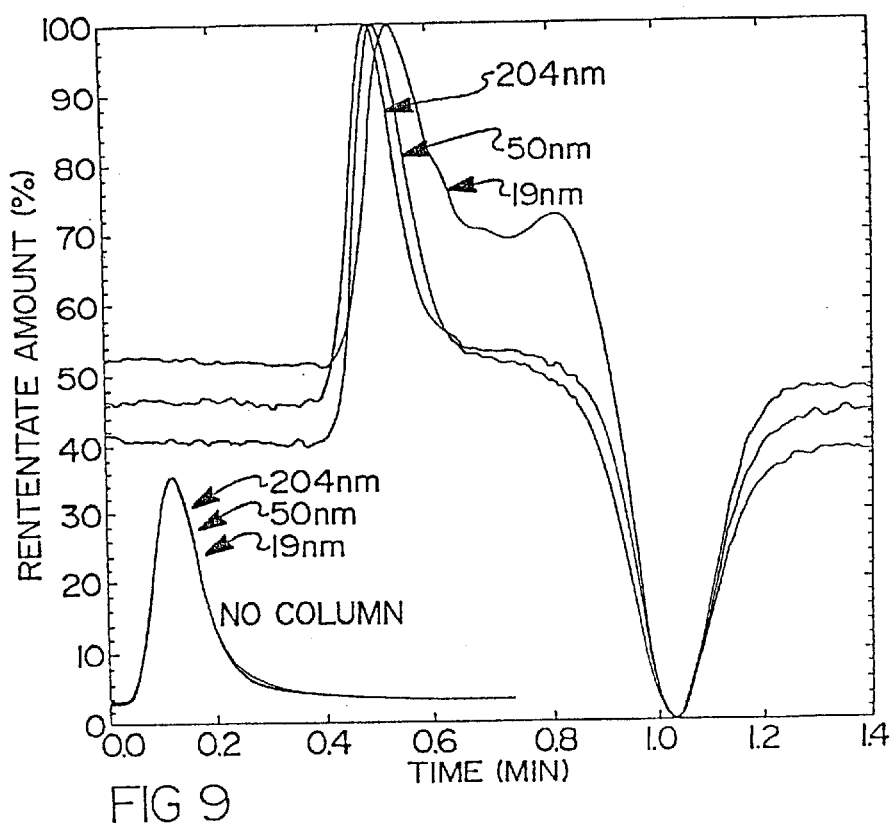

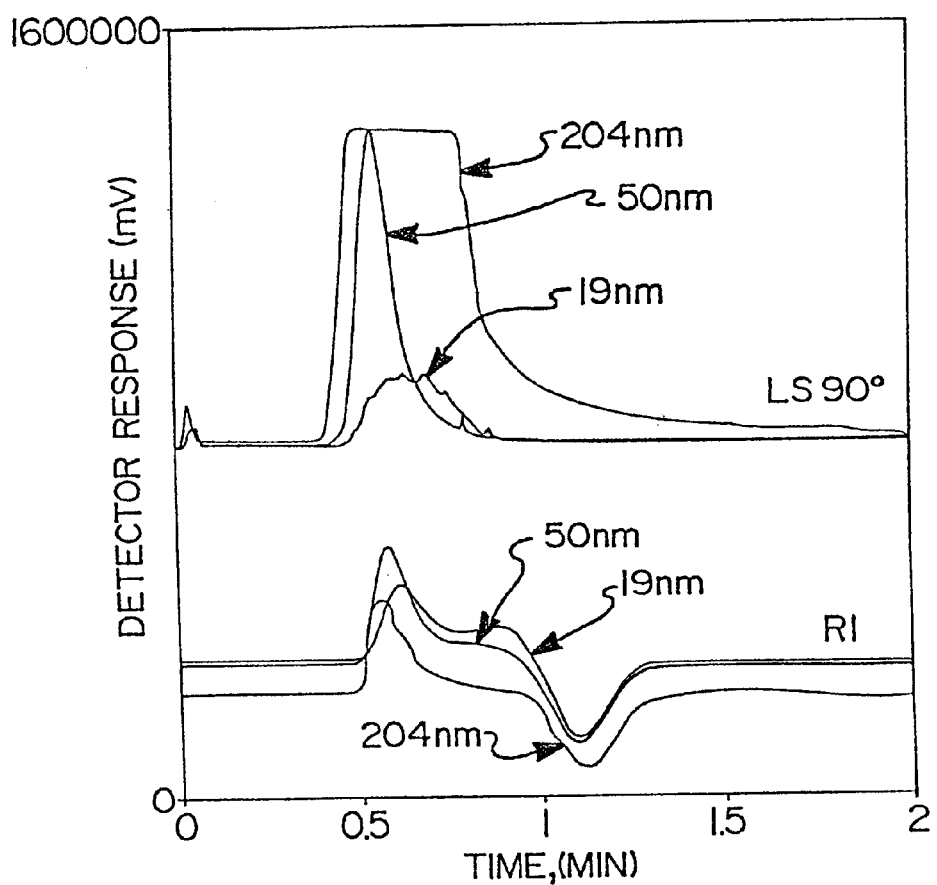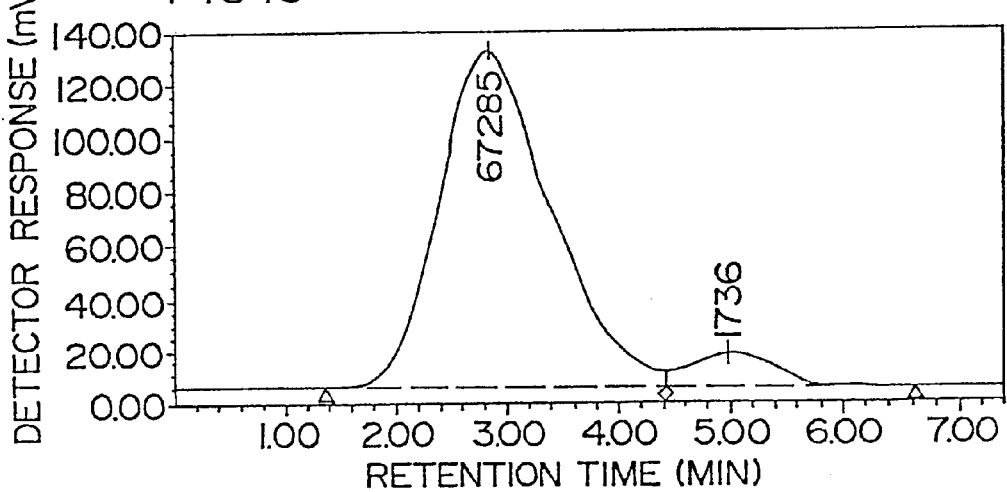

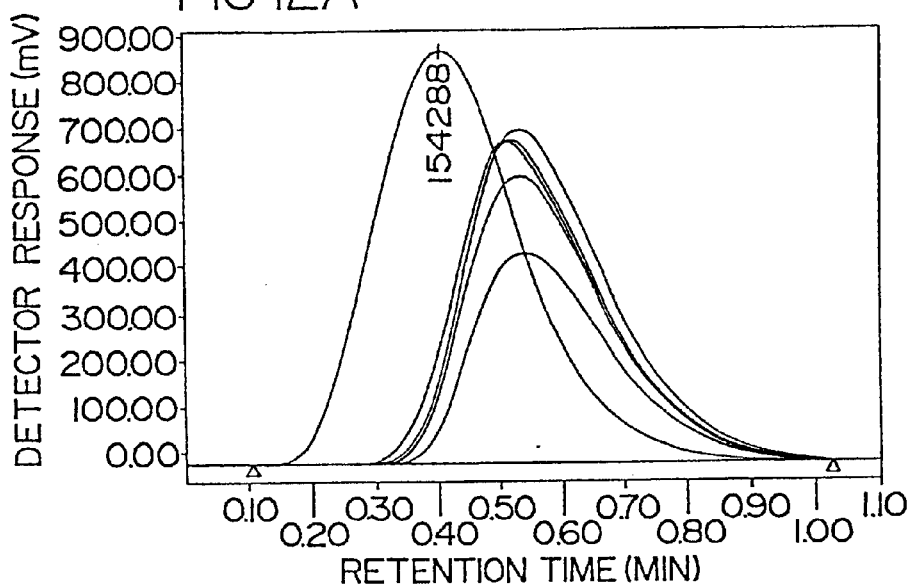
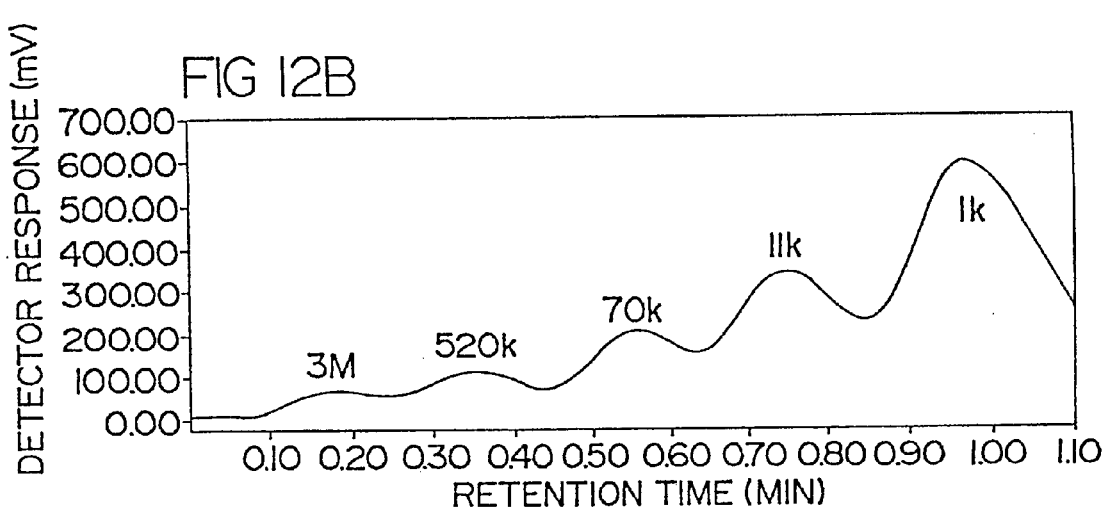
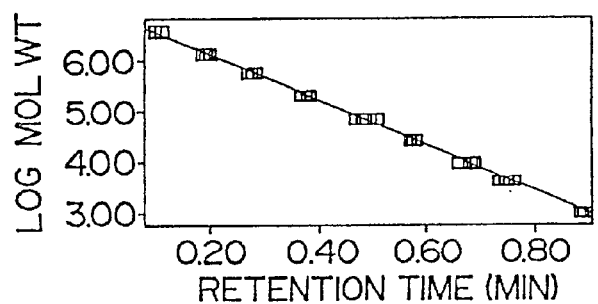

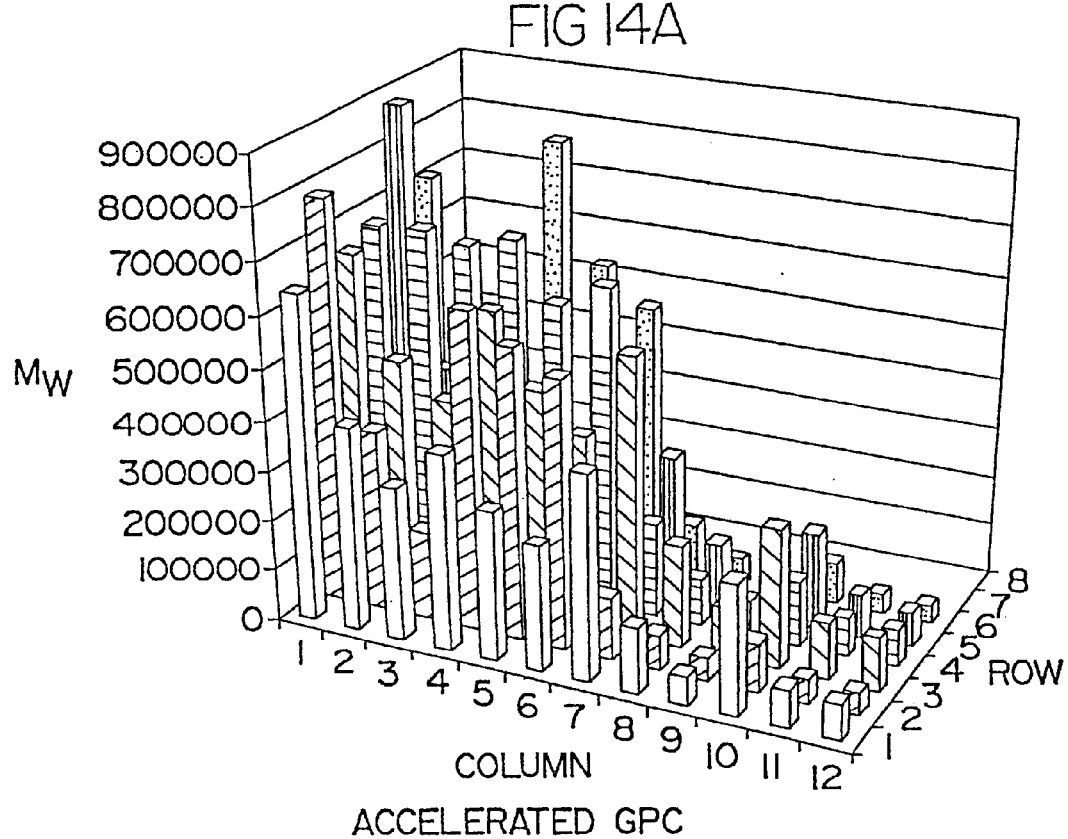
FIG 14A ACCELERATED GPC
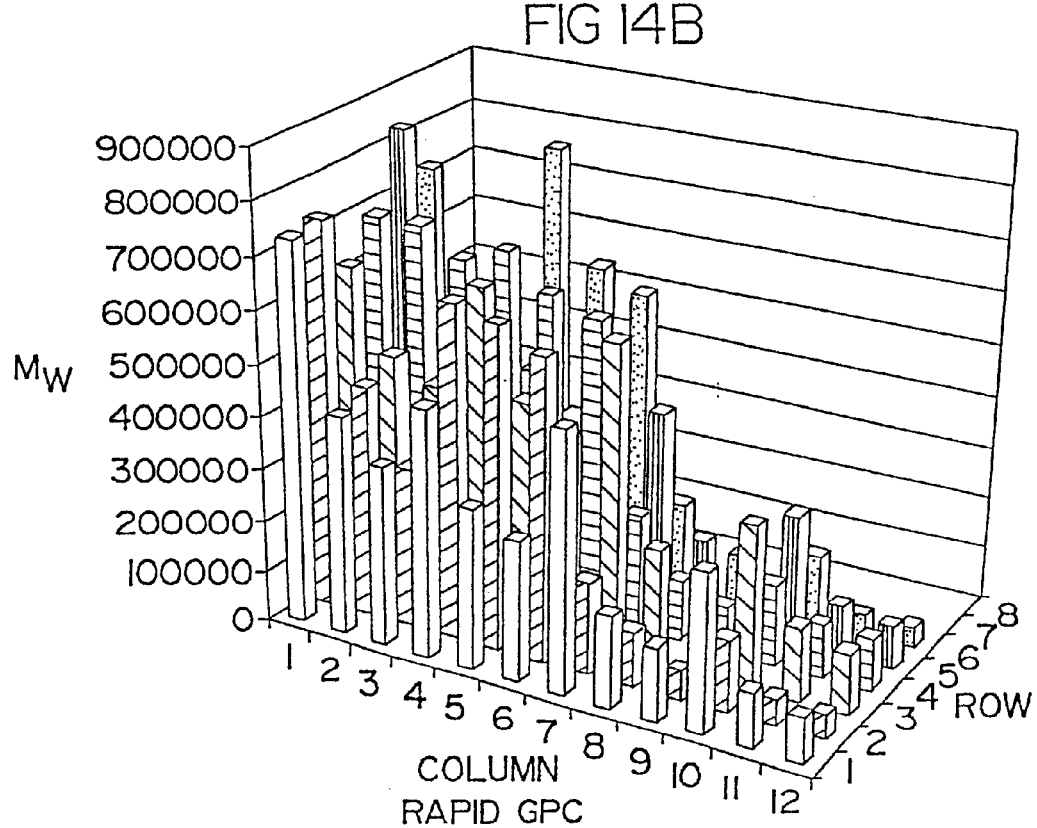
FIG 14B RAPID GPC

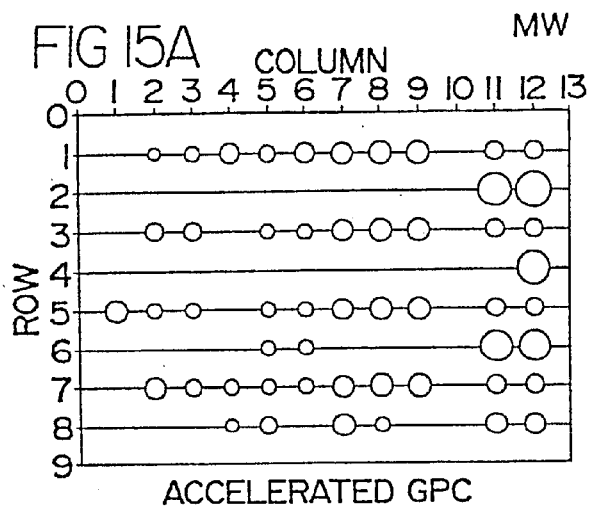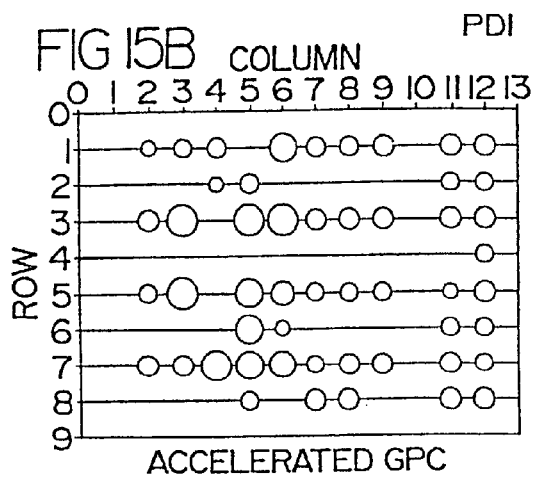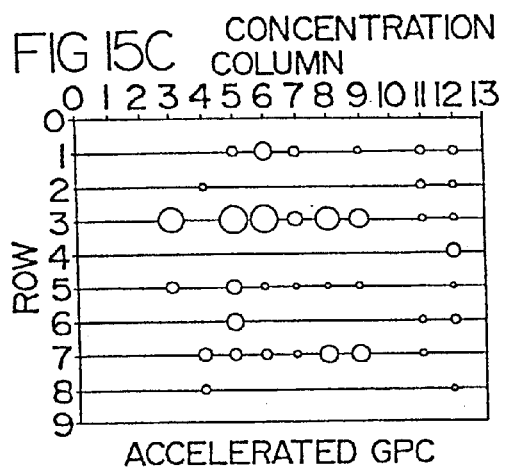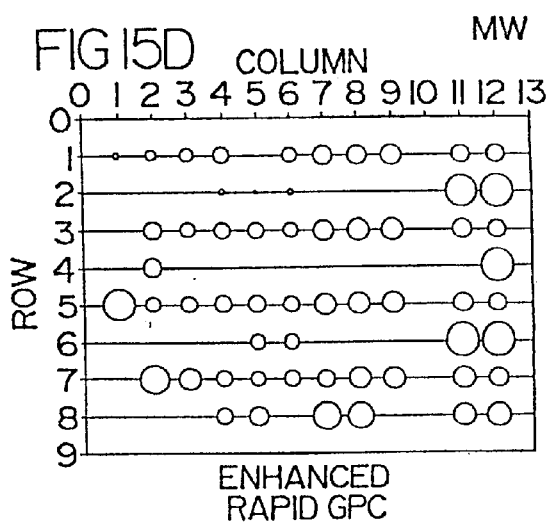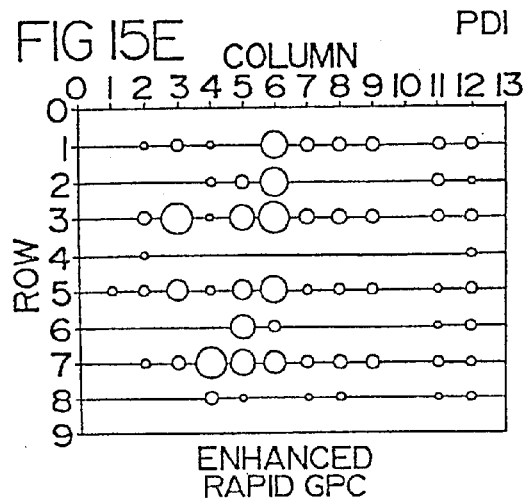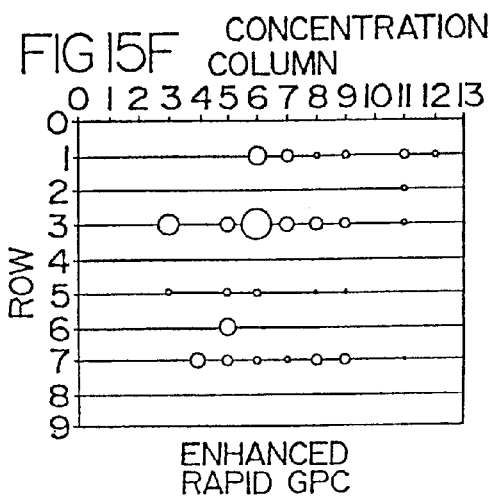

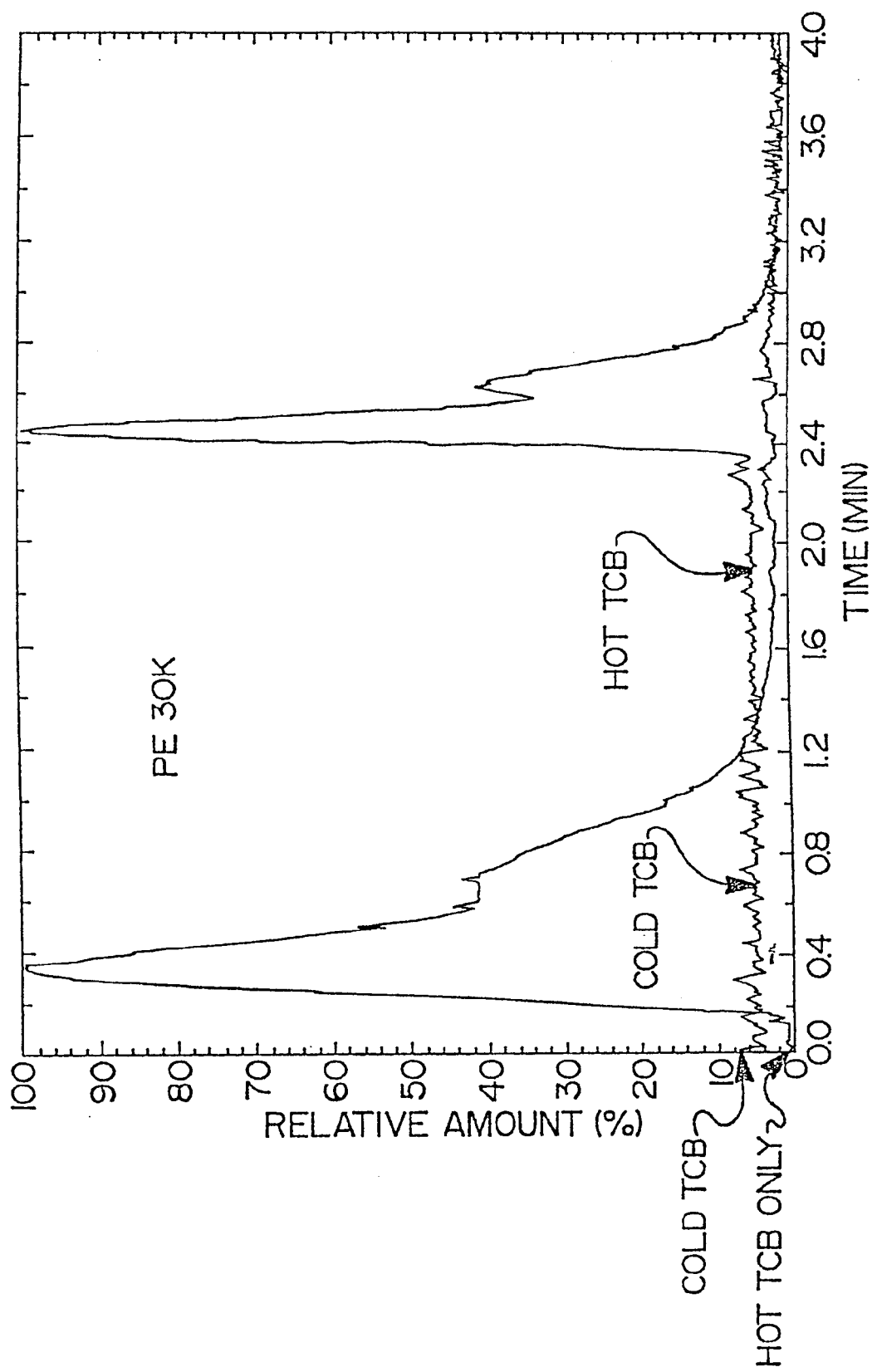

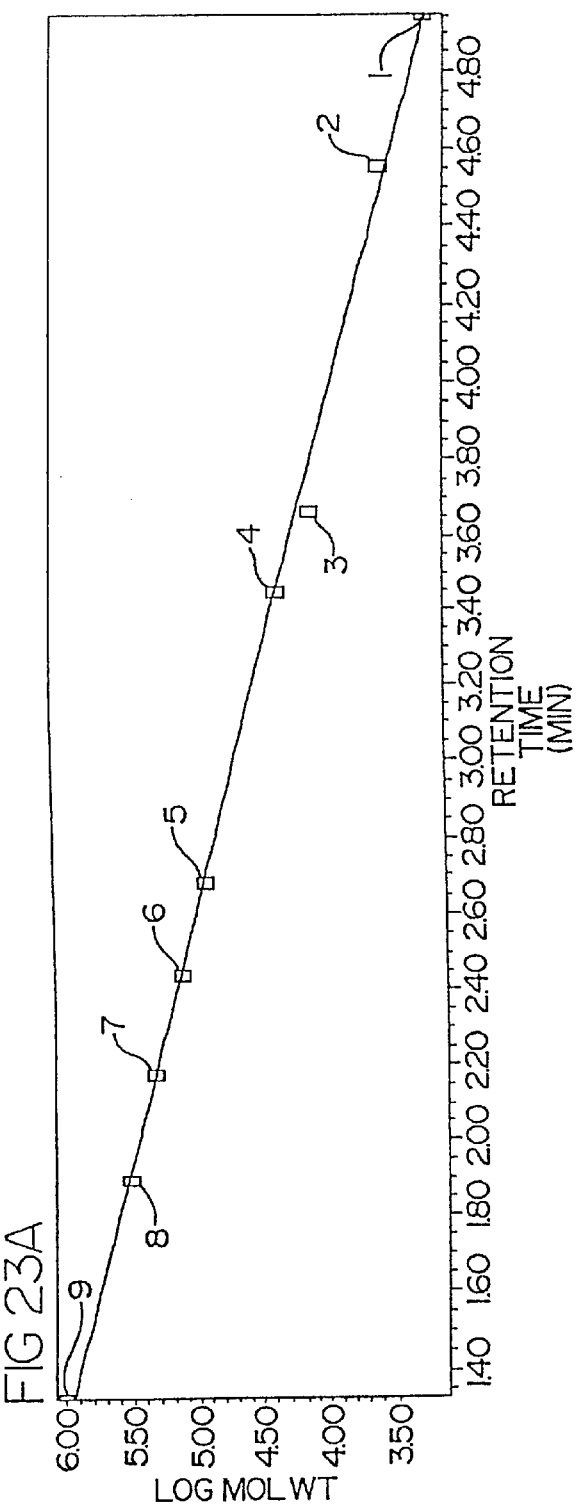
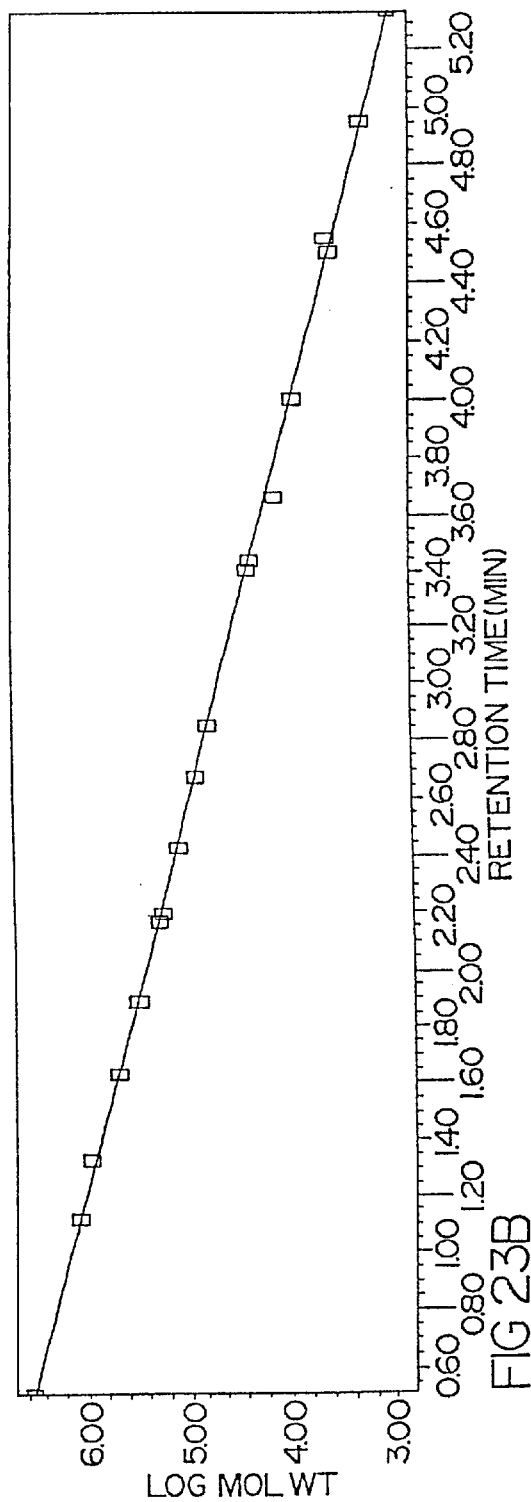
FIG 23A
FIG 23B

HIGH-TEMPERATURE CHARACTERIZATION OF POLYMERS WITH HPLC SYSTEM HAVING MULTIPLE MOBILE-PHASE RESERVOIRS

This application claims priority under 35 U.S.C. Sec. 119(e) to U.S. Provisional Application Ser. No. 60/080,652, filed Apr. 3, 1998 by Safir et al., which is hereby incorporated by reference for all purposes.

This application is a divisional application of U.S. patent application Ser. No. 09/285,333, dated Apr. 2, 1999 now issued as U.S. Pat. No. 6,260,407 to Petro et al. dated Jul. 17, 2001. This application is related to the following U.S. patent applications filed on the date even herewith, each of which is hereby incorporated by reference for all purposes: Ser. No. 09/285,393 entitled "Automated Sampling Methods for Rapid Characterization of Polymers", filed Apr. 2, 1999 by Petro et al.; Ser. No. 09/285,363 entitled "Rapid Characterization of Polymers", filed Apr. 2, 1999 by Safir et al.; Ser. No. 09/285,335 entitled "Flow-Injection Analysis and Variable-Flow Light Scattering Apparatus and Methods for Characterizing Polymers", filed Apr. 2, 1999 by Nielsen et al.; and Ser. No. 09/285,392 entitled "Indirect Calibration of Polymer Characterization Systems", filed Apr. 2, 1999 by Petro et al.

BACKGROUND OF INVENTION

The present invention generally relates to the field of polymer characterization. In particular, the invention relates to liquid chromatography and related flow-injection analysis techniques for rapidly characterizing polymer solutions, emulsions and dispersions, and to devices for implementing such techniques. In preferred embodiments, the characterization of a polymer sample or of components thereof is effected with optical detectors. The methods and devices disclosed herein are applicable, inter alia, to the rapid characterization of libraries of polymers prepared by combinatorial materials science techniques.

Currently, there is substantial research activity directed toward the discovery and optimization of polymeric materials for a wide range of applications. Although the chemistry of many polymers and polymerization reactions has been extensively studied, it is, nonetheless, rarely possible to predict a priori the physical or chemical properties a particular polymeric material will possess or the precise composition and architecture that will result from any particular synthesis scheme. Thus, characterization techniques to determine such properties are an essential part of the discovery process.

Combinatorial chemistry refers generally to methods for synthesizing a collection of chemically diverse materials and to methods for rapidly testing or screening this collection of materials for desirable performance characteristics and properties. Combinatorial chemistry approaches have greatly improved the efficiency of discovery of useful materials. For example, material scientists have developed and applied combinatorial chemistry approaches to discover a variety of novel materials, including for example, high temperature superconductors, magnetoresistors, phosphors and catalysts. See, for example, U.S. Pat. No. 5,776,359 to Schultz et al. In comparison to traditional materials science research, combinatorial materials research can effectively evaluate much larger numbers of diverse compounds in a much shorter period of time. Although such high-throughput synthesis and screening methodologies are conceptually promising, substantial technical challenges exist for application thereof to specific research and commercial goals.

Methods have been developed for the combinatorial (e.g., rapid-serial or parallel) synthesis and screening of libraries of small molecules of pharmaceutical interest, and of biological polymers such as polypeptides, proteins, oligonucleotides and deoxyribonucleic acid (DNA) polymers. However, there have been few reports of the application of combinatorial techniques to the field of polymer science for the discovery of new polymeric materials or polymerization catalysts or new synthesis or processing conditions. Brocchini et al. describe the preparation of a polymer library for selecting biomedical implant materials. See S. Brocchini et al., A Combinatorial Approach for Polymer Design, *J. Am. Chem. Soc.* 119, 4553–4554 (1997). However, Brocchini et al. reported that each synthesized candidate material was individually precipitated, purified, and then characterized according to "routine analysis" that included gel permeation chromatography to measure molecular weight and polydispersities. As such, Brocchini et al. did not address the need for efficient and rapid characterization of polymers.

Liquid chromatography is well known in the art for characterizing a polymer sample. Liquid chromatographic techniques employ separation of one or more components of a polymer sample from other components thereof by flow through a chromatographic column, followed by detection of the separated components with a flow-through detector. Approaches for liquid chromatography can vary, however, with respect to the basis of separation and with respect to the basis of detection. Gel permeation chromatography (GPC), a well-known form of size exclusion chromatography (SEC), is a frequently-employed chromatographic technique for polymer size determination. In GPC, the polymer sample is separated into components according to the hydrodynamic volume occupied by each component in solution. More specifically, a polymer sample is injected into a mobile phase of a liquid chromatography system and is passed through one or more chromatographic columns packed with porous beads. Molecules with relatively small hydrodynamic volumes diffuse into the pores of the beads and remain therein for longer periods, and therefore exit the column after molecules with relatively larger hydrodynamic volume. Hence, GPC can characterize one or more separated components of the polymer sample with respect to its effective hydrodynamic radius ($R_h$). Another chromatographic separation approach is illustrated by U.S. Pat. No. 5,334,310 to Fréchet et al. and involves the use of a porous monolithic stationary-phase as a separation medium within the chromatographic column, combined with a mobile-phase composition gradient. (See also, Petro et al, Molded Monolithic Rod of Macroporous Poly(styrene-co-divinylbenzene) as a Separation Medium for HPLC Synthetic Polymers: "On-Column" Precipitation-Redissolution Chromatography as an Alternative to Size Exclusion Chromatography of Styrene Oligomers and Polymers, *Anal. Chem.*, 68, 315–321 (1996); and Petro et al, Immobilization of Trypsin onto "Molded" Macroporous Poly (Glycidyl Methacrylate-co-Ethylene Dimethacrylate) Rods and Use of the Conjugates as Bioreactors and for Affinity Chromatography, *Biotechnology and Bioengineering*, Vol. 49, pp. 355–363 (1996)). Chromatography involving the porous monolith is reportedly based on a precipitation/redissolution phenomenon that separates the polymer according to size—with the precipitated polymer molecules selectively redissolving as the solvent composition is varied. The monolith provides the surface area and permeation properties needed for proper separation. Other separation approaches are also known in the art, including for example, normal-phase adsorption chromatography (with separation of polymer components being based on preferential adsorption between interactive functionalities of repeating units and an adsorbing stationary-phase) and reverse-phase chromatography (with separation of polymer components being based on hydrophobic interactions between a polymer and a non-polar stationary-phase). After separation, a detector can measure a property of the polymer or of a polymer component—from which one or more characterizing properties, such as molecular weight can be determined as a function of time. Specifically, a number of molecular-weight related parameters can be determined, including for example: the weight-average molecular weight ($M_w$), the number-average molecular weight ($M_n$), the molecular-weight distribution shape, and an index of the breadth of the molecular-weight distribution ($M_w/M_n$), known as the polydispersity index (PDI). Other characterizing properties, such as mass, particle size, composition or conversion can likewise be determined.

Flow-injection analysis techniques have been applied for characterizing small molecules, such as pigments. Typically, such techniques include the detection of a sample with a continuous-flow detector—without chromatographic separation prior to detection. However, such approaches have not, heretofore, been applied in the art of polymer characterization. Moreover, no effort has been put forth to optimize such approaches with respect to sample-throughput.

A variety of continuous-flow detectors have been used for measurements in liquid chromatography systems. Common flow-through detectors include optical detectors such as a differential refractive index detector (RI), an ultraviolet-visible absorbance detector (UV-VIS), or an evaporative mass detector (EMD)—sometimes referred to as an evaporative light scattering detector (ELSD). Additional detection instruments, such as a static-light-scattering detector (SLS), a dynamic-light-scattering detector (DLS), and/or a capillary-viscometric detector (C/V) are likewise known for measurement of properties of interest. Light-scattering methods, both static and dynamic, are established in several areas of polymer analysis. Static light scattering (SLS) can be used to measure $M_w$ and the radii of gyration ($R_g$) of a polymer in a dilute solution of known concentration. Dynamic light scattering (DLS) measures the fluctuations in the scattering signal as a function of time to determine the diffusion constant of dissolved polymer chains or other scattering species in dilute solution or of polymer particles comprising many chains in a heterogeneous system such as dilute emulsion or latex dispersion. The hydrodynamic radius, $R_h$, of the chains or particles can then be calculated based on well-established models.

Presently known liquid chromatography systems and flow-injection analysis systems are not suitable for efficiently screening larger numbers of polymer samples. Known chromatographic techniques can typically take up to an hour for each sample to ensure a high degree of separation over the wide range of possible molecular weights (i.e., hydrodynamic volumes) for a sample. The known chromatographic techniques can be even longer if the sample is difficult to dissolve or if other problems arise. Additionally, polymer samples are typically prepared for characterization manually and individually, and some characterization systems require specially-designed sample containers and/or substantial delay-times. For example, optical methods such as light-scattering protocols typically employ detector-specific cuvettes which are manually placed in a proper location in the light-scattering instrument. Such optical protocols can also require a sample to thermally equilibrate for several minutes before measurement. Moreover, because of the nature of many commercial polymers and/or polymer samples—such as their non-polarity and insolubility in water and/or alcohols, their heterogeneous nature, their lack of sequence specificity, among other aspects, the methods, systems and devices developed in connection with the biotechnological, pharmaceutical and clinical-diagnostic arts are generally not instructive for characterizing polymers. Hence, known approaches are not well suited to the rapid characterization of polymers.

Aspects of polymer characterization, such as sample preparation and polymer separation, have been individually and separately investigated. For example, Poché et al. report a system and approach for automated high-temperature dissolution of polymer samples. See Poché et al., Use of Laboratory Robotics for Gel Permeation Chromatography Sample Preparation: Automation of High-Temperature Polymer Dissolution, *J. Appl. Polym. Sci.,* 64(8), 1613–1623 (1997). Stationary-phase media that reduce chromatographic separation times of individual polymer samples have also been reported. See, for example, Petro et al., Molded continuous poly(styrene-co-divinylbenzene) rod as a separation medium for the very fast separation of polymers; Comparison of the chromatographic properties of the monolithic rod with columns packed with porous and no-porous beads in high-performance liquid chromatography., *Journal of Chromatography A,* 752, 59–66 (1996); and Petro et al., Monodisperse Hydrolyzed Poly(glycidyl methacrylate-co-ethylene dimethacrylate) Beads as a Stationary Phase for Normal-Phase HPLC, *Anal. Chem.,* 69, 3131 (1997). However, such approaches have not contemplated nor been incorporated into protocols and systems suitable for large-scale, or even moderate-scale, combinatorial chemistry research, and particularly, for combinatorial material science research directed to the characterization of polymers.

With the development of combinatorial techniques that allow for the parallel synthesis of arrays comprising a vast number of diverse industrially relevant polymeric materials, there is a need for methods and devices and systems to rapidly characterize the properties of the polymer samples that are synthesized

SUMMARY OF INVENTION

It is therefore an object of the present invention to provide systems and protocols for characterizing combinatorial libraries of polymer samples, and particularly, libraries of or derived from polymerization product mixtures, to facilitate the discovery of commercially important polymeric materials, catalysts, polymerization conditions and/or post-synthesis processing conditions. It is also an object of the invention to provide polymer characterization systems and protocols that can be employed in near-real-time industrial process control.

Briefly, therefore, this invention provides methods and apparatus for the rapid characterization or screening of polymers by chromatographic techniques and related flow-injection analysis techniques, and particularly, those employing optical detection methods. This invention provides a number of embodiments for such rapid characterization or screening of polymers and those embodiments can be employed individually or combined together. More specifically, polymer characterization approaches and devices are presented involving flow characterization and non-flow characterization, and with respect to both of the same, involving rapid-serial, parallel, serial-parallel and hybrid parallel-serial approaches. Some preferred approaches and embodiments are directed to rapid-serial flow characterization of polymer samples.

Among the several significant aspects of the rapid-serial flow characterization techniques are protocols and systems related to automated sampling, chromatographic separation (where applicable) and/or detection—which individually and collectively improve the sample-throughput when applied to characterize a plurality of polymer samples. The automated polymer sampling can be effected at faster sampling rates, with equipment optimized for such purposes, and in sequences that benefit overall throughput and/or minimize extraneous steps. A number of chromatographic separation techniques can be employed to efficiently and effectively separate one or more of the various components of a heterogeneous polymer sample from one or more other components thereof. Generally, such techniques relate to column geometry, separation medium and mobile-phase medium. Certain approaches and systems disclosed herein involve improved aspects of detection. In addition, rapid, indirect calibration standards and methods impact overall system speed. Moreover, several important aspects of the invention have direct implications for high-temperature characterization efforts (typically ranging from about 75° C. to about 225° C.).

Many of such aspects of the invention can be directly translated for use with parallel or serial-parallel protocols, in addition to rapid-serial protocols. In a preferred embodiment, for example, a parallel or serial-parallel dynamic light-scattering system and protocols can be used for polymer characterization with very high sample throughput.

Hence the methods, systems and devices of the present invention are particularly suited for screening of arrays of polymerization product mixtures prepared in the course of combinatorial materials discovery—thereby providing a means for effectively and efficiently characterizing large numbers of different polymeric materials. While such methods, systems and devices have commercial application in combinatorial materials science research programs, they can likewise be applied in industrial process applications for near-real-time process monitoring or process control.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIG. 1A through FIG. 1F are schematic diagrams showing an overview of polymer characterization process steps (FIG. 1A), a rapid-serial protocol for effecting such steps (FIG. 1B) for a plurality of samples ($s_1, s_2, s_3 \ldots s_n$) to obtain corresponding characterizing property information ($p_1, p_2, p_3 \ldots p_n$), a parallel protocol for effecting such steps (FIG. 1C) and several parallel-serial hybrid protocols for effecting such steps (FIG. 1D, FIG. 1E, FIG. 1F).

FIG. 3 is a schematic diagram illustrating an eight-port injection valve used for loading a polymer sample and for injection thereof into a mobile phase of a flow characterization system.

FIG. 4 is a schematic diagram illustrating an automated sampling system.

FIG. 5A through FIG. 5C are views of several embodiments of a temperature-controlled auto-sampler injection probe. FIGS. 5A and 5B are cross-sectional side views of an auto-sampler probe having a resistive temperature-control element (FIG. 5A) and a fluid heat-exchanger type temperature-control element (FIG. 5B), respectively. FIG. 5C is a perspective view of an auto-sampler probe having a body with a large thermal mass.

FIGS. 7A and 7B are schematic diagrams illustrating preferred embodiments of flow characterization systems capable of use for liquid chromatography or flow-injection analysis and having a single microprocessor control (FIG. 7A) or multi-microprocessor control (FIG. 7B). FIG. 7C is a schematic diagram illustrating a preferred embodiment for a flow-injection analysis system, referred to as a flow-injection light-scattering (FILS) system. FIG. 7D is a schematic diagram illustrating one approach for effecting control of the mobile-phase flowrate in a variable-flow light-scattering system.

FIG. 8 is a graph of detector output (mv) versus time (minutes) illustrating the results from a gel permeation/adsorption HPLC separation of a typical emulsion sample diluted by THF from Example 10. The upper trace is from a refractive index (RI) detector. The lower two traces are from a static light-scattering detector (SLS) at 90° (middle trace) and at 15° (lower trace).

FIG. 9 is a graph of retentate amount (%) versus time (minutes) illustrating refractive index traces for latex particles of different sizes (204 nm, 50 nm, 19 nm) from Example 11 following chromatographic separation (main traces), and without chromatographic separation (superimposed traces in lower-left-hand corner).

FIG. 10 is a graph of detector response (mv) versus time (minutes) illustrating light-scattering traces (LS 90°—upper set of traces) and refractive index traces (RI—lower set of traces) for latex particles of different sizes (204 nm, 50 nm, 19 nm) under the same flow conditions from Example 12.

FIG. 11A is a graph of detector response (au) versus time (minutes)—showing overlaid chromatographs from a set of polymer standards. FIG. 11B is a calibration curve corresponding to the traces of FIG. 11A.

FIG. 12A through FIG. 12C are graphs showing the results of Example 16. FIG. 12A is a graph of detector response (mv) versus retention time (minutes) and includes traces for each of a plurality of serially-characterized samples—with the traces being electronically overlaid on a single chromatograph. FIG. 12B is a graph of detector response (mv) versus retention time (minutes) for a "single-shot" indirect calibration standard for the samples being characterized. FIG. 12C is a graph of log molecular weight versus retention time (minutes) and is the calibration curve corresponding to FIG. 12B.

FIG. 13 is a graph of detector response (mv) versus retention time (minutes) as a chromatograph for a representative sample characterized in Example 17.

FIGS. 14A and 14B are three-dimensional bar-graphs showing the determined weight-average molecular weight for each of the samples of a library of samples (identified by location in a 96-well microtiter-type sample-container having 8 rows and 12 columns) as characterized using accelerated SEC (FIG. 14A) and rapid SEC (FIG. 14B) approaches detailed in Example 18A.

FIGS. 15A through 15F are graphs showing data from Example 18B. FIGS. 15A through 15C show the determined weight-average molecular weight (FIG. 15A), the determined polydispersity index (FIG. 15B) and the determined conversion (FIG. 15C) for each of the library samples (identified by location in a 96-well microtiter-type sample-container having 8 rows and 12 columns) as characterized using an accelerated SEC approach. FIGS. 15D through 15F show the determined weight-average molecular weight (FIG. 15D), the determined polydispersity index (FIG. 15E) and the determined conversion (FIG. 15F) for each of the library samples as characterized using an enhanced rapid SEC approach. For each graph, values for the determined properties are represented by relative size of the circle indicated for that sample. The absence of a circle for a particular sample indicates that the property was not determined for that particular sample.

FIG. 18A is a graph of detector response (mv) versus retention time (minutes) for serially characterized polystyrene standards overlaid as a single trace. FIG. 18B is a graph of log molecular weight versus retention time as a calibration curve for representative polyethylene standards.

FIG. 19A is a graph of detector response (mv) versus retention time (minutes) for serially characterized representative polystyrene standards and polyethylene standards overlaid as a single trace. FIG. 19B is a graph of log molecular weight versus retention time as a calibration curve for representative polyethylene standards.

FIG. 20 is a graph of detector response (mv) versus retention time (minutes) with superimposed traces for a polyethylene (PE) polymer sample characterized by liquid chromatography approach illustrated in Example 22. Elution of the PE sample was effectively controlled by controlling the temperature of the mobile phase—in a first experiment as continuously "hot trichlorobenzene (TCB)" and in a second experiment as "cold TCB" for about 2 minutes and then "hot TCB" for the remainder of the run.

FIGS. 23A and 23B are graphs of log molecular weight versus retention time (minutes) developed in connection with Example 25. FIG. 23A is an absolute (direct) polyisobutylene (PIB) calibration curve prepared from a set of nine commercially-available PIB standards that were individually and serially determined in nine separate characterization runs. FIG. 23B is an indirect PIB calibration curve prepared from a set of nine polystyrene (PS) standards preselected based on hydrodynamic volume to correspond with certain PIB standards, and pooled to form a set of polystyrene standards (the small molecular weight standard being omitted), that were, effectively, a composition suitable for single-shot indirect calibration for polyisobutylene.

Figure 1C:
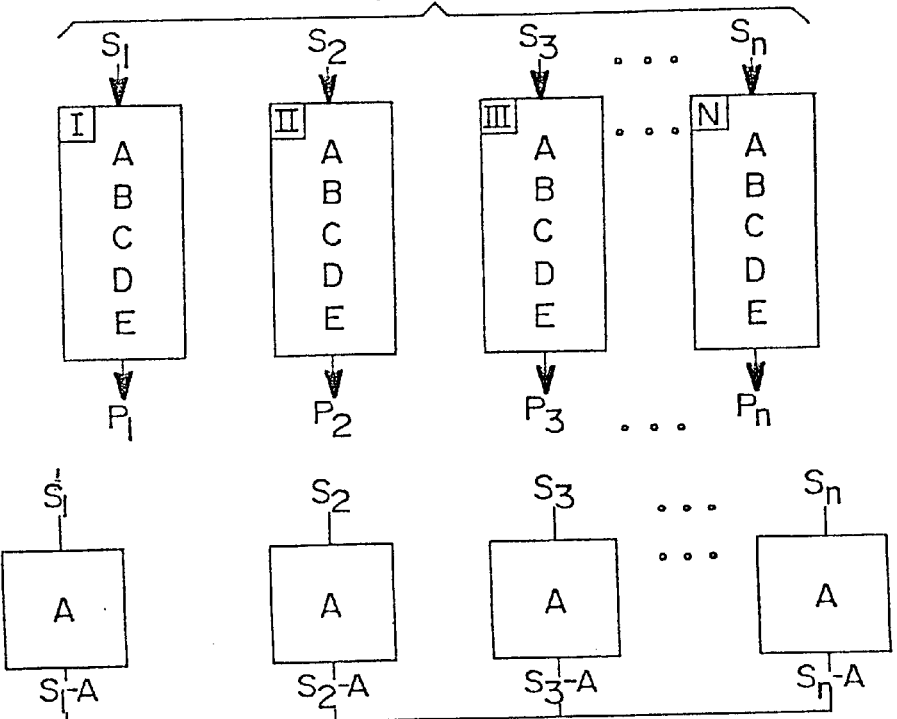

The invention is described in further detail below with reference to the figures, in which like items are numbered the same in the several figures.

DETAILED DESCRIPTION OF THE INVENTION

In the present invention, methods and apparatus having features that enable an effective combinatorial polymer research program are provided. Such a research program may be directed, for example, to identifying or optimizing commercially valuable polymers, catalysts or other materials, or to other research goals, such as process characterization and optimization. Other applications, including industrial process monitoring or control are also enabled by the present invention.

More specifically, polymer characterization approaches and devices are presented involving flow characterization and non-flow characterization, and with respect to both of the same, involving rapid-serial, parallel, serial-parallel and hybrid parallel-serial approaches. Some preferred approaches and embodiments are directed to rapid-serial flow characterization of polymer samples. Among the several significant aspects of the rapid-serial flow characterization techniques are protocols and systems related to automated sampling, chromatographic separation (where applicable) and/or detection—which individually and collectively improve the sample-throughput when applied to characterize a plurality of polymer samples.

With respect to automated polymer sampling, for example, a plurality of polymer samples can be loaded into a flow characterization system using an auto-sampler having a very high sampling rate—less than 10 seconds per sample, or in some embodiments, less than 5 seconds per sample. Additionally, automated sample preparation can be effected in a direct rapid-serial manner (i.e., serial sample withdrawal-preparation-loading). The plurality of samples can be loaded, moreover, into an injection valve having two sample-loops—thereby providing a load-load capability wherein a second sample can be loaded while the first sample is being injected into the characterization system.

With respect to chromatographic separation, a number of techniques can be employed to efficiently and effectively separate one or more of the various components of a heterogeneous polymer sample from one or more other components thereof. For example, the column geometry, preferably in combination with the separation medium, can be optimized to obtain the desired throughput. Preferred column geometries include relatively short, high-aspect ratio columns (as compared to conventional columns). Preferred separation media include a stationary phase selected for targeted separation ranges—for example, to quickly pass a high molecular-weight fraction of a sample (e.g., > about 1000 D) while retaining a low molecular-weight fraction of the sample. Other separation medium optimization approaches, such as combining size-exclusion chromatography (SEC) with an adsorption chromatography, are also preferred in some applications. The mobile phase of a liquid chromatography system can also be controlled to improve sample-throughput. For example, mobile-phase compositional gradients, mobile-phase temperature gradients or mobile-phase flowrate gradients can be employed individually or collectively, and the time-rate of change of such gradients can affect separation performance. For some applications, solvent selection can itself be optimized to improve the efficiency of loading and/or eluting the sample or components thereof onto/from the stationary phase.

For flow characterization systems generally (including both liquid chromatography systems and flow-injection analysis systems), the flow-rate of the mobile phase can be increased substantially (e.g., by a factor of ten or more) relative to conventional flow characterization systems. The mobile phase flow rates can also be temporally varied as a sample moves through a flow characterization system—for example, with relatively high flowrates to advance the sample to a detector, and relatively slow flowrates to detect a property of the sample or of a component thereof.

With respect to detection, a low-molecular weight insensitive mass detector, such as an evaporative light-scattering detector (ELSD) can be advantageously employed in liquid chromatography approaches in cooperation with overlaid sample injection approaches. Specifically, trailing-edge components from a preceding sample and leading-edge components from a succeeding sample can reside in a detection cavity simultaneously, without compromising relevant data collection. In addition, rapid, indirect calibration standards and methods impact overall system speed.

Several important aspects of the invention have direct implications for high-temperature characterization efforts (typically ranging from about 75° C. to about 225° C.). With regard to polymer sampling, for example, a directly heated auto-sampler probe is employed. Chromatographic columns of relatively small mass (as compared to conventional columns) allow for rapid thermal equilibrilization of the system. With respect to chromatographic separation, mobile-phase temperature and composition gradients can be employed. Finally, detectors that are less-sensitive to variations in temperature, as compared with typical high-temperature characterization detectors, offer a greater degree of freedom for system configuration at reduced costs.

Many of such aspects of the invention can be directly translated for use with parallel or serial-parallel protocols, in addition to rapid-serial protocols. In a preferred embodiment, for example, a parallel or serial-parallel dynamic light-scattering system and protocols can be used for polymer characterization with very high sample throughput.

These and other aspects of the invention are to be considered exemplary and non-limiting, and are discussed in greater detail below. The several aspects of the polymer characterization methods and systems disclosed and claimed herein can be advantageously employed separately, or in combination to efficiently characterize polymeric materials. In preferred embodiments, these features are employed in combination to form a polymer characterization system that can operate as a high-throughput screen in a materials science research program directed to identifying and optimizing new polymers, new catalysts, new polymerization reaction conditions and/or new post-synthesis processing conditions. Certain characterizing information—particularly molecular weight, molecular weight distribution, composition and conversion information—are broadly useful for characterizing polymers and polymerization reactions. As such, the particular polymers and/or mechanisms disclosed herein should be considered exemplary of the invention and non-limiting as to the scope of the invention.

Combinatorial Approaches for Polymer Science Research

In a combinatorial approach for identifying or optimizing polymeric materials or polymerization reaction conditions, a large compositional space (e.g., of monomers, comonomers, catalysts, catalyst precursors, solvents, initiators, additives, or of relative ratios of two or more of the aforementioned) and/or a large reaction condition space (e.g., of temperature, pressure and reaction time) may be rapidly explored by preparing polymer libraries and then rapidly screening such libraries. The polymer libraries can comprise, for example, polymerization product mixtures resulting from polymerization reactions that are varied with respect to such factors.

Combinatorial approaches for screening a polymer library can include an initial, primary screening, in which polymerization product mixtures are rapidly evaluated to provide valuable preliminary data and, optimally, to identify several "hits"—particular candidate materials having characteristics that meet or exceed certain predetermined metrics (e.g., performance characteristics, desirable properties, unexpected and/or unusual properties, etc.). Such metrics may be defined, for example, by the characteristics of a known or standard polymer or polymerization scheme. Because local performance maxima may exist in compositional spaces between those evaluated in the primary screening of the first libraries or alternatively, in process-condition spaces different from those considered in the first screening, it may be advantageous to screen more focused polymer libraries (e.g., libraries focused on a smaller range of compositional gradients, or libraries comprising compounds having incrementally smaller structural variations relative to those of the identified hits) and additionally or alternatively, subject the initial hits to variations in process conditions. Hence, a primary screen can be used reiteratively to explore localized and/or optimized compositional space in greater detail. The preparation and evaluation of more focused polymer libraries can continue as long as the high-throughput primary screen can meaningfully distinguish between neighboring library compositions or compounds.

Once one or more hits have been satisfactorily identified based on the primary screening, polymer and polymerization product libraries focused around the primary-screen hits can be evaluated with a secondary screen—a screen designed to provide (and typically verified, based on known materials, to provide) chemical process conditions that relate with a greater degree of confidence to commercially-important processes and conditions than those applied in the primary screen. In many situations, such improved "real-world-modeling" considerations are incorporated into the secondary screen at the expense of methodology speed (e.g., as measured by sample throughput) compared to a corresponding primary screen. Particular polymer materials, catalysts, reactants, polymerization conditions or post-synthesis processing conditions having characteristics that surpass the predetermined metrics for the secondary screen may then be considered to be "leads." If desired, additional polymer or polymerization product libraries focused about such lead materials can be screened with additional secondary screens or with tertiary screens. Identified lead polymers, monomers, catalysts, catalyst precursors, initiators, additives or reaction conditions may be subsequently developed for commercial applications through traditional bench-scale and/or pilot scale experiments.

While the concept of primary screens and secondary screens as outlined above provides a valuable combinatorial research model for investigating polymers and polymerization reactions, a secondary screen may not be necessary for certain chemical processes where primary screens provide an adequate level of confidence as to scalability and/or where market conditions warrant a direct development approach. Similarly, where optimization of materials having known properties of interest is desired, it may be appropriate to start with a secondary screen. In general, the systems, devices and methods of the present invention may be applied as either a primary or a secondary screen, depending on the specific research program and goals thereof. See, generally, U.S. patent application Ser. No. 09/227,558 entitled "Apparatus and Method of Research for Creating and Testing Novel Catalysts, Reactions and Polymers", filed Jan. 8, 1999 by Turner et al., for further discussion of a combinatorial approach to polymer science research.

Polymer Characterization—General Approaches

According to the present invention, methods, systems and devices are disclosed that improve the efficiency and/or effectiveness of the steps necessary to characterize a polymer sample or a plurality of polymer samples (e.g., libraries of polymerization product mixtures). In preferred embodiments, a property of a plurality of polymer samples or of components thereof can be detected in a polymer characterization system with an average sample-throughput sufficient for an effective combinatorial polymer science research program.

With reference to FIG. 1A, characterizing a polymer sample can include (A) preparing the sample (e.g., dilution), (B) injecting the sample into a mobile phase of a flow characterization system (e.g., liquid chromatography system, flow-injection analysis system), (C) separating the sample chromatographically, (D) detecting a property of the polymer sample or of a component thereof, and/or (E) correlating the detected property to a characterizing property of interest. As depicted in FIG. 1A, various characterization protocols may be employed involving some or all of the aforementioned steps. For example, a property of a polymer sample may be detected in a non-flow, static system either with preparation (steps A and D) or without preparation (step D). Alternatively, a property of a polymer sample may be detected in a flow characterization system—either with or without sample preparation and either with or without chromatographic separation. In characterization protocols involving flow characterization systems without chromatographic separation (referred to herein as flow-injection analysis systems) a property of a polymer sample may be detected in a flow-injection analysis system either with preparation (steps A, B and D) or without preparation (steps B and D). If chromatographic separation of a polymer sample is desired, a property of the sample may be detected in a liquid chromatography system either with preparation (steps A, B, C and D) or without preparation (steps B, C and D). While the physically-detected property (e.g., refracted light, absorbed light, scattered light) from two samples being screened could be compared directly, in most cases the detected property is preferably correlated to a characterizing property of interest (e.g., molecular weight) (step E).

A plurality of polymer samples may be characterized as described above in connection with FIG. 1A. As a general approach for improving the sample throughput for a plurality of polymers, each of the steps, (A) through (E) of FIG. 1A applicable to a given characterization protocol can be optimized with respect to time and quality of information, both individually and in combination with each other. Additionally or alternatively, each or some of such steps can be effected in a rapid-serial, parallel, serial-parallel or hybrid parallel-serial manner.

The throughput of a plurality of samples through a single step in a characterization process is improved by optimizing the speed of that step, while maintaining—to the extent necessary—the information-quality aspects of that step. In many cases, such as with chromatographic separation, speed can be gained at the expense of resolution of the separated components. Although conventional research norms, developed in the context in which research was rate-limited primarily by the synthesis of polymer samples, may find such an approach less than wholly satisfactory, the degree of rigor can be entirely satisfactory for a primary or a secondary screen of a combinatorial library of polymer samples. For combinatorial polymer research (and as well, for many on-line process control systems), the quality of information should be sufficiently rigorous to provide for scientifically acceptable distinctions between the compounds or process conditions being investigated, and for a secondary screen, to provide for scientifically acceptable correlation (e.g., values or, for some cases, trends) with more rigorous, albeit more laborious and time-consuming traditional characterization approaches.

The throughput of a plurality of samples through a series of steps, where such steps are repeated for the plurality of samples, can also be optimized. In one approach, one or more steps of the cycle can be compressed relative to traditional approaches or can have leading or lagging aspects truncated to allow other steps of the same cycle to occur sooner compared to the cycle with traditional approaches. In another approach, the earlier steps of a second cycle can be performed concurrently with the later steps of a first cycle. For example, with reference to FIG. 1A in a rapid-serial approach for characterizing a sample, sample preparation for a second sample in a series can be effected while the first sample in the series is being separated and/or detected. As another example, a second sample in a series can be injected while the first sample in the series is being separated and/or detected. These approaches, as well as others, are discussed in greater detail below.

A characterization protocol for a plurality of samples can involve a single-step process (e.g., direct, non-flow detection of a property of a polymer sample or of a component thereof, depicted as step D of FIG. 1A). In a rapid-serial detection approach for a single-step process, the plurality of polymer samples and a single detector are serially positioned in relation to each other for serial detection of the samples. In a parallel detection approach, two or more detectors are employed to detect a property of two or more samples simultaneously. In a direct, non-flow detection protocol, for example, two or more samples and two or more detectors can be positioned in relation to each other to detect a property of the two or more polymer samples simultaneously. In a serial-parallel detection approach, a property of a larger number of polymer samples (e.g., four or more) is detected as follows. First, a property of a subset of the four or more polymer samples (e.g., 2 samples) is detected in parallel for the subset of samples, and then serially thereafter, a property of another subset of four or more samples is detected in parallel.

For characterization protocols involving more than one step (e.g., steps A, D and E; steps B, D and E; steps A, B, D and E; steps B, C, D and E; or steps A, B, C, D and E of FIG. 1A), optimization approaches to effect high-throughput polymer characterization can vary. As one example, represented schematically in FIG. 1B, a plurality of polymer samples can be characterized with a single polymer characterization system (I) in a rapid-serial approach in which each of the plurality of polymer samples ($s_1, s_2, s_3 \ldots s_n$) are processed serially through the characterization system (I) with each of the steps (A, B, C, D, E) effected in series on each of the of samples to produce a serial stream of corresponding characterizing property information ($p_1, p_2, p_3 \ldots p_n$). This approach benefits from minimal capital investment, and may provide sufficient throughput—particularly when the steps (A) through (E) have been optimized with respect to speed and quality of information. As another example, represented schematically in FIG. 1C, a plurality of polymer samples can be characterized with two or more polymer characterization systems (I, II, III . . . N) in a pure parallel (or for larger libraries, serial-parallel) approach in which the plurality of polymer samples ($s_1, s_2, s_3 \ldots s_n$) or a subset thereof are processed through the two or more polymer characterization systems (I, II, III . . . N) in parallel, with each individual system effecting each step on one of the samples to produce the characterizing property information ($p_1, p_2, p_3 \ldots p_n$) in parallel. This approach is advantageous with respect to overall throughput, but may be constrained by the required capital investment.

Figure 1D:
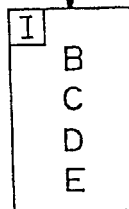
Figure 1E:
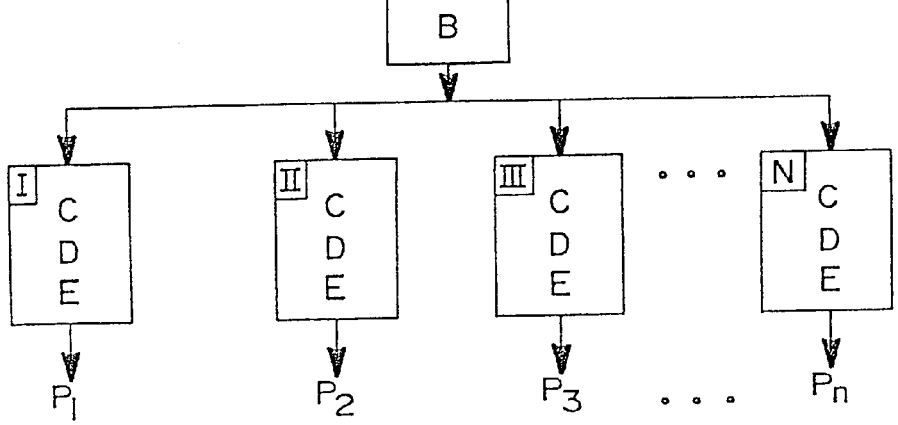
Figure 1F:
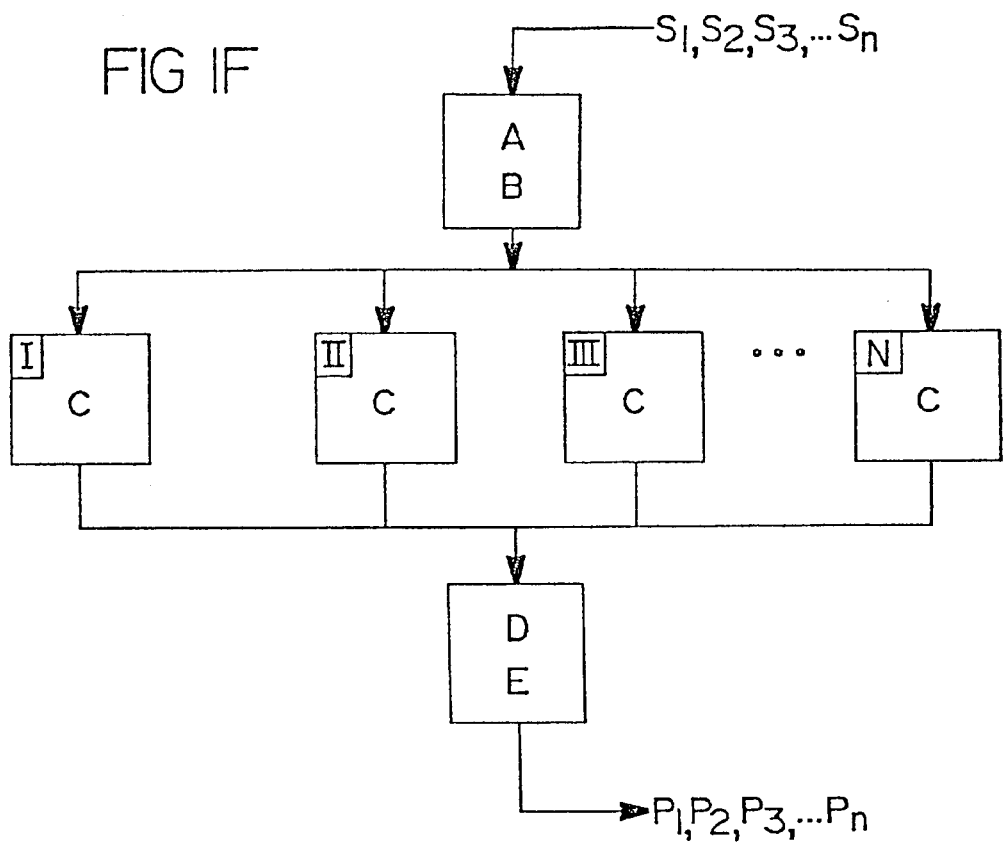

In a hybrid approach, certain of the steps of the characterization process can be effected in parallel, while certain other steps can be effected in series. Preferably, for example, it may be desirable to effect the longer, throughput-limiting steps in parallel for the plurality of samples, while effecting the faster, less limiting steps in series. Such a parallel-series hybrid approach can be exemplified, with reference to FIG. 1D, by parallel sample preparation (step A) of a plurality of polymer samples ($s_1, s_2, s_3 \ldots s_n$), followed by serial injection, chromatographic separation, detection and correlation (steps B, C, D and E) with a single characterization system (I) to produce a serial stream of corresponding characterizing property information ($p_1, p_2, p_3 \ldots p_n$). In another exemplary parallel-series hybrid approach, represented schematically in FIG. 1E, a plurality of polymer samples ($s_1, s_2, s_3 \ldots s_n$) are prepared and injected in series into the mobile phase of four or more liquid chromatography characterizing systems (I, II, III . . . N), and then separated, detected and correlated in a slightly offset (staggered) parallel manner to produce the characterizing property information ($p_1, p_2, p_3 \ldots p_n$) in the same staggered-parallel manner. If each of the separation and detection systems has the same processing rates, then the extent of the parallel offset (or staggering) will be primarily determined by the speed of the serial preparation and injection. In a variation of the preceding example, with reference to FIG. 1F, where the detection and correlation steps are sufficient fast, a plurality of polymer samples ($s_1, s_2, s_3 \ldots s_n$) could be characterized by serial sample preparation and injection, staggered-parallel chromatographic separation, and then serial detection and correlation, to produce the characterizing property information ($p_1, p_2, p_3 \ldots p_n$) in series. In this case, the rate of injection into the various separation columns is preferably synchronized with the rate of detection.

Optimization of individual characterization steps (e.g., steps (A) through (E) of FIG. 1A) with respect to speed and quality of information can improve sample throughput regardless of whether the overall characterization scheme involves a rapid-serial or parallel aspect (i.e., true parallel, serial-parallel or hybrid parallel-series approaches). As such, the optimization techniques disclosed hereinafter, while discussed primarily in the context of a rapid-serial approach, are not limited to such an approach, and will have application to schemes involving parallel characterization protocols.

Polymer Samples

The polymer sample can be a homogeneous polymer sample or a heterogeneous polymer sample, and in either case, comprises one or more polymer components. As used herein, the term "polymer component" refers to a sample component that includes one or more polymer molecules. The polymer molecules in a particular polymer component have the same repeat unit, and can be structurally identical to each other or structurally different from each other. For example, a polymer component may comprise a number of different molecules, with each molecule having the same repeat unit, but with a number of molecules having different molecular weights from each other (e.g., due to a different degree of polymerization). As another example, a heterogeneous mixture of copolymer molecules may, in some cases, be included within a single polymer component (e.g., a copolymer with a regularly-occurring repeat unit), or may, in other cases, define two or more different polymer components (e.g., a copolymer with irregularly-occurring or randomly-occurring repeat units). Hence, different polymer components include polymer molecules having different repeat units. It is possible that a particular polymer sample (e.g., a member of a library) will not contain a particular polymer molecule or polymer component of interest.

The polymer molecule of the polymer component is preferably a non-biological polymer. A non-biological polymer is, for purposes herein, a polymer other than an amino-acid polymer (e.g., protein) or a nucleic acid polymer (e.g., deoxyribonucleic acid (DNA)). The non-biological polymer molecule of the polymer component is, however, not generally critical; that is, the systems and methods disclosed herein will have broad application with respect to the type (e.g., architecture, composition, synthesis method or mechanism) and/or nature (e.g., physical state, form, attributes) of the non-biological polymer. Hence, the polymer molecule can be, with respect to homopolymer or copolymer architecture, a linear polymer, a branched polymer (e.g., short-chain branched, long-chained branched, hyper-branched), a cross-linked polymer, a cyclic polymer or a dendritic polymer. A copolymer molecule can be a random copolymer molecule, a block copolymer molecule (e.g., di-block, tri-block, multi-block, taper-block), a graft copolymer molecule or a comb copolymer molecule. The particular composition of the non-biological polymer molecule is not critical, and can include repeat units or random occurrences of one or more of the following, without limitation: polyethylene, polypropylene, polystyrene, polyolefin, polyimide, polyisobutylene, polyacrylonitrile, poly(vinyl chloride), poly(methyl methacrylate), poly(vinyl acetate), poly(vinylidene chloride), polytetrafluoroethylene, polyisoprene, polyacrylamide, polyacrylic acid, polyacrylate, poly(ethylene oxide), poly(ethyleneimine), polyamide, polyester, polyurethane, polysiloxane, polyether, polyphosphazine, polymethacrylate, and polyacetals. Polysaccharides are also preferably included within the scope of non-biological polymers. While some polysaccharides are of biological significance, many polysaccharides, and particularly semi-synthetic polysaccharides have substantial industrial utility with little, if any biological significance. Exemplary naturally-occurring polysaccharides include cellulose, dextran, gums (e.g., guar gum, locust bean gum, tamarind xyloglucan, pullulan), and other naturally-occurring biomass. Exemplary semi-synthetic polysaccharides having industrial applications include cellulose diacetate, cellulose triacetate, acylated cellulose, carboxymethyl cellulose and hydroxypropyl cellulose. In any case, such naturally-occurring and semi-synthetic polysaccharides can be modified by reactions such as hydrolysis, esterification, alkylation, or by other reactions.

In typical applications, a polymer sample is a heterogeneous sample comprising one or more polymer components, one or more monomer components and/or a continuous fluid phase. In copolymer applications, the polymer sample can comprise one or more copolymers, a first comonomer, a second comonomer, additional comonomers, and/or a continuous fluid phase. The polymer samples can, in any case, also include other components, such as catalysts, catalyst precursors (e.g., ligands, metal-precursors), solvents, initiators, additives, products of undesired side-reactions (e.g., polymer gel, or undesired homopolymer or copolymers) and/or impurities. Typical additives include, for example, surfactants, control agents, plasticizers, cosolvents and/or accelerators, among others. The various components of the heterogeneous polymer sample can be uniformly or non-uniformly dispersed in the continuous fluid phase.

The polymer sample is preferably a liquid polymer sample, such as a polymer solution, a polymer emulsion, a polymer dispersion or a polymer that is liquid in the pure state (i.e., a neat polymer). A polymer solution comprises one or more polymer components dissolved in a solvent. The polymer solution can be of a form that includes well-dissolved chains and/or dissolved aggregated micelles. The solvent can vary, depending on the application, for example with respect to polarity, volatility, stability, and/or inertness or reactivity. Typical solvents include, for example, tetrahydrofuran (THF), toluene, hexane, ethers, trichlorobenzene, dichlorobenzene, dimethylformamide, water, aqueous buffers, alcohols, etc. According to traditional chemistry conventions, a polymer emulsion can be considered to comprise one or more liquid-phase polymer components emulsified (uniformly or non-uniformly) in a liquid continuous phase, and a polymer dispersion can be considered to comprise solid particles of one or more polymer components dispersed (uniformly or non-uniformly) in a liquid continuous phase. The polymer emulsion and the polymer dispersion can also be considered, however, to have the more typically employed meanings specific to the art of polymer science—of being a emulsion-polymerization product and dispersion-polymerization product, respectively. In such cases, for example, the emulsion polymer sample can more generally include one or more polymer components that are insoluble, but uniformly dispersed, in a continuous phase, with typical emulsions including polymer component particles ranging in diameter from about 2 nm to about 500 nm, more typically from about 20 nm to about 400 nm, and even more typically from about 40 nm to about 200 nm. The dispersion polymer sample can, in such cases, generally include polymer component particles that are dispersed (uniformly or nonuniformly) in a continuous phase, with typical particles having a diameter ranging from about 0.2 $\mu$m to about 1000 $\mu$m, more typically from about 0.4 $\mu$m to about 500 $\mu$m, and even more typically from about 0.5 $\mu$m to about 200 $\mu$m. Exemplary polymers that can be in the form of neat polymer samples include dendrimers, and siloxane, among others. The liquid polymer sample can also be employed in the form of a slurry, a latex, a microgel a physical gel, or in any other form sufficiently tractable for analysis as described and claimed herein. Liquid samples are useful in the automated sample-handling tools that prepare and automatically sample each member of a polymer library. Liquid samples also allow the sample to flow in the chromatographic system or characterization system. In some cases, polymer synthesis reactions (i.e., polymerizations) directly produce liquid samples. These may be bulk liquid polymers, polymer solutions, or heterogeneous liquid samples such as polymer emulsions, latices, or dispersions. In other cases, the polymer may be synthesized, stored or otherwise available for characterization in a non-liquid physical state, such as a solid state (e.g., crystalline, semi-crystalline or amorphous), a glassy state or rubbery state. Hence, the polymer sample may need to be dissolved, dispersed or emulsified to form a liquid sample by addition of a continuous liquid-phase such as a solvent. The polymer sample can, regardless of its particular form, have various attributes, including variations with respect to polarity, solubility and/or miscibility.

In preferred applications, the polymer sample is a polymerization product mixture. As used herein, the term "polymerization product mixture" refers to a mixture of sample components obtained as a product from a polymerization reaction. An exemplary polymerization product mixture can be a sample from a combinatorial library prepared by polymerization reactions, or can be a polymer sample drawn off of an industrial process line. In general, the polymer sample may be obtained after the synthesis reaction is stopped or completed or during the course of the polymerization reaction. Alternatively, samples of each polymerization reaction can be taken and placed into an intermediate array of vessels at various times during the course of the synthesis, optionally with addition of more solvent or other reagents to arrest the synthesis reaction or prepare the samples for analysis. These intermediate arrays can then be characterized at any time without interrupting the synthesis reaction. It is also possible to use polymer samples or libraries of polymer samples that were prepared previously and stored. Typically, polymer libraries can be stored with agents to ensure polymer integrity. Such storage agents include, for example, antioxidants or other agents effective for preventing cross-linking of polymer molecules during storage. Depending upon the polymerization reaction, other processing steps may also be desired, all of which are preferably automated. The polymerization scheme and/or mechanism by which the polymer molecules of the polymer component of the sample are prepared is not critical, and can include, for example, reactions considered to be addition polymerization, condensation polymerization, step-growth polymerization, and/or chain-growth polymerization reactions. Viewed from another aspect, the polymerization reaction can be an emulsion polymerization or a dispersion polymerization reaction. Viewed more specifically with respect to the mechanism, the polymerization reaction can be radical polymerization, ionic polymerization (e.g., cationic polymerization, anionic polymerization), and/or ring-opening polymerization reactions, among others. Non-limiting examples of the foregoing include, Ziegler-Natta or Kaminsky-Sinn reactions and various copolymerization reactions. Polymerization product mixtures can also be prepared by modification of a polymeric starting materials, by grafting reactions, chain extension, chain scission, functional group interconversion, or other reactions.

The sample size is not narrowly critical, and can generally vary, depending on the particular characterization protocols and systems used to characterize the sample or components thereof. Typical sample sizes can range from about 0.1 μl to about 1 ml, more typically from about 1 μl to about 1000 μl, even more typically from about 5 μl to about 100 μl, and still more typically from about 10 μl to about 50 μl. A generally preferred sample size for flow characterization systems and, particularly for liquid chromatography, is a sample size of about 20 μl.

The polymer sample, such as a polymerization product mixture, can be a raw, untreated polymer sample or can be pretreated in preparation for characterization. Typical sample preparation steps include preliminary, non-chromatographic separation of one or more components of a polymer sample from other components, dilution, mixing and/or redissolution (e.g., from a solid state), among other operations. Preliminary separation methods can help remove large-scale impurities such as dust, coagulum or other impurities. Such separation methods can include, for example: filtering (e.g., with a microfilter having pore sizes that allow the passage of particles less than about 0.5 μm or 0.2 μm); precipitation of polymer components, monomer components and/or other small-molecule components, decanting, washing, scavenging (e.g., with drying agents), membrane separation (e.g., diafiltration, dialysis), evaporation of volatile components and/or ion-exchange. The sample is preferably diluted, if necessary, to a concentration range suitable for detection. For typical liquid chromatography applications, for example, the sample concentration prior to loading into the liquid chromatography system can range from about 0.01 mg/ml to a neat sample, more typically from about 0.01 mg/ml to about 100 mg/ml, and even more typically from about 0.1 mg/ml to about 50 mg/ml. More specific concentration ranges typical for liquid chromatography samples include from about 0.1 mg/ml to about 20 mg/ml, and from about 0.5 mg/mil to about 5 mg/ml. For flow-injection analysis systems, in which the sample is detected without substantial chromatographic separation thereof, much more dilute solutions can be employed. Hence, the concentration can range from a detectable concentration level (for the particular detector employed) up to about 1 mg/ml, or more in some applications. Typical concentrations can be about $1 \times 10^{-2}$ wt %, about $1 \times 10^{-3}$ wt % or about $1 \times 10^{-4}$ wt %. Mixing can be required to increase the uniformity of a polymer sample emulsion or dispersion, and/or to integrate one or more additional components into the polymer sample. Preparation steps, and particularly rapid preparation techniques, can be an important aspect for combinatorial polymer investigations—since polymer samples may be synthesized in a form not ideally suited for immediate characterization.

Pluralities of Polymer Samples/Libraries of Polymer Samples

A plurality of polymer samples comprises 2 or more polymer samples that are physically or temporally separated from each other—for example, by residing in different sample containers, by having a membrane or other partitioning material positioned between samples, by being partitioned (e.g., in-line) with an intervening fluid, by being temporally separated in a flow process line (e.g., as sampled for process control purposes), or otherwise. The plurality of polymer samples preferably comprises 4 or more polymer samples and more preferably 8 or more polymer samples. Four polymer samples can be employed, for example, in connection with experiments having one control sample and three polymer samples varying (e.g., with respect to composition or process conditions as discussed above) to be representative of a high, a medium and a low-value of the varied factor—and thereby, to provide some indication as to trends. Four polymer samples are also a minimum number of samples to effect a serial-parallel characterization approach, as described above (e.g., with two detectors operating in parallel). Eight polymer samples can provide for additional variations in the explored factor space. Moreover, eight polymer samples corresponds to the number of parallel polymerization reactors in the PPR-8™, being selectively offered as one of the Discovery Tools™ of Symyx Technologies, Inc. (Santa Clara, Calif.). Higher numbers of polymer samples can be investigated, according to the methods of the invention, to provide additional insights into larger compositional and/or process space. In some cases, for example, the plurality of polymer samples can be 15 or more polymer samples, preferably 20 or more polymer samples, more preferably 40 or more polymer samples and even more preferably 80 or more polymer samples. Such numbers can be loosely associated with standard configurations of other parallel reactor configurations (e.g., the PPR-48™, Symyx Technologies, Inc.) and/or of standard sample containers (e.g., 96-well microtiter plate-type formats). Moreover, even larger numbers of polymer samples can be characterized according to the methods of the present invention for larger scale research endeavors. Hence, the number of polymer samples can be 150 or more, 400 or more, 500 or more, 750 or more, 1,000 or more, 1,500 or more, 2,000 or more, 5,000 or more and 10,000 or more polymer samples. As such, the number of polymer samples can range from about 2 polymer samples to about 10,000 polymer samples, and preferably from about 8 polymer samples to about 10,000 polymer samples. In many applications, however, the number of polymer samples can range from about 80 polymer samples to about 1500 polymer samples. In some cases, in which processing of polymer samples using typical 96-well microtiter-plate formatting is convenient or otherwise desirable, the number of polymer samples can be 96*N, where N is an integer ranging from about 1 to about 100. For many applications, N can suitably range from 1 to about 20, and in some cases, from 1 to about 5.

The plurality of polymer samples can be a library of polymer samples. A library of polymer samples comprises an array of two or more different polymer samples spatially separated—preferably on a common substrate, or temporally separated—for example, in a flow system. Candidate polymer samples (i.e., members) within a library may differ in a definable and typically predefined way, including with regard to chemical structure, processing (e.g., synthesis) history, mixtures of interacting components, purity, etc. The polymer samples are spatially separated, preferably at an exposed surface of the substrate, such that the array of polymer samples are separately addressable for characterization thereof. The two or more different polymer samples can reside in sample containers formed as wells in a surface of the substrate. The number of polymer samples included within the library can generally be the same as the number of samples included within the plurality of samples, as discussed above. In general, however, not all of the polymer samples within a library of polymer samples need to be different polymer samples. When process conditions are to be evaluated, the libraries may contain only one type of polymer sample. Typically, however, for combinatorial polymer science research applications, at least two or more, preferably at least four or more, even more preferably eight or more and, in many cases most, and allowably each of the plurality of polymer samples in a given library of polymer samples will be different from each other. Specifically, a different polymer sample can be included within at least about 50%, preferably at least 75%, preferably at least 80%, even more preferably at least 90%, still more preferably at least 95%, yet more preferably at least 98% and most preferably at least 99% of the polymer samples included in the sample library. In some cases, all of the polymer samples in a library of polymer samples will be different from each other.

The substrate can be a structure having a rigid or semi-rigid surface on which or into which the array of polymer samples can be formed or deposited. The substrate can be of any suitable material, and preferably consists essentially of materials that are inert with respect to the polymer samples of interest. Certain materials will, therefore, be less desirably employed as a substrate material for certain polymerization reaction process conditions (e.g., high temperatures—especially temperatures greater than about 100° C.—or high pressures) and/or for certain reaction mechanisms. Stainless steel, silicon, including polycrystalline silicon, single-crystal silicon, sputtered silicon, and silica ($SiO_2$) in any of its forms (quartz, glass, etc.) are preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. Organic and inorganic polymers may also be suitably employed in some applications of the invention. Exemplary polymeric materials that can be suitable as a substrate material in particular applications include polyimides such as Kapton™, polypropylene, polytetrafluoroethylene (PTFE) and/or polyether etherketone (PEEK), among others. The substrate material is also preferably selected for suitability in connection with known fabrication techniques. As to form, the sample containers formed in, at or on a substrate can be preferably, but are not necessarily, arranged in a substantially flat, substantially planar surface of the substrate. The sample containers can be formed in a surface of the substrate as dimples, wells, raised regions, trenches, or the like. Non-conventional substrate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications. In preferred embodiments, the substrate is designed such that the individually addressable regions of the substrate can act as polymerization reaction vessels for preparing a polymerization product mixture (as well as sample containers for the two or more different polymer samples during subsequent characterization thereof. Glass-lined, 96-well, 384-well and 1536-well microtiter-type plates, fabricated from stainless steel and/or aluminum, are preferred substrates for a library of polymer samples. The choice of an appropriate specific substrate material and/or form for certain applications will be apparent to those of skill in the art in view of the guidance provided herein.

The library of polymer materials can be a combinatorial library of polymerization product mixtures. Polymer libraries can comprise, for example, polymerization product mixtures resulting from polymerization reactions that are varied with respect to, for example, reactant materials (e.g., monomers, comonomers), catalysts, catalyst precursors, initiators, additives, the relative amounts of such components, reaction conditions (e.g., temperature, pressure, reaction time) or any other factor affecting polymerization. Design variables for polymerization reactions are well known in the art. See generally, Odian, *Principles of Polymerization*, $3^{rd}$ Ed., John Wiley & Sons, Inc. (1991). A library of polymer samples may be prepared in arrays, in parallel polymerization reactors or in a serial fashion. Exemplary methods and apparatus for preparing polymer libraries—based on combinatorial polymer synthesis approaches—are disclosed in copending U.S. patent application Ser. No. 09/211,982 of Turner et al. filed Dec. 14, 1998, copending U.S. patent application Ser. No. 09/227,558 of Turner et al. filed Jan. 8, 1999, copending U.S. patent application Ser. No. 09/235,368 of Weinberg et al. filed Jan. 21, 1999, and copending U.S. provisional patent application Ser. No. 60/122,704 entitled "Controlled, Stable Free Radical Emulsion and Water-Based Polymerizations", filed Mar. 9, 1999 by Klaerner et al. See also, PCT Patent Application WO 96/11878.

The libraries can be advantageously characterized directly, without being isolated, from the reaction vessel in which the polymer was synthesized. Thus, reagents, catalysts or initiators and other additives for making polymers may be included with the polymer sample for characterization or screening.

While such methods are preferred for a combinatorial approach to polymer science research, they are to be considered exemplary and non-limiting. As noted above, the particular polymer samples characterized according to the methods and with the apparatus disclosed herein can be from any source, including, but not limited to polymerization product mixtures resulting from combinatorially synthesis approaches.

Non-Polymer Samples

Although the primary applications of the present invention are directed to combinatorial polymer science research and/or quality control for industrial polymer synthesis or processing protocols, some aspects of the invention can have applications involving non-polymer samples. A non-polymer sample can be a material that comprises an organic or an inorganic non-polymer element or compound. Oligomers are considered to be polymers rather than non-polymers. The non-polymer molecule is, in some cases, preferably a non-biological non-polymer element or compound. Such non-biological non-polymer elements or compounds include non-polymer elements or compounds other than those having a well-characterized biological activity and/or a primary commercial application for a biological field (e.g., steroids, hormones, etc.). More particularly, such non-biological, non-polymer elements or compounds can include organic or inorganic pigments, carbon powders (e.g., carbon black), metals, metal oxides, metal salts, metal colloids, metal ligands, etc, without particular limitation.

Detectors/Detected Properties/Determined Properties

A polymer sample is characterized by detecting a property of the polymer sample, or by detecting a property of a component (e.g., a polymer component, a monomer component) of the polymer sample. In many cases, the property is detected over a period of time, such that a variation in the property can be observed or detected or the rate of change of variation of a property can be observed or detected. In the general case, the detected property can be any property which can provide a scientifically meaningful basis of comparison between two different polymer samples or between two different polymer components—either directly, or after being correlated to a specific characterizing property of interest. The detected property can be a chemical property or a physical property of the polymer sample or component thereof. In preferred applications, an optical property of the polymer sample or a component thereof can be detected. For example, an amount, frequency, intensity or direction of an incident light that is refracted, scattered, and/or absorbed by the polymer sample or a component thereof may be detected. Other properties, such as pressure or other factors affecting a particular characterizing property of interest (e.g., viscosity) can likewise be detected.

Figure 2A:
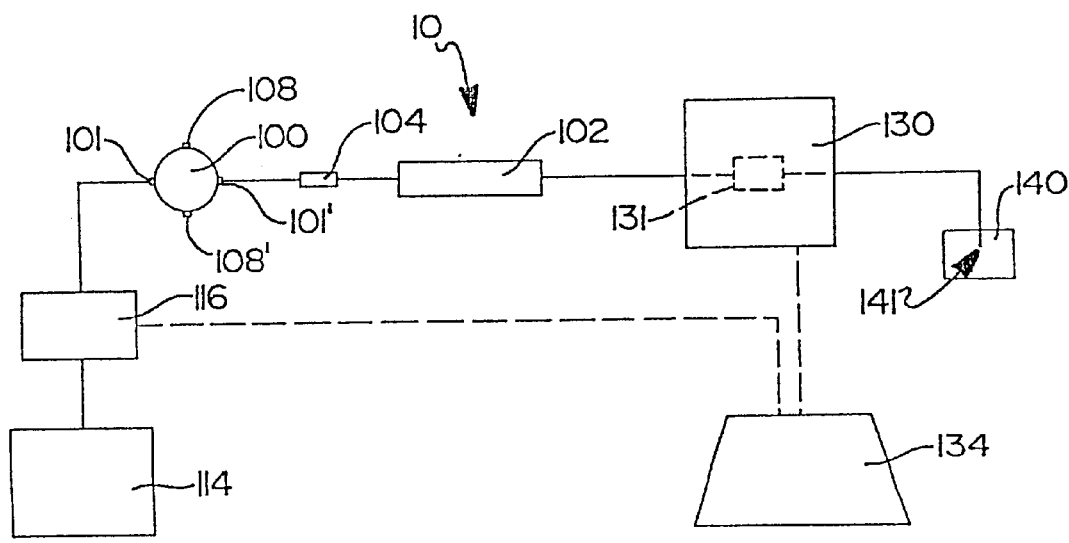
FIG. 2A and FIG. 2B are schematic diagrams illustrating liquid chromatography (FIG. 2A) and flow-injection analysis (FIG. 2B) flow characterization systems.
Figure 2B:
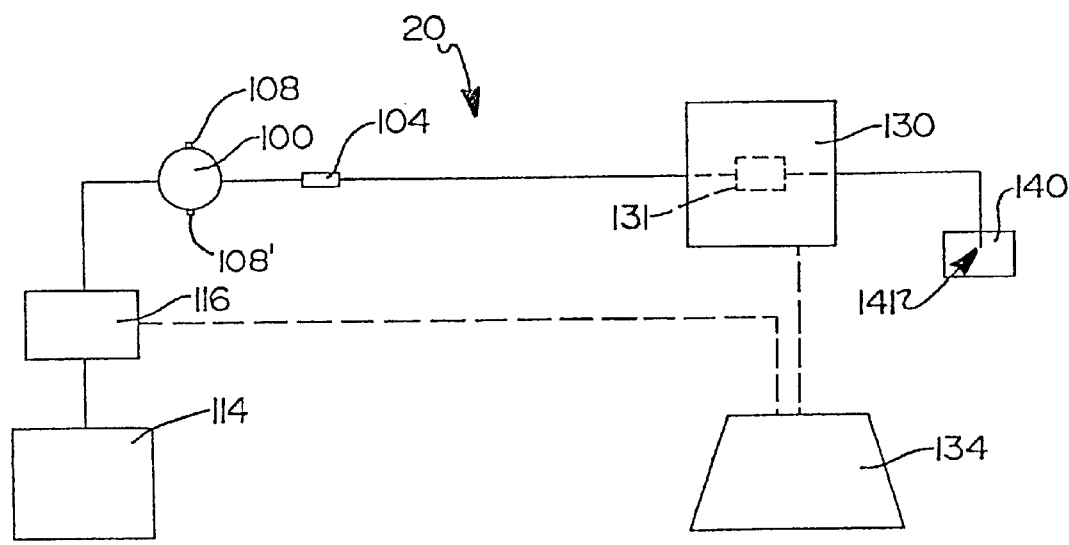

With reference to FIGS. 2A and 2B (discussed in greater detail below), a property of a polymer sample or of a component thereof, such as a chromatographically separated component thereof, can be detected in a flow characterization system with one or more detectors 130. In preferred embodiments, a property of a polymer sample or of a component thereof is detected with an optical detector such as a refractive-index detector, an ultraviolet-visual detector, a photodiode array detector, a static-light-scattering detector, a dynamic-light-scattering detector, and/or an evaporative-light-scattering detector—also known as an evaporative mass detector (EMD). Other detectors (e.g., a capillary viscometer detector, photodiode array detector (PDAD), infra-red detector, fluorescence detector, electrochemical detector, conductivity detector, etc.) can likewise be employed in connection with the present invention. The particular nature of the detector (e.g., shape and/or configuration of a detection cavity 131 within the detector) is not generally critical.

The protocols for characterizing one or more polymer samples preferably further comprise determining a property of interest from the detected property. The physically-detected properties, such as the capability of the polymer sample or component thereof to refract, scatter, emit or absorb light can be correlated to properties of interest. Such properties of interest include, without limitation, weight-average molecular weight, number-average molecular weight, viscosity-average molecular weight, peak molecular weight, approximate molecular weight, polydispersity index, molecular-weight-distribution shape, relative or absolute component concentration, chemical composition, conversion, concentration, mass, hydrodynamic radius ($R_h$), radius of gyration ($R_g$), chemical composition, amounts of residual monomer, presence and amounts of other low-molecular weight impurities in polymer samples, particle or molecular size, intrinsic viscosity, molecular shape, molecular conformation, and/or agglomeration or assemblage of molecules. The correlation between a detected property and a determined property of interest can be based on mathematical models and/or empirical calibrations. Such correlation methods are generally known in the art, and are typically incorporated into commercially-available chromatographic detectors and/or detector or data-acquisition software.

For combinatorial polymer science research applications, as well as other applications, the characterization protocols can be effected to determine at least a weight-average molecular weight as a characterization property of primary importance. Other characterization properties of interest of substantial importance, include number-average molecular weight, polydispersity index, and molecular-weight-distribution shape. For polymer samples that are polymerization product mixtures, another characterization property of substantial importance is conversion data for the polymerization reaction, typically expressed as % monomer converted into polymer. The composition of the polymer sample or of particular components thereof (e.g., polymer components) can also be of substantial importance.

For determining weight-average molecular weight from detected properties, a liquid chromatography system or a flow-injection analysis system can advantageously employ a single detector or a combination of two or more detectors. In a single-detector embodiment, for example, a dynamic light-scattering (DLS) detector can be used by itself to determine an average hydrodynamic radius or a distribution of hydrodynamic radii from the detected scattered light. The hydrodynamic radii can, in turn, be correlated to an average molecular weight or a molecular weight distribution. In a two-detector embodiment, for example, a static-light scattering (SLS) detector (where the detected scattered light is a function of weight-average molecular weight ($M_w$), concentration (C) and the square of the refractive index increment, $(dn/dC)^2$) can be combined with a refractive index (RI) detector (where the detected refracted light is a function of (C) and (dn/dC)), with an ultraviolet/visible light absorbance (UV/VIS) detector (where the detected absorbed light is a function of (C)), or with an evaporative light scattering detector (ELSD) (where the detected scattered light is a function of (C)). In another embodiment, a single-detector or multiple detectors (e.g., SLS) can detect the intensity of light scattered by the sample or sample component at two or more different angles, which can be correlated to molecular weight.

For polymer samples that are polymerization product mixtures, conversion data for the polymerization reaction of which the sample is representative can be determined by chromatographically resolving the polymer component(s) and monomer component(s), determining a molecular-weight distribution for such components, integrating areas under the respective peaks, and then comparing the integrated peak areas (e.g., using response factors for particular components and detector employed). Another approach for calculating conversion involves converting the polymer-peak area into polymer concentration or mass using a concentration-detector response calibration plot, and then comparing the portion of the polymer mass or concentration found in the sample to the expected mass or concentration assuming 100% stoichiometric conversion. Composition data for a polymer sample can be determined from the consumption of monomer or comonomers or, alternatively, from a retention time per volume of the polymer peak or a fraction thereof.

Advantageously, an ELSD detector, or other detectors that are not particularly sensitive to low-molecular weight components of a polymer sample, can be advantageously employed in connection with the flow characterization protocols of the invention to achieve a high sample-throughput. As discussed in greater detail below, detectors that are insensitive to low-molecular weight components can be advantageously employed in connection with rapid-serial overlapping techniques. Moreover, because the ELSD is also less sensitive to temperature variations than other types of mass detectors (e.g., RI detector) and is not required to be in thermal equilibrium with the sample being detected, an ELSD detector can be employed advantageously in connection with high-temperature polymer characterization systems. Hence, detecting a property of a polymer sample or a component there of with an ELSD or with other low-MW insensitive or less temperature sensitive mass detectors provides a further aspect for improving the sample throughput—particularly for a liquid chromatography system 10 or a flow-injection analysis system 20.

The aforementioned characterizing properties of interest can, once determined, be mathematically combined in various combinations to provide figures of merit for various properties or attributes of interest. In particular, for example, molecular weight, conversion and polydispersity index can be evaluated versus polymerization process time to provide mechanistic insights as to how polymers are formed. Other combinations of the fundamental characterization properties of interest will be apparent to those of skill in the art.

Specific applications and/or combinations of detectors, as well as correlation protocols, are discussed in greater detail below Sample-Throughput For methods directed to characterizing a plurality of samples, a property of each of the samples or of one or more components thereof is detected—serially or in a parallel, serial-parallel or hybrid parallel-serial manner—at an average sample throughput of not more than about 10 minutes per sample. As used in connection herewith, the term "average sample throughput" refers to the sample-number normalized total (cumulative) period of time required to detect a property of two or more polymer samples with a characterization system. The total, cumulative time period is delineated from the initiation of the characterization process for the first sample, to the detection of a property of the last sample or of a component thereof, and includes any intervening between-sample pauses in the process. The sample throughput is more preferably not more than about 8 minutes per sample, even more preferably not more than about 4 minutes per sample and still more preferably not more than about 2 minutes per sample. Depending on the quality resolution of the characterizing information required, the average sample throughput can be not more than about 1 minute per sample, and if desired, not more than about 30 seconds per sample, not more than about 20 seconds per sample or not more than about 10 seconds per sample, and in some applications, not more than about 5 seconds per sample and not more than about 1 second per sample. Sample-throughput values of less than 4 minutes, less than 2 minutes, less than 1 minute, less than 30 seconds, less than 20 seconds and less than 10 seconds are demonstrated in the examples. The average sample-throughput preferably ranges from about 10 minutes per sample to about 10 seconds per sample, more preferably from about 8 minutes per sample to about 10 seconds per sample, even more preferably from about 4 minutes per sample to about 10 seconds per sample and, in some applications, most preferably from about 2 minutes per sample to about 10 seconds per sample.

A sample-throughput of 10 minutes per sample or less is important for a number of reasons. Flow-characterization systems that detect a property of a polymer sample or of a component thereof at the aforementioned sample throughput rates can be employed effectively in a combinatorial polymer research program. From a completely practical point of view, the characterization rates are roughly commensurate with reasonably-scaled polymer sample library synthesis rates. It is generally desirable that combinatorial screening systems, such as the polymer characterization protocols disclosed herein, operate with roughly the same sample throughput as combinatorial synthesis protocols—to prevent a backlog of uncharacterized polymerization product samples. Hence, because moderate scale polymer-synthesis systems, such as the Discovery Tools™ PPR-48™ (Symyx Technologies, Santa Clara Calif.), can readily prepare polymer libraries with a sample-throughput of about 100 polymer samples per day, a screening throughput of about 10 minutes per sample or faster is desirable. Higher throughput synthesis systems demand higher characterization throughputs. The preferred higher throughput values are also important with respect to process control applications, to provide near-real time control data. It is possible, moreover, that a particular sample being characterized may include component that are themselves different analytes of interest, such that the per-analyte throughput for the characterization system can be significantly higher than the per-sample throughput thereof.

Additionally, as shown in connection with the examples provided herein, the characterization of polymer samples at such throughputs can offer sufficiently rigorous quality of data, especially weight-average molecular weight, to be useful for scientifically meaningful exploration of the polymer compositional and/or polymerization reaction conditions research space. Specifically, at sample throughputs ranging from about 10 minutes per sample to about 8 minutes per sample, the polymer sample or one or more components thereof can be characterized with respect to weight-average molecular weight, number-average molecular weight, polydispersity index, molecular weight distribution shape, and conversion information—all at reasonably high quality resolution. At a sample throughput ranging between about 8 minutes per sample to about 2 minutes per sample, the polymer sample or one or more components thereof can be characterized with respect to weight-average molecular weight—at reasonably high quality resolution, and with respect to number-average molecular weight, polydispersity index, molecular weight distribution shape, and conversion information—all with good quality resolution. See Example 17. At a sample throughput ranging between about 2 minutes per sample to about 1 minute per sample, the polymer sample or one or more components thereof can be characterized with respect to weight-average molecular weight and conversion information—at reasonably high quality resolution, and with respect to number-average molecular weight, polydispersity index, and molecular weight distribution shape—all with moderate quality resolution. See Example 16. At a sample throughput ranging between about 1 minute per sample to about 30 seconds per sample, the polymer sample or one or more components thereof can be characterized with respect to weight-average molecular weight—with moderate quality resolution. See Example 15.

Hence, the average sample-throughput can range, in preferred cases, from about 10 minutes per sample to about 8 minutes per sample, from about 8 minutes per sample to about 2 minutes per sample, from about 2 minutes per sample to about 1 minute per sample, from about 1 minute per sample to about 30 seconds per sample and from about 1 minute per sample to about 10 seconds per sample, with preferences depending on the quality of resolution required in a particular case. For example, in some research strategies, the very high sample throughputs can be effectively employed to efficiently identify a polymer sample or component thereof having a particularly desired property (e.g., such as weight-average molecular weight). In short, the search can be accelerated for the particular property of research interest.

Specific protocols, systems and devices for achieving the aforementioned average sample throughput values for a plurality of polymer samples are discussed and exemplified in greater detail below.

Flow Characterization Systems

In a preferred approach, a plurality of polymer samples are characterized by serially detecting a property of a plurality of polymer samples or of components thereof in a flow characterization system, such as a liquid chromatography system or a related, flow-injection analysis system, at an average sample-throughput of not more than about 10 minutes per sample. Unlike traditional flow characterization protocols, which are designed to achieve universality with respect to polymer type and with respect to quality of information—without substantial concern for sample throughput, the high-throughput protocols disclosed and claimed herein achieve high sample throughput, while optimizing quality and universality to the extent necessary for the particular application. Rapid characterization for individual samples and/or for a plurality of samples are achieved, in general, by improving the efficiency of sampling (polymer sample withdrawal, preparation, and delivery), chromatographic separation (for liquid chromatography systems) and detection. As such, the protocols of the invention can be advantageously employed, inter alia, for combinatorial polymer research and/or for near real time process control applications.

Liquid Chromatography Systems/Flow-Injection Analysis Systems—Overview

The polymer samples are preferably characterized according to the methods of the present invention with a flow characterization system. As used herein, the term "flow characterization system" refers to a polymer characterization system in which a polymer sample flows into a detection cavity of a flow-through detector, a property of the polymer sample or of a component thereof is detected while the sample (or a portion thereof) resides in the detection cavity, and the polymer sample flows out of the detection cavity. The flow-through detector can also be interchangeably referred to as a continuous-flow detector. A flow-through detector may have more than one detection cavity, and the flow characterization system may have more than one flow-through detector. As referred to herein, an individual flow-characterization system has a single common flow path, as delineated by a common point of sample injection (typically, through an injection valve) to a common point of sample exhaust (typically, through a sample effluent port, and usually leading to a waste collection container). The flow path of an individual flow-characterization system may, nonetheless, split internally within the system (e.g., with a flow-through detector having multiple detection cavities—such as with capillary-type detection cavities.

Flow characterization systems can be broadly classified, for purposes of the present invention, as liquid chromatography systems and flow-injection analysis systems. Liquid chromatography systems are flow characterization systems that effect at least some chromatographic separation of a polymer sample prior to detection of the sample or of components thereof in a flow-through detector. Flow-injection analysis systems are flow characterization systems without substantial chromatographic separation of the sample prior to detection with the flow-through detector. Flow-injection analysis systems can, however, include apparatus for non-chromatographic separations (e.g., filtration). Moreover, a polymer sample can be prepared, prior to flow-injection analysis (or prior to liquid chromatography), by separating one or more components of the raw sample from other components thereof.

Briefly, with reference to FIG. 2A, a liquid chromatography system 10 comprises an injection valve 100 (sometimes referred to as an injection loop) having an injection port 108, a chromatographic column 102, a flow-through detector 130, and an effluent port 141. An in-line filter 104, additional injection ports 108', additional chromatographic columns 102 and/or additional flow-through detectors 130 can also be included in the system 10. Additionally, switches (e.g., automated switches) can be included to switch between various options with respect to filters 104, columns 102, detectors 130. In operation, a mobile-phase fluid is pumped from a mobile-phase reservoir 114 by pump 116 through the injection valve 100, chromatographic column 102 and detector 130. The pump 116 can be controlled with a microprocessor 134. The mobile phase can be exhausted from the system via effluent port 141 into a waste collection container 140. A polymer sample is loaded into the injection valve 100 through the injection port 108, and the loaded sample is injected into the mobile phase of the chromatographic system. The injected sample is chromatographically separated in the chromatographic column 102. A property of the polymer sample, and/or of one or more separated components thereof, is then detected while the sample resides in a detection cavity 131 of the detector 130. A microprocessor (e.g., computer) 134 is typically in electronic communication with the detector to collect, process and analyze the data obtained therefrom. While the same microprocessor 134 is shown in the figure for pump 116 control and data acquisition, these functions could be effected with separate microprocessors 134.

With reference to FIG. 2B, a flow-injection analysis system 20 can comprise an injection valve 100 having an injection port 108, a flow-through detector 130 and an effluent port 141. The flow-injection analysis system can also include an in-line filter 104, and can have additional injection ports 108 and/or flow-through detectors 130. In operation, a mobile-phase fluid is pumped from a mobile-phase reservoir 114 by pump 116 through the injection valve 100, filter 104 (if present) and detector 130. The pump 116 can be controlled with a microprocessor 134. The mobile phase can be exhausted from the system via effluent port 141 into to a waste collection container 140. A polymer sample is loaded into the injection valve 100 through the injection port 108, and the loaded sample is injected into the mobile phase of the flow-injection analysis system. The injected sample is optionally filtered in the filter 104, and then a property of the polymer sample, and/or of components thereof, is then detected while the sample resides in a detection cavity 131 of the detector 130. A microprocessor (e.g., computer) 134 is typically in electronic communication with the detector to collect and analyze the data obtained therefrom. Although the same microprocessor 134 is shown in the figure for pump 116 control and data acquisition, these functions could be effected with separate microprocessors 134.

The components of the liquid chromatography system 10 and the flow-injection-analysis system 20 are described more specifically below. The description of components common for each of the systems 10, 20 (e.g., injection valves 100) are applicable to each such system, unless specifically designated otherwise in the context of particularly described embodiments.

Reservoir/Pumps

Referring again to FIGS. 2A and 2B, the reservoir 114 of a flow characterization system can be of any suitable design and capacity, and typically has a volume of about 4 liters. The particular mobile-phase fluid to be included in the reservoir 114 for the flow characterization system can be selected in view of the polymer sample, detector, desired flowrates, and liquid chromatography systems, further in view of the chromatographic separation technique being employed. Exemplary mobile-phase fluids for liquid chromatography systems (e.g., GPC, precipitation-redissolution chromatography, adsorption chromatography and reverse-phase chromatography) and for flow-injection analysis systems are discussed below. The pump 116 can be of any type and size suitable to provide a motive force for the mobile-phase fluid through the flow-characterization systems 10, 20. Typical high-pressure liquid chromatography pumps, available commercially from various sources, such as Waters Model No. 515 (Milford, Mass.) can be employed. The flow characterization systems 10, 20 can include additional reservoirs 114, and additional pumps 116 to provide more than one mobile-phase fluid, to provide a mobile-phase composition gradient or, as discussed below, to provide a mobile-phase temperature gradient.

Injection Valve

The injection valve 100 comprises one or more injection ports 108, one or more sample loops, one or more mobile-phase inlet ports 101, and one or more mobile-phase outlet ports 103. The polymer sample can be injected directly through an injection port 108 into the mobile phase flowing through the injection valve 100. In preferred embodiments, however, the injection valve 100 is an injection port valve typical of those used for a high pressure liquid chromatography system. As used in this context, and with application to both liquid chromatography systems 10 of the invention and flow-injection analysis systems 20 of the invention, "high pressure" refers to internal system pressures (e.g., mobile-phase pressures) above atmospheric pressure, typically ranging from about 0 psig to about 6000 psig, preferably from about 10 psig to about 4000 psig, and more typically from about 100 psig to about 2000 psig.

With reference to FIG. 3. the injection valve 100 can be an 8-port injection port valve 210 (100) that operates as follows. Numerals in parenthesis refer to corresponding parts of the injection valve of FIGS. 2A and 2B. A first polymer sample is loaded directly into an injection port 108 or indirectly through a loading port 204, transfer line 206 and the injection port 108 at relatively low pressure compared to the pressure of the mobile phase. The loading port 204 can be adapted in size to accommodate one or more injection probes (tips) of a manual or an automated sample delivery unit (e.g., an auto-sampler). When the 8-ported valve is in valve position "A" (with internal flow-paths for the valve indicated by solid lines), the first polymer sample is loaded into a sample loop 205A while the mobile phase flows through the valve via mobile-phase inlet port 101 (the flow-in port), sample loop 205B, and mobile-phase outlet port 103 (the flow-out port). The sample loops 205A and 205B can be of equal volume. A waste port 207 can be employed for receiving any overflow sample and/or for flushing the valve after each sample, if necessary. When the injection valve 210 is switched to the valve "B" position (with internal flow-paths for the valve now indicated by the dashed lines), the mobile phase then flows through the valve via mobile-phase inlet port 100, sample loop 205A, and mobile-phase outlet port 103, and the first polymer sample is thereby injected into the mobile phase of the liquid chromatography system 10 or flow-injection analysis system 20. While the first polymer sample is being injected from sample loop 205A into the mobile phase of the flow characterization system, a second polymer sample can be loaded into sample loop 205B, ready to be injected once the valve is switched back to valve position A. Eight-ported valves, such as represented in FIG. 3, can be purchased from Valco Instruments Co. Inc. (Houston, Tex.), and the purchased valve fittings can be modified as described above for use in connection with a flow characterization system. An eight port injection valve 210 is a preferred injection valve 100 because the two sample loops 205A, 205B allow the flow characterization system to be ready for sample loading at all times (i.e., has a load/load capability). As such, the eight-port valve is faster than, for example, a six port valve (e.g., a valve having only a single load position and a single inject position), and therefore, the eight-port injection valve provides one aspect for improving the sample throughput for a liquid chromatography system 10 or a flow-injection analysis system 20. While the eight-port valve 210 depicted schematically in FIG. 3 is a preferred configuration, other high-pressure injection valves can also be suitably employed, including, without limitation, valves having a greater or lesser number of ports. Typically, however, a high-pressure injection valve will have from 6 to 24 ports.

Referring to FIG. 2A, FIG. 2B and FIG. 3, the injection valve 100 (210) can be configured to have more than one injection port 108, 108' or a single injection port 108, and in either case, the single or multiple injection ports 108, 108' can be in fluid communication with a number of loading ports 204 via a number of transfer lines 206 in order to receive polymer samples independently from a number of different injection probes, including, for example, a manual injection probes, and one or more probes associated with automated delivery systems, such as one or more robotic auto-samplers. The injection valve can also have a larger number of sample loops with the same or with varying volumes, to accommodate different samples sizes.

Sampling/Auto-Sampler

Sampling of a polymer sample refers to a plurality of steps which include withdrawing a polymer sample from a sample container and delivering at least a portion of the withdrawn sample to a polymer characterization system. Sampling may also include additional steps, particularly and preferably, sample preparation steps. (See FIG. 1A). In one approach, only one polymer sample is withdrawn into the auto-sampler probe at a time and only one polymer sample resides in the probe at one time. The one polymer sample is expelled therefrom (for sample preparation and/or into the polymer characterization system) before drawing the next polymer sample. In an alternative approach, however, two or more polymer samples can be withdrawn into the auto-sampler probe sequentially, spatially separated by a solvent, such that the two or more polymer samples reside in the probe at the same time. Such a "candystriping" approach can provide for very high auto-sampler throughputs for rapid introduction of the one or more samples into the flow characterization system.

The sample container from which the polymer sample is withdrawn is not critical. The sample container can be, for example a sample-containing well. The sample-containing well can be a sample vial, a plurality of sample vials, or a sample-containing well within an array of sample-containing wells (e.g., constituting a polymer sample library). The sample container can alternatively be a sample port from a sample line in fluid communication with an industrial process line, such as a polymerization process line.

In the general case, sampling can be effected manually, in a semi-automatic manner or in an automatic manner. A polymer sample can be withdrawn from a sample container manually, for example, with a pipette or with a syringe-type manual probe, and then manually delivered to a loading port or an injection port of a polymer characterization system. In a semi-automatic protocol, some aspect of the protocol is effected automatically (e.g., delivery), but some other aspect requires manual intervention (e.g., withdrawal of polymer samples from a process control line). Preferably, however, the polymer sample(s) are withdrawn from a sample container and delivered to the characterization system in a fully automated manner—for example, with an auto-sampler.

A plurality of polymer samples, such as those included within a library of polymer samples, is preferably delivered to the injection valve 100, for loading into the flow characterization system, with an automatic delivery device, such as an auto-sampler. As used herein, the term "auto-sampler" refers to an apparatus suitable for automated sampling of polymer samples for characterization, including automated withdrawal of a polymer sample from a sample container, and automated loading of at least a portion of the withdrawn sample into an injection port or a loading port of a flow characterization system (e.g. a liquid chromatography system).

Automated sampling equipment is available commercially for introducing multiple samples into liquid flow systems in a serial manner. While such commercially-available auto-sampling equipment could be used with this invention, currently available systems have several drawbacks. First, commercially available auto-samplers typically operate with a single predefined rack or tray configuration, which contains vials in a rectangular, linear, or rotary array. Samples are loaded manually and individually into vials, and manually placed in the array for subsequent sampling. The combinatorial aspects of this invention, however, prefer automated sample preparation of vast numbers of samples, from a variety of parallel vessel arrays or reactor blocks. Additionally, commercial auto-sampling equipment is not sufficiently rapid. Conventional auto-samplers require up to several minutes per cycle to introduce a polymer sample into a flow characterization system—including steps such as sample changing, drawing, loading, and cleaning of the system in preparation for the next sample. (See comparative Ex. 1). For the purposes of this invention, more rapid sample introduction is desirable—preferably requiring much less than one minute per sample. Moreover, conventional commercially-available auto-sampling equipment is not designed for complex sample preparation, including transfer, dilution, purification, precipitation, or other steps needed to prepare elements of a combinatorial array for characterization.

As such, aspects of this invention are directed to an auto-sampler and auto-sampling methods. In a preferred embodiment, with reference to FIG. 4, an auto-sampler 200 can comprise a movable probe (tip) 201, typically mounted on a support arm 203, a translation station 221 for providing three-dimensional motion of the probe, and a microprocessor 222 for controlling three-dimensional motion of the probe between various spatial addresses. The auto-sampler 200 preferably also comprises a user-interface (not shown) to allow for user programming of the microprocessor 222 with respect to probe motion and manipulations. The probe 201 can have an interior surface defining a sample-cavity and an inlet port for fluid communication between the sample cavity and a polymer sample 20. The probe 201 is also adapted for fluid communication with an injection port 108 (FIG. 2A, FIG. 2B) or a loading port 204 of a flow characterization system. The support arm 203 is preferably an XYZ robotic arm, such as can be commercially obtained from Cavro Scientific Instruments, Inc. (Sunnyvale, Calif.) among others. To improve smoothness of operation at high speeds, such XYZ robotic arms preferably have motions based on gradient variations rather than step-function variations, and preferably are belt-driven rather than shaft driven. The microprocessor 222 can be a computer and can be the same or different from the microprocessor 134 (FIG. 2A, FIG. 2B) used to control the detectors 130 (FIG. 2A, FIG. 2B) and data acquisition therefrom. The auto-sampler can further comprise one or more pumps (not shown), preferably syringe pumps, for drawing and/or expelling liquids, and related connection lines (not shown) for fluid communication between the pumps, the probe 201, and liquid (e.g. solvent) reservoirs. Preferred embodiments include two or more syringe pumps—one with a relatively lower flowrate capacity and one with a relatively higher flowrate capacity. (See Ex. 1). Alternative pump configurations, such as peristaltic pumps, vacuum-pumps or other motive-force providing means can be used additionally or alternatively. Sampling throughputs may also be enhanced by using two or more robotic arms together (See Ex. 2). It is likewise possible to have more two or more sample probes in connection with a single robotic arm—for example, such as an array of two or more probes each capable of synchronized motion relative to each other.

In operation, the microprocessor 222 of the auto-sampler 200 can be programmed to direct the auto-sampler 200 to withdraw a polymer sample 20 (e.g., a polymer solution comprising a dissolved polymer) from a sample container (e.g., a sample well) formed in a sample tray 202 into the injection probe 201, and subsequently to direct the probe 201 to the loading port 204 for loading the sample into the characterization system through transfer line 206. In preferred embodiments, the auto-sampler can be programmed to automatically sample each well of a library of polymer samples one after the other whereby a plurality of polymer samples are serially loaded into the flow characterization system, and subsequently serially injected into the mobile phase of the characterization system in a plug flow fashion. Preferably, the microprocessor 222 of the auto-sampler comprises a user-interface that can be programmed to allow for variations from a normal sampling routine (e.g., skipping certain elements at certain spatial addresses of a library). The auto-sampler 200 can also be controlled for manual operation on an individual sample by sample basis.

The microprocessor 222 is also preferably user-programmable to accommodate libraries of polymer samples having varying arrangements of arrays of polymer samples (e.g., square arrays with "n-rows" by "n-columns", rectangular arrays with "n-rows" by "m-columns", round arrays, triangular arrays with "r-" by "r-" by "r-" equilateral sides, triangular arrays with "r-base" by "s-" by "s-" isosceles sides, etc., where n, m, r, and s are integers). More particularly, for example, with respect to square or rectangular arrays, a two sets of samples (e.g., libraries) having different spatial configurations can be sampled as follows. First, an auto-sampler is programmed (e.g., via a user interface module) with location information for a first set of samples comprising a plurality of samples in a plurality of sample containers in first spatial arrangement (e.g., "n-rows" by "m-columns", where n and m are integers). The first set of samples are serially withdrawn from their respective sample containers, and at least a portion of each of the withdrawn first set of samples are serially delivered to one or more intended locations (e.g., a characterization system). The auto-sampler is then reprogrammed with location information for a second set of liquid samples that comprise a plurality of samples in a plurality of sample containers in second spatial arrangement (e.g., "p-rows" by "q-columns", where p and q are integers). The second set of samples are serially withdrawn from their respective sample containers, and at least a portion of each of the withdrawn second set of samples are serially delivered to one or more intended locations.

In a preferred protocol for sampling a plurality of polymer samples, an auto-sampler provides for rapid-serial loading of the plurality of polymer samples into a common injection port of an injection valve. More specifically, a plurality of polymer samples is sampled as follows. At a first withdrawal time, $t_{ASW1}$, a first polymer sample is withdrawn from a first sample container at a first location into a probe of an auto-sampler. At least a portion of the withdrawn first sample is then delivered to an injection port of a polymer characterization system, either directly, or through a loading port and a transfer line. After delivery of the first polymer sample, a second polymer sample is, at a second withdrawal time, $t_{ASW2}$, withdrawn from a second sample container at a second location into the auto-sampler probe. At least a portion of the withdrawn second sample is then delivered (directly or indirectly) to the injection port of the polymer characterization system. The auto-sampler cycle time, $T_{AS}$, delineated by the difference in time, $t_{ASW2}-t_{ASW1}$, is preferably not more than about 40 seconds, more preferably not more than about 30 seconds, even more preferably not more than about 20 seconds, more preferably still not more than about 10 seconds, and most preferably not more than about 8 seconds. The cycle can then be repeated, as necessary, in an automated manner, for additional polymer samples included within the plurality of polymer samples. The operation of the auto-sampler in such a high-speed, rapid-serial manner provides another aspect for improving the sample throughput for a liquid chromatography system 10 or a flow-injection analysis system 20.

The preferred protocol for sampling a plurality of polymer samples can also include additional automated steps. Preferably for example, in an interval of the sampling cycle defined by the period of time after delivery of at least a portion of the first polymer sample into a loading port or an injection port of a flow characterization system, and before withdrawal of the second polymer sample, a residual portion of the first sample still remaining in the sample cavity of the auto-sampler probe, if any, can be expelled therefrom, for example to a waste container. Additionally or alternatively, the auto-sampler probe can be cleaned during this interval of the sampling cycle. Cleaning the auto-sampler probe, in an automated fashion, can include flushing the sample cavity of the probe with a solvent source available to the probe, and then expelling the solvent into a waste container. Such withdrawal and expelling of a cleaning solvent can be repeated one or more times, as necessary to effectively limit the extent of cross-contamination between the first and second polymer samples to a level that is acceptable. As an alternative or additional cleaning protocol, the probe may be immersed in a cleaning solution and moved around therein to effectively rinse residual polymer sample from both the external portion of the probe and the sample cavity thereof. The expelling step and the one or more cleaning steps can be, and are preferably automated. While expelling and cleaning steps are generally preferred, no cleaning may be required for polymer characterization applications in which minor sample cross-contamination is acceptable for a rough characterization of the polymer samples. The expelling and one or more cleaning steps can be effected within the preferred sampling cycle times recited above.

Sample preparation steps can also be included in the preferred protocol for sampling a plurality of polymer samples. The sample preparation steps, examples of which are discussed more specifically below, are preferably automated, preferably effected with the auto-sampler, and are preferably effected within the preferred sample cycling times recited above.

Significantly, sample preparation steps (also referred to herein as pretreatment steps) for a plurality of samples are preferably integrated into a rapid-serial sampling approach such that each of the prepared samples is loaded into the polymer characterization system, and subsequently characterized shortly after the sample-preparation steps are completed. In preferred protocols, for example, the prepared samples are injected into a mobile phase of polymer characterization system within not more than about 30 seconds, more preferably not more than about 20 seconds, still more preferably not more than about 10 seconds, even more preferably not more than about 8 seconds, and most preferably not more than about 5 seconds after preparation steps are complete. This approach is unlike typical automated preparation protocols—developed primarily for liquid samples other than the preferred non-biological polymer samples. In known approaches, an entire plurality of liquid samples is typically prepared before any of the plurality of liquid samples is delivered to a characterization system. Although the known conventional approach may be satisfactory for aqueous-based, non-volatile systems, such an approach is generally less preferred for characterizing polymer samples, which may include a volatile liquid-phase component or are worked up with preparation steps that include volatile solvents. If the conventional approaches were applied to a larger plurality (e.g. a number greater than about 8 polymer samples) of polymer samples having a volatile liquid-phase component, the time during which the prepared samples await delivery to the flow characterization system can result in a change in constituent concentrations and, therefore, can effect the comparative basis between detected properties of different polymer samples. As an alternative approach, where parallel sample preparation is necessary or desired and the sample may be stored for some period of time (e.g., more than about 1 hour), it may be desirable to cover the sample containers having the prepared samples to minimize evaporation and protect against contamination (e.g., by dust). Preferably, the containers can be covered with a physically weak, chemically inert barrier such as Teflon™ tape, that can be pierced by the probe for sample withdrawal, thereby allowing neighboring covered samples to remain covered until immediately prior to sampling. As yet another alternative, for samples that may have lost some of the solvent due to evaporation thereof, the solvent can be replenished to a desired level immediately prior to loading of the sample into the characterization system.

Hence, a plurality of polymer samples, especially 8 or more polymer samples, are preferably sampled in a rapid-serial manner by drawing at least a portion of a polymer sample from a sample container into a probe of an auto-sampler, expelling at least a portion of the drawn sample to a sample-preparation container, pretreating the expelled sample in the sample-preparation container to form a pretreated sample, drawing at least a portion of the pretreated sample from the sample-preparation container into the auto-sampler sampler probe, delivering at least a portion of the pretreated sample mixture to a polymer characterization system, and then serially repeating each of the immediately-aforementioned steps for the plurality of polymer samples. In preferred protocols, such steps are effected within the sampling cycle times discussed above. Such rapid-serial withdrawal-preparation-delivery protocols are advantageous over prior art protocols, and as applied to a plurality of polymer samples provide another aspect for improving the sample throughput for a liquid chromatography system 10 or a flow-injection analysis system 20. The preferred rapid-serial withdrawal-preparation-delivery protocol can also optionally include, and will typically preferably include expelling a residual portion of the pretreated sample from the auto-sampler probe, and cleaning the auto-sampler probe after delivering at least a portion of the pretreated sample. The expelling and cleaning can be effected as discussed above.

The particular sample-preparation (pretreatment) steps are not critical, and desired pretreatment protocols are well known in the art. As discussed above in connection with the polymer sample, the pretreating step can comprise diluting the sample, separating one or more components of the sample from other components thereof, and/or mixing the sample. These steps can be, and are preferably, effected with an auto-sampler, for example, as specified in the following exemplary protocols. Variations and other approaches for automated sample preparation will be apparent to a person of skill in the art, and as such, the present invention is not limited by these exemplary protocols. A polymer sample may be diluted with the auto-sampler to a concentration range suitable for detection by combining the expelled sample with a diluting agent (e.g., solvent) in the sample-preparation container. Preliminary, non-chromatographic separation of one or more non-polymer components (e.g., impurities) from a polymer sample may be effected with an auto-sampler as follows. The expelled polymer sample can be combined with a polymer-component-precipitating ("poor") solvent, in the sample-preparation container, whereby polymer components and/or also other components are precipitated, but impurities remain in the liquid phase (poor solvent) within the preparation container. The impurity-containing liquid phase is then removed from the sample-preparation container—for example, by withdrawing the liquid phase into the auto-sampler probe and then discharging the liquid phase into a waste container. Washing steps may then be effected. After washing the probe, if applicable, and optionally filtering or decanting, the auto-sampler probe can be used to deliver a polymer-component-dissolving ("good") solvent to the preparation container, whereby the polymer component and monomer components are redissolved to form a prepared polymer solution. Mixing of a polymer sample (e.g., with an additional component) can likewise be conveniently effected with the auto-sampler in a rapid manner. In one approach, mixing can be effected by inserting the auto-sampler probe into the liquid in the sample-preparation container, removing the auto-sampler probe from the sample-preparation container, and repeating the steps of inserting and removing the auto-sampler probe at least once, and preferably until adequate mixing is achieved. In another auto-sampler mixing approach, the polymer sample can be mixed by withdrawing at least a substantial portion of a liquid phase from the sample-preparation container into the auto-sampler probe, expelling the withdrawn liquid-phase back into the sample-preparation container, and repeating the steps of withdrawing and expelling from and to the sample-preparation container at least once, and preferably until adequate mixing is achieved.

Filters/Pulse-Dampers

As noted above, aspects of sample preparation can also be effected "in-line" within the flow characterization system. Referring again to FIGS. 2A and 2B, for example, non-chromatographic separation can, optionally, be effected with one or more in-line filters 104. The in-line filter 104 can be of any suitable dimensions and mesh size. In one embodiment, a filter 104 can retain particles having a diameter of more than about 0.5 $\mu$m. In another embodiment, a filter 104 can retain particles having a diameter of more than about 0.2 $\mu$m. Other sizes may also be employed, as suitable for a particular polymer sample and/or process application. Additional in-line filters can likewise be employed. While shown in FIGS. 2A and 2B immediately downstream of the injection valve 100, the particular location of the filter is not critical. Moreover, the polymer sample could be filtered as a preparation step, prior to loading of the polymer sample into the flow characterization system. Other in-line systems, such as pulse-dampers can also be employed.

Chromatographic Separation—Chromatographic Column

After injection of a polymer sample into a stream of liquid serving as a mobile phase of a liquid chromatography system, the polymer sample is introduced into a chromatographic column containing a separation medium having a stationary-phase for separation of one or more components of the polymer sample from other components thereof. Separation is effected by selectively eluting one or more of the polymer components from the stationary-phase with a mobile-phase eluant. The degree of separation, also referred to as the resolution of the polymer sample components, can vary depending on the particular chemical nature of the polymer sample components, and the quality of information required in the particular characterization application. In general, the separation performance in a given case can be controlled as a function of the column design/geometry, the stationary-phase media, and the elution conditions with the mobile phase.

The particular design of a chromatographic column for liquid chromatography is, in the general case, not narrowly critical. A number of columns known in the art can be employed in connection with the present invention—as purchased or with minor variations disclosed herein. In general, with reference to FIG. 2A, the chromatographic column 102 of a liquid chromatography system 10 comprises an interior surface defining a pressurizable separation cavity having a defined volume, an inlet port for receiving a mobile phase and for supplying a polymer sample to the separation cavity, and an effluent port for discharging the mobile phase and the polymer sample or separated components thereof from the separation cavity. The separation cavity is preferably pressurizable to pressures typically involved with high-pressure liquid chromatography—such pressures generally ranging from about atmospheric pressure to about 6000 psig (about 40 MPa). In some preferred liquid-chromatography characterization methods, discussed in greater detail below, the chromatographic column can be relatively shorter, and relatively wider, compared to traditional chromatographic separation columns.

The chromatographic column 102 further comprises a separation medium having a stationary-phase within the separation cavity. The separation medium can consist essentially of a stationary-phase or can also include, in addition thereto, an inert support for the stationary phase. The column 102 can also comprise one or more fillers, frits (for separation medium retention and/or for filtering), and various fittings and features appropriate for preparing and/or maintaining the column for its intended application. The particular separation medium to be employed as the stationary-phase is not critical, and will typically depend on the separation strategy for the particular chemistry of the polymer samples of interest, as well as on the desired detection, sample-throughput and/or information quality. Typical stationary-phase media can be a bed of packed beads, rods or other shaped-particles, or a monolithic medium (typically greater than about 5 mm in thickness), each of which can be characterized and optimized for a particular separation strategy with respect to the material, size, shape, pore size, pore size distribution, surface area, solvent regain, bed homogeneity (for packed shaped-particles), inertness, polarity, hydrophobicity, chemical stability, mechanical stability and solvent permeability, among other factors. Generally preferred stationary-phase include porous media (e.g., porous beads, porous monoliths), such as are suitable for gel permeation chromatography (GPC), and media suitable for precipitation-redissolution chromatography, adsorption chromatography, and/or reverse-phase chromatography. Non-porous particles or empty columns and/or capillaries with adsorptive walls can be used as well. If beads are employed, spherical beads are preferred over other shapes. Particularly preferred stationary-phase media for polymer characterization applications are disclosed in greater detail below, but can generally include silica, cross-linked resins, hydroxylated polyglycidyl methacrylates,(e.g., poly(2-3-dihydroxypropylmethacrylate)), poly(hydroxyethyl methacrylate), and polystyrenic polymers such as poly(styrene-divinylbenzene).

The mobile-phase fluid(s) employed to elute one or more polymer components from a chromatographic stationary-phase are not generally critical, and can vary depending on the chemistry of the separation being effected. The mobile phase can be varied with respect to composition, temperature, gradient rates, flow-rates, and other factors affecting selectivity, speed of separation, peak capacity (e.g., maximum number of components that can be separated with a single run) and/or resolution of a polymer component. Exemplary mobile-phase fluids for GPC include tetrahydrofuran (THF), toluene, dimethylformamide, water, aqueous buffers, trichlorobenzene and dichlorobenzene. Exemplary mobile-phase fluids for precipitation-redissolution chromatography include THF, methanol, hexane, acetone, acetonitrile and water. For adsorption chromatography, the mobile phase can include, for example, hexane, isooctane, decane, THF, dichloromethane, chloroform, diethylether and acetone. For reverse-phase chromatography, the mobile phase can include water, acetonitrile, methanol and THF, among others.

Significantly, preferred mobile phase flow rates—for liquid chromatography and/or for flow-injection analysis systems—are typically faster than flowrates employed conventionally for high-pressure liquid chromatography. The flowrates can vary, depending on the separation being effected, but can, in many instances, range from about 0.1 ml/min about 25 ml/min, and preferably range from about 1 ml/min to about 25 ml/min. It may be desirable, for some detector configurations, to split off a part of the sample-containing mobile phase such that the flow rate to a particular detector is reduced to an acceptable level. For liquid chromatography systems, such a split would typically occur after the column and before the detector.

Microprocessors

Referring to FIG. 2A, FIG. 2B and FIG. 4, one or more microprocessors can, as noted above, be employed for controlling every aspect of the flow characterization systems, including: the pump 116 (e.g., mobile-phase flow-rate, flow-rate gradients, compositional gradients, temperature gradients, acceleration rates for such gradients); the reservoir 114 (e.g., temperature, level); the auto-sampler 200 (e.g., movements between spatial position, timing thereof, sample selection, sample preparation, sampling pump flow-rates, and other operations), the injection valve 100 (e.g., timing, selection of sample loops, etc.); the column 102 (e.g., column selection (if multiple columns and automated column-switching valves are present), column temperature); the detector 130 (e.g., data acquisition (e.g., sampling rate), data processing (e.g., correlation); the detector parameters (e.g., wavelength); and/or overall system conditions (e.g., system pressure, temperature). Software is typically available from detector and/or liquid chromatography system manufacturers (e.g., MILLENIUM™ 2000 software available from Waters (Milford, Mass.).

Preferred Liquid Chromatography Protocols

An individual polymer sample is preferably characterized with a liquid chromatography system by withdrawing a polymer sample from a sample container into a probe of an auto-sampler at a first withdrawal time, $t_{ASW1}$. At least a portion of the withdrawn sample is then expelled from the auto-sampler probe into a liquid chromatography system and the loaded sample is injected into the mobile phase thereof. At least one sample component of the injected sample is separated from other sample components thereof in a chromatographic column. At a second detection time, $t_{LCD1}$, a property of at least one of the separated sample components is detected. The characterization protocol can also include pretreating, the withdrawn sample prior to injection, such pretreating comprising sample preparation steps as described. The steps of withdrawing the polymer sample, injecting at least a portion thereof into the mobile phase of the liquid chromatography system, chromatographically separating one or more components of the sample, and detecting a property of the sample or of a component thereof are preferably controlled such that the period of time required to characterize the polymer sample, the liquid-chromatography characterization period, delineated by the difference in time, $t_{LCD1}-t_{ASW1}$, is not more than about 4 minutes. The liquid-chromatography characterization time is preferably less than about 4 minutes, and depending, on the quality of information required, can be less than about 2 minutes, less than about 1 minute, less than about 30 seconds, less than about 20 seconds or less than about 10 seconds. The rapid liquid chromatography protocols of the invention have commercial application with respect to a single, individual polymer sample, for example, in field-based research such as process troubleshooting. As noted, however, substantial commercial applications relate to pluralities of polymer samples.

A plurality of polymer samples is preferably characterized with a liquid chromatography system as follows. A first polymer sample is withdrawn from a first sample container, optionally pretreated in preparation for characterization, and then at least a portion thereof is loaded into an injection valve of the liquid chromatography system. At a first injection time, $t_{LCI1}$, the loaded first sample is injected from the injection valve into a mobile phase of the liquid chromatography system. At least one sample component of the injected first sample is chromatographically separated from other components thereof in a chromatographic column. A property, preferably an optical property, of at least one of the separated sample components of the first sample is then detected. One or more properties of interest (e.g., weight-average molecular weight, composition and/or conversion values) can be determined from the detected property of the first sample or component thereof.

Meanwhile, a second polymer sample is withdrawn from a second sample container. If the same withdrawal instrument is employed, the instrument is preferably cleaned after loading the first sample into the injection valve and before withdrawing the second sample. The second sample is optionally pretreated in preparation for characterization, and at least a portion of the withdrawn second sample is then loaded into the injection valve of the liquid chromatography system. At a second injection time, $t_{LCI2}$, the loaded second sample is injected into the mobile phase of the liquid chromatography system. At least one sample component of the injected second sample is chromatographically separated from other sample components thereof in the chromatographic column, and then a property of at least one of the separated sample components of the second sample is detected. One or more properties of interest (e.g., weight-average molecular weight, composition and/or conversion values) can be determined from the detected property of the second sample or component thereof.

The steps of withdrawing the polymer sample from the sample container, optionally preparing the sample, loading the sample into the injection valve, injection of the sample into the mobile phase, chromatographic separation of the polymer sample and/or detection of a separated sample component are controlled such that the liquid chromatography cycle time, $T_{LC}$, delineated as the difference in between sample injections into the mobile phase of the liquid chromatography system, $t_{LCI2}-t_{LCI1}$, is not more than about 10 minutes. The cycle time is preferably not more than about 8 minutes, and can be, as discussed above depending on the desired quality resolution of the detected property (or of properties of interest determined therefrom), less than about 4 minutes, less than about 2 minutes, less than about 1 minute, less than about 30 seconds, less than about 20 seconds and less than about 10 seconds.

Controlling the efficiency of chromatographic separation is an important aspect of achieving high sample-throughput with acceptable information quality. In general, the column geometry, stationary-phase (e.g.,, permeability, porosity, size, shape, distribution, surface area, surface chemistry), mobile-phase (e.g., eluant composition, eluant temperature, eluant flow rate, gradient profiles for eluant composition, temperature and/or flowrate) are controlled such that the sample-throughput is not more than about 10 minutes per sample. These factors are preferably controlled, individually, in combination with each other, or in combination with other factors, to achieve an average-sample throughput within the times and ranges previously specified. Generally, liquid chromatography relies upon separation based on a particular polymer property (e.g. size) or on a particular polymer composition (e.g., chemistry). Separations to be effected based on size (e.g. hydrodynamic volume) of a polymer sample component can preferably employ GPC media and protocols, somewhat less preferably precipitation-redissolution, and even less preferably reverse-phase (hydrophobic) media or adsorption or normal-phase (hydrophilic) media. Where the separation strategy is to effect a separation based on the particular chemistry of the polymer sample components, the adsorption, normal-phase and reverse-phase chromatography approaches are preferably employed, while precipitation-redissolution approaches are somewhat less preferred and GPC approaches are even less preferred. More than one type of column or separation method may be combined, such as GPC in combination with one of adsorption chromatography, reverse-phase chromatography or precipitation-redissolution chromatography. Such approaches allows simultaneous, rapid separation of polymeric components by size (e.g., $R_h$) and separation of non-polymeric smaller size components by chemistry (e.g., polarity). Because polymer separation occurs, this embodiment allows for measurements of distributions of properties, such as distribution of chemical composition or a distribution of molecular weight for each sample.

Figure 6:
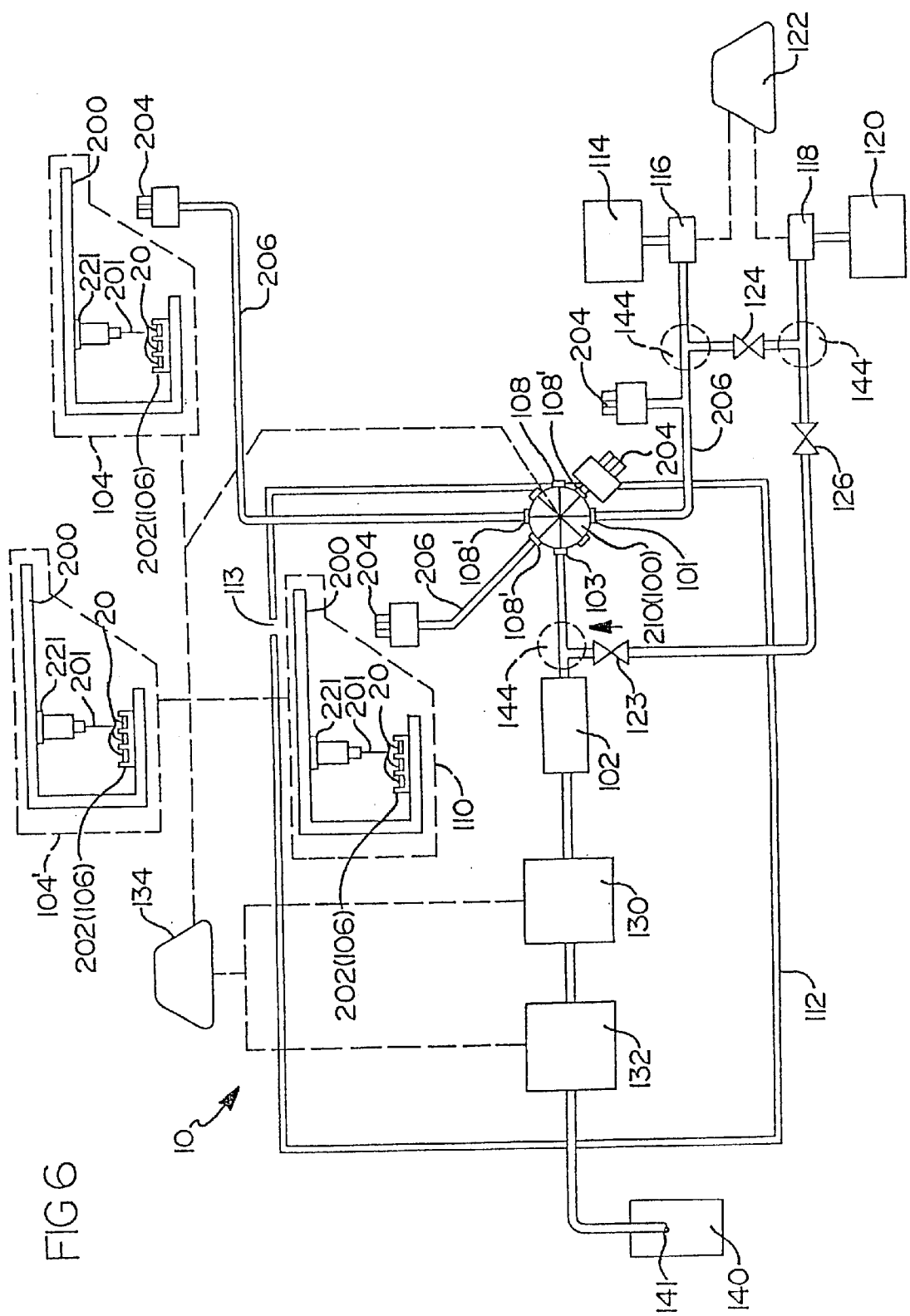
FIG. 6 is a schematic diagram illustrating a preferred embodiment of a liquid chromatography system having high-temperature characterization capabilities.

The particular configuration of the liquid chromatography system used in connection with the present case is not, in the general case, narrowly critical. An exemplary liquid chromatography system is depicted schematically in FIG. 6. Briefly, the liquid chromatography system 10 comprises an injection valve 100, chromatographic column 102, and continuous-flow-through detectors 130, 132. A polymer sample 20 can be loaded into the injection valve 100 from one or more places, either directly via injection ports 108, 108' or indirectly through a loading port 204 and transfer line 206. First, a polymer sample 20 (or a plurality of polymer samples) may be loaded with a robotic auto-sampler 104 that is external to a heated environment (e.g., oven 112) by withdrawing a sample from, for example, a library of samples 106 staged for auto-sampling, and injecting the sample into the loading port 204. A sample can also be loaded into the injection valve 100 through a manual injection port 108. As another alternative, a polymer sample can be loaded into the injection valve by an auto-sampler 110 that is inside (i.e., internal to) the heated environment (e.g., controlled temperature oven 112). One or more mobile-phase fluids (e.g., solvents) can be stored in reservoirs 114, 120 having dedicated pumps 116, 118 that provide the pressure for pumping the mobile-phase fluids through the system 10—including column 102 and detectors 130, 132. The pumps 116, 118 can be controlled by a computer 122. If a mobile-phase temperature gradient is desired, (e.g., in applications discussed below), a colder mobile-phase fluid can be in one reservoir and a hotter mobile-phase fluid can be in another reservoir. For example, a hotter solvent can come from reservoir 114 via pump 116 and the colder solvent can come from reservoir 120 via pump 118. In such cases, valves 124, 126 can be appropriately manipulated—manually or automatically—to open and/or close, preferably allowing for injection of the colder solvent just prior to the column 102. Check valves 123 can also be used for flow control. The solvent can, in this embodiment, remain cold because it will not enter the oven 112 until just prior to injection. After chromatographic separation in column 102, the polymer sample or components thereof may be detected by one or more detectors 130, 132. The detectors can be both internal to the heated environment, as shown in FIG. 6, or alternatively, one or more or all of the detectors can reside externally to the heated environment. The detectors are preferably connected to a computer 134 to collect and process the data obtained from the detectors. In an exemplary configuration, detector 130 can be a light scattering detector and detector 132 can be a refractive index detector or an evaporative mass detector. Following detection, the polymer sample can be exhausted to a waste container 140.

The following protocols can be effectively applied individually, or in combination, and moreover, can find applications with low-, ambient-, or high-temperature characterization protocols.

Column Geometry

In some preferred liquid-chromatography characterization methods, the chromatographic column can be relatively shorter, and relatively wider, compared to traditional chromatographic separation columns. The typical geometry of a conventional column is long and narrow, ranging from about 4–8 mm in diameter and from about 30–50 cm in length, respectively. Typically, three or four columns are employed in series for each separation.

Unlike conventional approaches, preferred liquid chromatographic methods of the present invention can employ columns that are relatively short and wide. More specifically, the chromatographic column can have an aspect ratio ranging from about 0.1 to about 1, where the aspect ratio is defined as the ratio of column-separation-cavity width to the column-separation-cavity height dimensions (e.g., diameter/height—based on a right-cylindrical-shaped separation cavity). In preferred embodiments, the chromatographic column can, for some applications, have an aspect ratio ranging from about 0.3 to about 1, and can also range from about 0.5 to about 1. The actual dimensions for such columns are not critical, but the separation cavity of a column can typically have a hydraulic radius ranging from about 0.1 cm to about 1 cm. For right-handed cylindrical separation cavities, the diameter can range from about 0.5 cm to about 3 cm, and the length can range from about 1 cm to about 7 cm. Preferably, the columns can have diameters ranging from about 0.75 cm to about 2 cm and a length ranging from about 3 cm to about 5 cm.

Reducing the column length while increasing the column width decreases the separation time required for a particular polymer sample. Without being bound by theory, employing relatively shorter columns results in shorter retention times at the same flow rate. Moreover, a reduction in length and an increase in the column diameter results in reduced backpressure, thereby allowing the use of higher mobile-phase flowrates before affecting the structural integrity of the solid-phase media. A limitation to this approach for optimizing the column, however, is the desired resolution of the detected property versus time—which can be given by the number of theoretical plates per the column. Decreased column efficiency in high-speed separations may result in peak broadening—thereby providing less detailed information on distribution of molecular weight (e.g., calculated using GPC calibration). However, the values of the peak-average molecular weights ($M_{peak}$) are relatively unaffected. Reliable values of polydispersity can be then obtained either by mathematical adjustment of data based on the chromatographic broadening of narrow molecular weight standards, or directly by using light-scattering detection. Despite such limitations, the achievable degree of separation of polymer components is, nonetheless, satisfactory for many polymer characterization applications—particularly for screening of combinatorial libraries of polymer components. Hence, such a relatively short and high-aspect ratio chromatographic column provides a further aspect for improving the sample throughput for a liquid chromatography system 10 or a flow-injection analysis system 20.

Chromatographic columns having the above-recited aspect ratios are preferably combined with porous stationary-phase media suitable for gel-permeation chromatography. In one preferred method for characterizing a plurality of polymer samples, the samples are serially injected into a mobile phase of a liquid chromatography system. At least one sample component of the injected samples are separated from other sample components thereof in a chromatographic column having a porous media stationary-phase and an aspect ratio ranging from about 0.1 to about 1. A property of at least one of the separated components of the plurality of samples is detected. When a plurality of samples are to be characterized with such a column, the sample-throughput is preferably as recited above.

Selection of a particular porous media to effect the separation can be guided by the particular sample components being separated. In general, the porous media stationary-phase employed in connection with such method can have a relatively wide range of porosities, such as are obtained with typical "mixed bed" GPC stationary-phase media, and typically expressed by a molecular weight exclusion limit ranging from about 20,000 to well over 10,000,000. Preferred "mixed-bed" stationary-phase media are PLGel Mixed-B and PLGel Mixed-C (Polymer Laboratories).

As an alternative to a single column having a stationary-phase porous media with a range of porosities, two or more of the relatively high-aspect ratio columns can be employed with each column having a more narrow range of porosities. In one such embodiment, for example, two high-aspect ratio columns are arranged in series in the liquid-chromatography mobile-phase flow path. One of the columns can have a porous media with pore sizes of about $10^3$ Å—such pore size being effective for capturing relatively small molecules having a relative molecular weight of up to about 20,000, while allowing molecules larger than about 20,000 to pass through quickly. The other of the columns can have a porous media with pore sizes of about $10^5$ Å—such pore size being effective for capturing and chromatographically separating molecules having a relative molecular weight ranging from about 50,000 to about $2 \times 10^6$. As another example of such rapid size exclusion chromatography, one of the columns can have a porous media with pore sizes of about $10^3$ Å with a second column having a porous media with pore sizes of about 30 Å. (See Ex. 15). Such porous media can be obtained commercially from Polymer Laboratories or Polymer Standard Service, among many others.

In other embodiments, however, the relatively high-aspect ratio columns can be advantageously employed singly with porous stationary-phase media having narrower, more focused porosity ranges. For example, the porous media can be selected to have a porosity selected to effectively separate molecules having molecular weights ranging from about $10^4$ D to about $10^6$ D. Such porous media can be obtained commercially from Polymer Laboratories or Polymer Standard Service, among others. Other narrowly tailored porosity ranges can also be employed with the relatively short, relatively wide column as discussed below in connection with targeted separation.

In other variations, the short column may comprise column stationary-phase packing other than is typically used for GPC, such as normal-phase or reverse-phase silica particles, polymer monoliths, inorganic monoliths, and other well-known column stationary-phase materials or filter media. For example, short columns containing adsorption chromatography stationary-phase can be used to remove components either more polar or less polar than the polymer sample of interest, such as water or solvents initially introduced with the sample. Also in a preferred aspect of this embodiment, more than one short column may be used in series, for example a short GPC column in combination with a short normal-phase adsorption chromatography column, such that polymer is separated from low-molecular-weight components, which are then further separated by polarity. (See Ex. 20). This can be particularly useful for rapidly separating polymer from residual monomer or solvent in a polymerization reaction, and then further quantifying the type and amount of monomer or solvent within a single, rapid analysis.

The detector employed in connection with a polymer characterization method using the relatively high-aspect ratio column is not critical, and can generally include one or more of those detectors previously described. Preferably, a weight-average molecular weight can be determined from one or more detected properties. In preferred configurations, however, the high-aspect ratio geometry columns are combined with the detector configurations described below in connection with rapid-fire light-scattering techniques.

When the liquid chromatography approach involves size exclusion chromatography, such approaches can be referred to as "rapid SEC" approaches. When the size-exclusion separation is effected as gel permeation chromatography, the approaches can be referred to as "rapid GPC" approaches. Generally, optimized column designs for particular polymer sizes of interest can increase the speed of separations of polymer samples (e.g., elution time) substantially compared to typical GPC elution times, which typically require about 40 minutes to an hour. By combining the optimized column designs with the GPC beads, preferably of a specific pore size as discussed below, elution times for polymer sample separation can be reduced, in comparison to typical GPC separations, on the order of 10 times, preferably 20 times and most preferably 40 times. Thus, if typical GPC elution times are in the range of 40 minutes, the elution times of the GPC separations of this invention are less than about 4 minutes, preferably less than about 2 minutes and most preferably less than about 1 minute.

Targeted Separation

In many combinatorial research applications, a target polymer property (e.g., molecular-weight) is predefined. As such, the screening/characterization method can be targeted for sensitivity to the predefined target polymer property. For example, a screen may be designed to determine whether a polymer sample comprises a polymer component within a particular predetermined molecular weight range or particle size range. In such cases, it may not be necessary to measure a precise value for a sample if it outside of the predetermined range.

Such targeted separation protocols can be effectively employed with size exclusion chromatography such as gel permeation chromatography (GPC). Use of targeted-separation GPC techniques—with porosity of the stationary-phase media (e.g. beads) in the column being changed or varied in comparison to standard GPC beads as described herein—is preferably combined with an altered, optimized geometry of the GPC column, again in comparison to standard GPC columns—such as the relatively-high aspect ratio column designs discussed above.

While some aspects of the following description refer to "beads", such reference is to be considered exemplary; other stationary-phase media (e.g., rods, monoliths, etc.) can be readily employed instead of such beads.

With respect to bead porosity, standard GPC columns use beads having nominal pore sizes from several nm up to several hundreds of nm, capable of differentiating between dissolved polymer chains with effective hydrodynamic radii ($R_h$) ranging from about 2 nm up to about 100 nm. Both the pore size of the beads and the effective $R_h$ of the polymer chains is dependent on the chromatographic solvent used, as well as other factors such as temperature and/or ionic strength. In most common cases, columns with mixed porosity beads are used to achieve linear GPC calibrations, requiring a random distribution of differing pore sizes over a broad range of sizes. However, in such a case the resolving ability of the column for polymers with very close molecular weights is limited.

Therefore, one embodiment of this invention uses beads having porosity selected for rapid separation of polymer chains with a smaller range of $R_h$, corresponding to a particular molecular weight range, such as the molecular weight range targeted by the synthesis conditions used to prepare a combinatorial library. For polymers having molecular weights in the range of $10^4$ to $10^5$ beads having porosity from 50 to 100 nm are typically employed. For polymers having molecular weights in the range of $10^3$ to $10^4$ beads having porosity of 10–30 nm are usually employed. Conversely, for polymers having molecular weights in the range of $10^5$ to $10^6$ beads having a porosity of several hundreds of nanometers are employed. The precise pore sizes suitable for separation of macromolecules in certain range of the molecular weights depends also on the structure and solvent interactions of both stationary-phase packing materials and polymer characterized.

Examples of useful porous beads of this invention include: Pl Gel from Polymer Laboratories of various pore sizes; Suprema Gel 30 Å and 1000 Å from Polymer Standard Services (of 3 and 100 nm nominal pore size); and GM-Gel 3000 and 5000 from Kurita (of 380 and 540 nm nominal pore size ). The composition of the beads is cross-linked polystyrene, poly(2,3-dihydroxypropyl methacrylate), and rigid polysaccharide respectively.

Use of the beads of appropriate porosity for separating polymers or particles in particular size ranges allows the use of columns several times shorter than for similar separation obtained using a typical set of conventional GPC columns (such as series of three 30 cm columns). Hence, the combination of targeted-separation stationary-phase media with optimized column geometry is a particularly-preferred embodiment of the invention.

One example of separation using the optimized column geometry and targeted-separation techniques together involves the screening and/or characterization of emulsion polymer particles. Emulsion polymer samples comprising polymer particles having a hydrodynamic radii up to about 200 nm can be separated on a column packed with a macroporous rigid beads via size-exclusion. A property of the polymer samples can be detected with a mass detector (e.g., RI or ELSD/EMD). For such a separation, the column preferably has a length of about 3.0 cm and a width of about 1.0 cm, the stationary-phase porous media packing material has an effective pore size of about 340 nm or 540 nm, and the flow-rate of the mobile phase can range from about 2 ml/min to about 10 ml/min. Effective particle size separation and characterization, with reasonably good quality, is obtained at a rate of about 50 seconds per sample.

Rapid-Fire Light Scattering

Methods involving short, high-aspect ratios columns, with targeted separation medium and one or more light-scattering detectors are referred to herein as "rapid-fire light-scattering" (RFLS) methods.

In one preferred RFLS method for characterizing a plurality of polymer samples, a polymer sample is injected into a mobile phase of a liquid chromatography system, and a low molecular-weight fraction of the injected sample—comprising sample components having molecular weights of not more than about 1000—is separated from a high-molecular weight fraction thereof in a chromatographic column. The high molecular-weight fraction—comprising sample components having molecular weights of more than about 1000 (including substantially all of the polymer component) is allowed to pass through the chromatographic column without substantial separation thereof. A property of the high molecular-weight fraction or of a component thereof is then detected. These steps are then repeated for each of the plurality of polymer samples, in a rapid-serial manner.

In this preferred method, the column preferably comprises a porous stationary-phase phase media having a range of pore sizes that facilitate passage of the high-molecular weight fraction and separation of the low molecular-weight fraction from the high molecular-weight fraction. Moreover, the column preferably has a geometry such as that of the relatively high-aspect ratio columns described above. Specifically, the high-aspect ratio columns are preferably cylindrical with a length of about 1–5 cm and a width (diameter) of about 4 mm to about 1 cm. The column volume ranges from about 0.2 mL to about 4 mL. The flow rate, in this preferred method, is typically faster than for normal chromatographic separation. Preferred mobile-phase flow rates are on the order of 1–40 mL/min, and more preferably from about 1 ml/min to about 25 ml/min. Faster flow rates, combined with relatively small volume of the system, results in a shorter residence time of the polymer sample in the flow system, and therefore, a higher speed of characterization. Polymer properties can be determined for a plurality of samples at an average sample-throughput ranging from about 4 seconds to about 40 seconds per sample. When a polymer sample is measured by this method using a differential refractive index detector and a static light scattering detector, $M_w$ values for multiple polymer samples can be determined at a rate that, compared to a minimum of about 20–40 minutes per sample using typical conventional GPC/light scattering techniques, represents an improvement in throughput of 30–600 times.

This preferred approach can effectively separate polymer components from non-polymeric components of the polymer sample. Hence, the low-molecular weight fraction can include many non-polymeric components, such as dust particles and small molecules, such as solvent, residual catalyst and/or residual monomer. Such separation can improve the accuracy of polymer property determinations, depending on the source and purity of the polymer to be analyzed. In this aspect, this approach is particularly useful for screening a library of polymerization product mixtures from a combinatorial synthesis—where the polymer sample may comprise both polymeric and low-molecular weight components.

The detector configuration employed in connection with RFLS techniques is not critical. Preferred configurations include, briefly: (1) a mass detector (e.g., RI detector, ELSD) combined with a SLS detector to determine the weight-average molecular weight, $M_w$, of the polymer sample—preferably of a polymer solution; (2) a mass detector (e.g., a RI detector, ELSD) combined with a SLS detector to determine particle of a polymer sample—preferably of a polymer dispersion or emulsion; (3) a DLS detector (by itself) to determine the average particle size or a size distribution of a polymer sample—preferably of a polymer dispersion or emulsion, or alternatively, to determine an average molecular weight or a molecular weight distribution of a polymer sample—preferably of a polymer solution; (4) a SLS detector (by itself) at two or more angles (typically, but not necessarily 90° and 15° C.) to determine a weight-average molecular weight; and/or (5) SLS and DLS together to determine the radius of gyration and the hydrodynamic radius, which can be used to provide an indication of branching and higher-order conformation and/or architecture. The high-aspect ratio column can also be employed with other detector configurations, including for example: (1) an RI detector (by itself) with samples of known concentration to determine dn/dC—useful as an indicator for chemical composition; (2) a UV-VIS or photodiode array detector combined with a light scattering and mass detectors—for composition determinations; and/or (3) a viscometric detector in combination with other detectors to provide additional useful information about the sample, such as polymer branching.

Precipitation-Redissolution Chromatography

Precipitation-redissolution chromatography involves the use of mobile phase having a solvent gradient in conjunction with an insoluble stationary-phase (e.g., a polymer monolith). The polymer sample is injected into a mobile-phase solvent that is a "poor" solvent for the polymer being characterized (sometimes called a "non-solvent") thereby causing precipitation of the polymer sample. The precipitated polymer sample then adsorbs onto the stationary-phase (e.g., monolith) surface. Gradually, a better solvent for the polymer being characterized is introduced into the mobile phase. When the better solvent contacts the precipitated polymer sample, the smaller particles of the polymer sample redissolve first. As more of the better solvent contacts the precipitated polymer sample, larger particles of the polymer sample redissolve, until the entire polymer sample has been redissolved. In this fashion, the polymer sample is separated by size (with the smaller particles corresponding to smaller size molecules). Solvent choices depend on the solubility characteristics of the polymer samples being characterized. For a typical hydrophobic polymer such as polystyrene, "good" solvents include tetrahydrofuran, toluene, dichloromethane, etc., while "poor" non-solvents include methanol, ethanol, water, or hexane. It is generally preferred that the good solvent and the poor solvent used for any particular separation be miscible.

The speed of separation of the precipitation-redissolution chromatographic techniques depends on the gradient profiles (e.g., the time rate of change of the mobile-phase composition—between solvent and non-solvent). Typical pump systems supplied by HPLC equipment manufacturers have sufficient speed and accuracy such that the rate of introduction of the better solvent can be controlled to effectively elute the precipitated polymer sample in about 1 minute or less, and in some cases, less than about 45 seconds. Flow rates of the mobile phase are preferably about 5 mL per minute and higher, up to the limit of the pump system used, which can be 20–40 mL per minute for commercial pumps with large-volume pump heads.

Since polymer solubility is also a function of temperature, temperature gradients can also be employed, individually or in combination with the mobile-phase compositional (e.g., solvent) gradient. While this technique is discussed in greater detail below in connection with high-temperature liquid chromatography, the temperature-gradient technique can also have applications at relatively low temperatures—near ambient or below, depending on the particular polymer samples being characterized. Briefly, the sample is introduced at a lower temperature, enhancing precipitation of the polymer, and then the temperature is increased (optionally in conjunction with a change in composition of the mobile phase to a good solvent) to allow selective dissolution and elution of retained polymer.

The precipitation-redissolution chromatography approaches described herein—particularly employing monolithic columns such as those disclosed by Petro et al., vide supra., generally lead to high-speed characterization with good quality of information.

Adsorption Chromatography

Adsorption chromatography using solvents selected for particular polymers or polymer libraries is an alternative method of this invention for rapidly separating polymer samples. In this technique, the polymer sample is reversibly adsorbed from the mobile phase onto the stationary-phase of the column. Adsorption can be enhanced by solvent selection such that the polymer samples have decreased solvency in the chosen "weaker" solvent, as compared to a "stronger" solvent that completely dissolves the polymer samples. As such, the adsorption and/or subsequent desorption can be faster.

The solid-phase media can be selected according to the type of polymer to be analyzed. Exemplary solid-phase media for this approach include porous monoliths and beads.

Silica or hydrophilic polymer beads are used for adsorption of polar polymers or for removing of highly polar components of the samples, such as water, which would otherwise interfere with the analysis of compounds of interest, such as monomers and polymers. Polymeric beads with diol functionalities are preferred for this purpose since they have higher adsorptivity than silica with minimized non-specific interactions with the characterized polymers (See M. Petro, et al., *Anal. Chem.*, 1997, 69 3131; M. Petro, et al., *J. Polym. Sci. A: Polym. Chem.*, 1997, 35, 1173; J. M. J. Fréchet, et. al., *Polym. Mater. Sci. Eng.* 1997, 77, 38.).

The typical mobile phase (e.g., solvent) used for this adsorption chromatography is tetrahydrofuran, either alone or in mixtures with hexane (to enhance adsorption) or water (to enhance elution). Octadecyl-silica beads (commonly used in conventional reverse-phase HPLC) and polystyrene-based monoliths are used for a separation of compounds of medium polarity under the conditions typical of reversed-phase chromatography, usually in combination with a mixture of water and tetrahydrofuran. Optionally, gradients in connection with this technique can be employed, changing either the composition, temperature or flow rate of the mobile phase.

Overlaid Injection/Low-MW Insensitive Detection

Another preferred approach for characterizing a plurality of polymer samples takes advantage of the fact that chromatographic separation is typically a rate-limiting step for liquid chromatography characterization systems. According to this approach, the effective separation time is reduced by serially overlapping samples. Since a given sample is being processed closer in time to the preceding and the successive sample, the overall sample-throughput is improved.

More specifically, a plurality of polymer samples can be characterized by injecting a first polymer sample into a mobile phase of a liquid chromatography system, separating at least one sample component of the injected first sample from other sample components thereof in a chromatographic column, and detecting at least one property of the separated sample component of the first sample. The second polymer sample is then injected into the mobile phase of the liquid chromatography system at a particularly-controlled time, referred to for purposes herein as the successive-sample injection time, $t_{LCI2}$. At least one sample component of the injected second sample is separated from other sample components thereof, and at least one property of the separated sample component of the second sample is detected. The cycle is repeated for each pair of preceding/successive polymer samples in the plurality of polymer samples. In preferred applications, at least 8 different polymer samples are characterized according to the method.

The successive-sample injection time, $t_{LCI2}$, is an important factor in connection with this approach. In general, the particular degree of overlap between successive samples can vary, depending on the desired throughput and information quality. Preferably, the second polymer sample is injected into the mobile phase of the liquid chromatography system at an injection time that provides an average sample-throughput of not more than about 10 minutes per sample for the plurality of samples.

In one approach, the second polymer sample can be injected while detecting at least one property of the separated sample component of the first sample. In another approach, effectively providing a somewhat greater degree of overlap, the second polymer sample can be injected while separating at least one sample component of the injected first sample from other sample components thereof. In a further approach, providing even a greater degree of overlap, the second polymer sample can be injected while advancing the injected first sample to the chromatographic column.

Viewed from another aspect, the second polymer sample can be injected such that the trailing edge of a detection profile for the first sample overlaps with the leading edge of a detection profile for the second sample. That is, the serial injection of polymer samples into the mobile phase can be at a rate that compresses the allowed cycle time so much that the sample components from a first sample and sample components from a successive second sample reside in the detection cavity of the detector simultaneously. In GPC applications, for example, in which stationary-phase is a porous media, the later-eluting smaller-molecule components of the first sample can be present in the detection cavity of the detector at the same time as the earlier-eluting, larger-molecule components of the second sample. An analogous effect can be realized with other chromatographic separation approaches, such as precipitation-redissolution chromatography or adsorption chromatography or reverse-phase chromatography.

In flow-injection analysis approaches, the overlaid samples can be compressed even further. For example, the compression can be such that the samples have overlapped leading and trailing portions or regions, with only a small volume (e.g., sufficient for detection purposes) of pure, non-overlapped sample, available for detection in a detection cavity.

In such overlapped cases, and in particular those cases in which components from a preceding and a successive polymer sample reside in the same detection cavity at the same time, it is advantageous to employ a detector that is insensitive to the sample components from one of the samples. For example, in the exemplary case based on GPC, it is advantageous to employ a detector that is insensitive to sample components having low molecular weights—corresponding to the later-eluting sample components of the first (preceding) polymer sample. Preferably, a detector is employed that is insensitive to sample components having a weight-average molecular weight of less than about 1000. The detector can, most preferably, be an evaporative light-scattering detector (ELSD).

The overlaid-injection approach described herein allows for substantial improvements in sample throughput. For example, complete molecular weight information (including PDI) and composition for a plurality of samples can be obtained—with a level of quality comparable to conventional GPC—using an "accelerated size exclusion chromatography" approach that incorporates this technique. (See Ex. 17 and Ex. 18). This approach is suitable for determining a characterizing property of interest, evaluating monomodality versus polymodality, and evaluating purity with a sample throughput of not more than about 8 minutes per sample. In another application of the overlaid-injection approach, average molecular weights and molecular weight distribution information can be obtained—with a level of quality that is reasonably good—using a "rapid size exclusion chromatography with enhanced resolution" approach. (See Ex. 16).

Preferred Flow-Injection Analysis Protocols

A plurality of polymer samples are characterized according to the present invention with a flow-injection analysis system by serially injecting a plurality of polymer samples into a mobile phase of a continuous-flow detector, and detecting a property of the injected samples or of components thereof with the continuous-flow detector—preferably at an average sample-throughput of not more than about 10 minutes per sample. In some embodiments, two or more continuous-flow detectors are used in series. The combination of two or more detectors allows for the determination of certain polymer attributes of interest. Because no substantial chromatographic separation of the polymeric components of the sample occurs, flow-injection analysis allows for measurement of properties of a heterogeneous polymer sample, such as average properties (e.g., average composition or average molecular weight) or, with some detectors (e.g., dynamic light-scattering detectors) specific component properties. This embodiment may be particularly rapid, limited only by the speed of the sampling or by the residence time of the liquid in the flow system. This embodiment is particularly useful for rapid screening of combinatorial polymerization reactions, especially to determine polymerization conditions or characteristics.

In a preferred approach, a plurality of polymer samples are characterized with a flow-injection analysis system as follows. A first polymer sample is withdrawn from a first sample container, preferably into a probe of an auto-sampler. At a first injection time, $t_{FI1}$, at least a portion of the withdrawn first sample is injected into the mobile phase of the continuous-flow detector, and advanced toward a detection-cavity of a detector—without substantial chromatographic separation thereof. A property of the injected first sample or of a component thereof is detected while the sample resides in the detection cavity of the detector. A second polymer sample is withdrawn from a second sample container. At a second injection time, $t_{FI2}$, at least a portion of the withdrawn second sample is injected into the mobile phase of the continuous-flow detector. A property of the injected second sample is detected.

In general, the steps of withdrawing the polymer samples, injecting at least a portion of the withdrawn polymer samples into the mobile phase of a flow-through detector, advancing the injected samples toward the detection cavity of the detector, and detecting a property of the injected samples are controlled such that the flow-injection cycle time, $T_{FI}$, delineated by the difference in time, $t_{FI2}-t_{FI1}$, is not more than about 10 minutes. Hence, the speed of detection is limited, in a practical sense, by sampling rates, mobile phase flow rate in the flow-injection analysis system, and required sample residence time in the continuous-flow detector. In preferred embodiments, the flow-injection time is not more than about 8 minutes, and preferably less than 4 minutes, less than 2 minutes, less than 1 minute or less than 30 seconds. Flow-injection cycle times of less than 20 seconds, and less than 10 seconds can also be achieved.

Figure 7A:
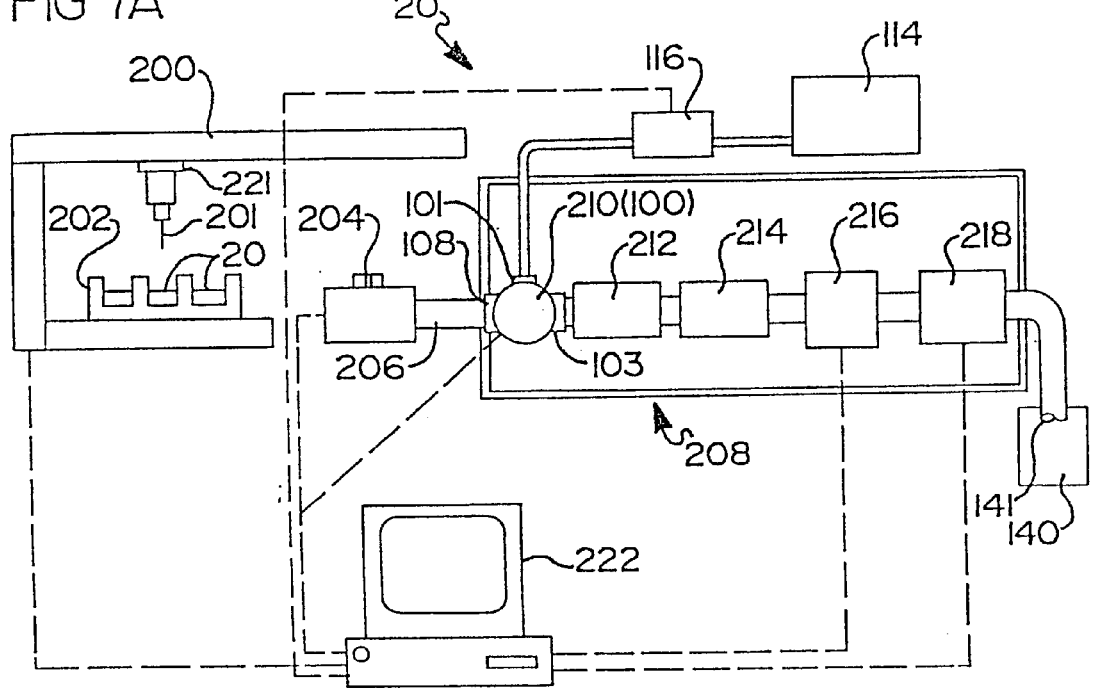
FIG. 7A through FIG. 7D relate to preferred liquid chromatography and flow-injection analysis systems and/or operational aspects thereof.
Figure 7B:
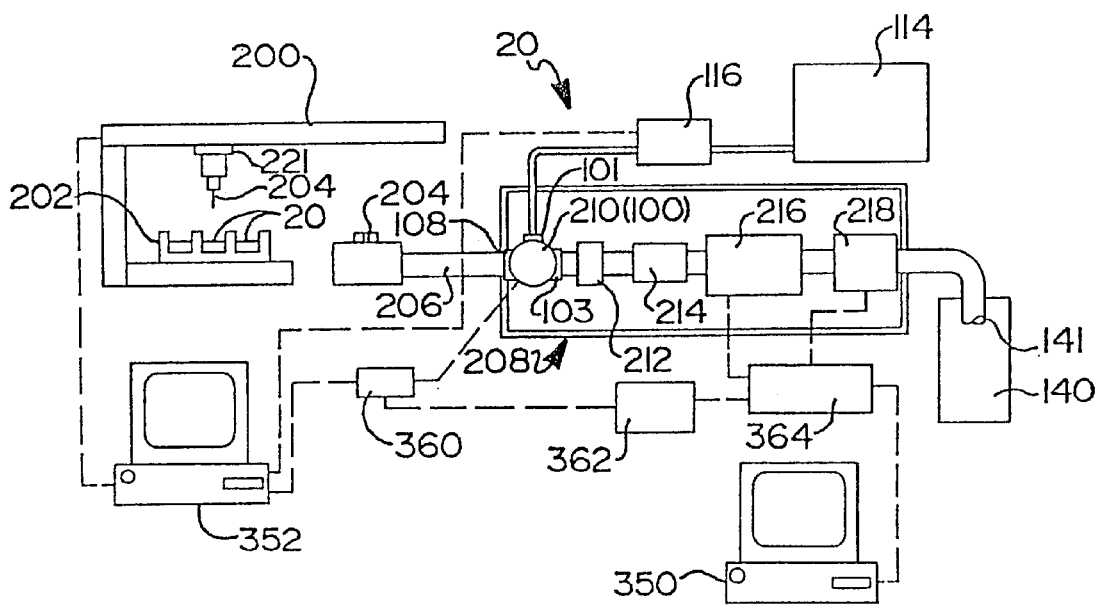

FIGS. 7A and 7B show a preferred configuration for a flow-injection analysis system 20. An auto-sampler 200 (described in connection with FIG. 4) withdraws a sample 20 from a sample container 202 into an injection probe 201. A mobile phase is supplied to the system 20 from reservoir 114 via pump 116. The polymer sample 20 is injected into the mobile phase—either directly (not shown) or indirectly via loading port 204, and is advanced through sample transfer line 206 to valve 210. Valve 210 is preferably an injection valve 100 having an injection port 108. After optionally passing through in-line filter 212, the sample is detected in one or more continuous-flow detectors 216, 218 (e.g., a light-scattering detector and/or a concentration detector). Optionally, the flow-injection system can be used as a rapid liquid-chromatography system by including a high-aspect ratio column 214. The valve 210, filter 212, column 214 (if included) and detectors 206, 218 can optionally be housed within a temperature-controlled environment (e.g., oven 208). The sample is discharged to a waste container 140.

A single microprocessor (e.g., computer 222) (FIG. 7A) can control the entire system 20—including sampling with the auto-sampler 200, injecting of samples into the mobile phase via loading port 204, mobile-phase fluid flow via pump 116, and receiving and processing the data from the detectors 216, 218. In an alternative configuration shown in FIG. 7B, the system 20 can be controlled with two microprocessors (e.g., computers 350, 352)—enabling high-throughput rapid-serial detection. The robotic auto-sampler 200 and data acquisition from detectors 216, 218 can be controlled with the two different computers 350, 252 synchronized via a trigger pulse. More specifically, computer 352 can control the robotic auto-sampler 200, mobile-phase pump 116, and injection valve 210. A serial port on the computer 352 can be connected to a valve controller 360, which in turn can be connected to the injection valve 210. The valve controller 360 can also be connected to a pulse widening circuit 362 via a digital logic circuit (using a pulsed contact closure). The valve controller 360 can also allow for manual (e.g., push button) operation of the valve 210, using the same digital logic circuit. The pulse widening circuit 362 can be connected to a data acquisition module 364 standard for chromatographic analysis. The data acquisition module 364 can be connected to the second computer 350. In operation, the valve controller 360 sends a pulse signal to the data acquisition module 364 indicating that a sample has been injected in to the system 20, causing computer 350 to begin acquiring data from, for example, a lighting-scattering detector 216 and a refractive-index detector 218 via the data acquisition module 364. The computer 352 can include a time variable appropriate for the characterization method being employed to space the injection of samples according a predetermined interval. If a new injection pulse is sent from computer 352, computer 350 can initiate new acquisition of data for the next sample and discontinues data acquisition for the existing sample. A similar control configuration can be effected for liquid chromatography systems.

The following protocols can be effectively applied individually, or in combination, and moreover, can find applications with low-, ambient-, or high-temperature characterization protocols. Although such protocols are primarily described with respect to polymer samples, and although such polymer samples are preferred samples for the flow-injection analysis protocols disclosed herein, non-polymer samples can also be employed in some applications (e.g., pigment characterization, etc.).

Flow-Injection Light-Scattering

Light-scattering detectors (SLS, DLS, ELSD) can be advantageously applied in flow-injection analysis applications—alone or in combination with other light-scattering detectors or other, non-light-scattering detectors. High-throughput flow-characterization methods using at least one light-scattering technique can be referred to as "flow-injection light-scattering" ("FILS").

A number of flow-injection light-scattering approaches have been developed for rapidly screening polymer samples without chromatographic separation thereof. Each of the approaches can be employed to determine polymer properties that include average molecular weight of polymer samples (e.g., dissolved polymer samples) or average particle sizes of polymer samples (e.g., emulsified or dispersed polymer samples), as well as non-averaged properties of interest. In a first method, a mass detector, such as an RI detector or an ELSD, is combined with a SLS detector to determine the weight-average molecular weight, $M_w$, of the polymer sample—preferably of a polymer solution. In a second method, a mass detector (e.g., a RI detector or an ELSD) is combined with a SLS detector to determine particle size (e.g., volume-averaged particle diameter) of a polymer sample—preferably of a polymer dispersion or emulsion. In a third approach, a DLS detector can be used by itself to determine an average particle size or a size distribution of a polymer sample—preferably of a polymer dispersion or emulsion, or alternatively, to determine a weight-average molecular weight or a molecular weight distribution (shape and estimate of PDI) of a polymer sample—preferably of a polymer solution. According to a fourth approach, a SLS detector can be used by itself at two or more angles (typically, but not necessarily 90° and 15° C.) to determine the radius of gyration. In yet another approach, a SLS and DLS can be employed together to determine the radius of gyration and the hydrodynamic radius, which can be used to provide an indication of branching and higher-order conformation and/or architecture.

Some flow-injection embodiments employ other detectors—without light-scattering detectors. For example, in one method, dn/dC—the relationship of refractive index and concentration of the polymer sample—can be determined without chromatographic separation of polymer components, by measuring the response of a RI detector for samples of known concentration. This relationship can be effectively used, for example, as an indicator of chemical composition of the polymer. Alternatively, in a FILS technique, more detailed information about the chemical composition of analytes can be obtained using UV-VIS or photodiode array detector in a series with the light scattering and mass detectors. Inclusion of a viscometric detector can provide additional useful information about the sample, such as polymer branching.

Generally, FILS allows for the detection of both homogeneous and heterogeneous samples. FILS is optionally, and generally preferably, combined with sample pretreatment as discussed, including for example, various on-line pretreatment techniques such non-chromatographic separation techniques with filters.

As noted above, the detector configurations employed with the above-discussed FILS techniques can, in preferred embodiments, be advantageously employed in combination with a very quick chromatographic separations using the relatively high-aspect ratio column geometries and/or targeted-separation approaches described above. Quick chromatographic separation for macromolecule or particle size separation or for separating high-molecular weight (large) particles or molecules from low-molecular weight (small compounds) are preferred in combination with the FILS detector configurations. The speed of characterization methods of the invention that use capillaries, columns, and cartridges of low volumes of 0.1–1 mL and high flow rates upwards of 20 mL/min can be less than 10 seconds per sample, or less than 5 seconds per sample, and approach 1–3 seconds per sample.

The nature of the polymer samples and analysis technique will influence whether a short column, filter, or pulse damper is employed. For example, an array of solutions comprising pure polymers with no significant presence of large particulates or small molecules can be rapidly characterized for $M_w$ by the FILS methods of this invention, using an RI and SLS detector, without a chromatographic column and in some cases, also without a filter.

FILS can also be combined with variable-flow injection analysis techniques (discussed below) with or without separation or other pretreatment.

Variable Flow Light-Scattering

In another preferred approach, the flow-rate of the mobile phase is controlled such that an injected polymer sample is rapidly advanced to and/or rapidly passed away from the detection cavity of a flow-through detector, and such that the polymer sample is slowed or stopped while the sample resides in the detection cavity of a light-scattering detector. In such variable-flow (also referred to as "stop-and-go") techniques, the polymer sample remains slowed or stopped during a period of time sufficient for detection/characterization. This approach can have a significant impact on the injection-to-detection run time for a single polymer sample, and the effect is particularly substantial for characterizing a plurality of samples.

When the variable-flow light-scattering protocols are applied to a plurality of polymer samples, such as a library of polymer samples, the average sample-throughput can be greatly improved over constant-flow light-scattering systems. More particularly, a plurality of polymer samples can be characterized by serially injecting a plurality of polymer samples into a mobile phase of a continuous-flow light-scattering detector, advancing the injected samples toward a detection cavity of the detector, detecting light scattered from the injected samples or from a component thereof in the detection cavity, flushing the samples from the detection cavity after detecting the scattered light, passing the flushed sample away from the detection cavity, and controlling the flow-rates of the samples during the steps of injecting, advancing, detecting, flushing and/or passing such that the average sample throughput is not more than about 10 minutes per sample, preferably not more than about 4 minutes per sample, more preferably not more than about 2 minutes per sample, and most preferably not more than about 1 minute per sample. In some applications, the average sample throughput can be preferably not more than about 50 seconds per sample, more preferably not more than about 40 seconds per sample, even more preferably not more than about 30 seconds per sample, more preferably yet less than about 20 seconds per sample and most preferably less than about 10 seconds per sample.

Although the flow of the mobile phase can be temporarily stopped according to one or more variations of this method, the methods, and the flow-injection systems and detectors employed are considered, nonetheless, to be continuous-flow systems and detectors. Moreover, while this variable-flow light-scattering detection approach has primary applications with respect to a flow-injection analysis system, an analogous approach can be applied in connection with liquid-chromatography systems, with accommodations made, for example, for maintaining an appropriate, typically constant flow-rate through the chromatographic column.

According to one variation of the method, a polymer sample is rapidly advanced to the detection cavity of a light-scattering detector, and then slowed or stopped for detection therein. Such a variation will be referred to herein as a rapid-advance, slow-detect approach. More specifically, a polymer sample can be characterized by injecting a polymer sample into a mobile phase of a continuous-flow light-scattering detector, and advancing the injected sample is advanced toward a detection cavity of a light-scattering detector. The sample-containing mobile phase has a advancing flowrate, $V_{ADVANCE}$, while the injected sample is advanced toward the detection cavity. The flowrate of the sample-containing mobile phase is subsequently reduced to a relatively lower detection flowrate, $V_{DETECT}$. The light scattered from the injected sample or from a component thereof is detected in the detection cavity of the detector while the mobile-phase flowrate is reduced to the detection flowrate, $V_{DETECT}$. The sample is then flushed from the detection cavity after the scattered light is detected.

Following detection, the polymer sample can be passed away from the detection cavity at the same slower detection rate or, alternatively and preferably, at an increased rate. That is, the rapid-advance, slow-detect approach can be followed by either a slow-pass, or a rapid-pass approach. Preferably, the overall approach is a rapid-advance, slow-detect, rapid-pass approach. More specifically, the flowrate of the sample-containing mobile phase is increased to a passing flowrate, $V_{PASS}$, after detecting the scattered light, and the flushed sample is passed away from the detection cavity of the light-scattering detector at the passing flowrate, $V_{PASS}$. Preferably, the passing flowrate, $V_{PASS}$, can be substantially the same as the advancing flowrate, $V_{ADVANCE}$ (accounting for normal variations in flow-control capabilities).

In an alternative variation of the method, an injected polymer sample is detected in a detection cavity of a light-scattering detector at a relatively slow flow-rate (or while stopped), and then rapidly passed away from the detection cavity. Such a slow-detect, rapid-pass variation is more specifically described as follows. A polymer sample is characterized by injecting the polymer sample into a mobile phase of a continuous-flow light-scattering detector. Light scattered from the injected sample or from a component thereof is detected in a detection cavity of the detector. The sample-containing mobile phase has a detection flowrate, $V_{DETECT}$, while the scattered light is detected. The sample is flushed from the detection cavity after detecting the scattered light. The flowrate of the sample-containing mobile phase is increased to a higher passing flowrate, $V_{PASS}$, after detecting the scattered light, and the flushed sample is passed away from the detection cavity of the detector at the increased higher passing flowrate, $V_{PASS}$. The flow-rate of the mobile phase while the sample is being advanced can be relatively slow, or fast, such that the overall approach is slow-advance, slow-detect, rapid-pass, or rapid-advance, slow-detect, rapid-pass.

Hence, in a most preferred approach, a plurality of polymer samples are characterized by withdrawing a polymer sample from a sample container. The withdrawn polymer sample is injected into a mobile phase of a continuous-flow light-scattering detector while the mobile phase has a advancing flowrate, $V_{ADVANCE}$. The injected first sample is advanced toward a detection cavity of the detector while maintaining the flowrate of the mobile phase at the advancing flowrate, $V_{ADVANCE}$. The flowrate of the mobile phase is then reduced to a detection flowrate, $V_{DETECT}$. Light scattered from sample or from a component thereof is detected in the detection cavity of the detector while the mobile phase flowrate is at the reduced detection flowrate, $V_{DETECT}$. The first sample is flushed from the detection cavity after detecting the scattered light, and the flowrate of the mobile phase is increased to the advancing flowrate, $V_{ADVANCE}$, after detecting the scattered light. The flushed sample is passed away from the detection cavity of the detector while maintaining the flowrate of the mobile phase at the advancing flowrate, $V_{ADVANCE}$. The aforementioned steps can then be repeated for a plurality of polymer samples.

For any of the above protocols, when a plurality of polymer samples are being characterized with a variable-flow light-scattering approach, the timing of injection of a successive (e.g., second) polymer sample can vary relative to the position of the preceding (e.g., first) polymer sample. More specifically, a second polymer (successive) sample can be injected into the mobile phase of the continuous-flow light-scattering detector at various times after the first (preceding) sample has been injected. In one variation, the second polymer sample is injected while the first polymer sample is being passed away from the detection cavity of the light-scattering detector. In another variation, the second polymer sample is injected while the light scattered from the first polymer sample is detected (that is, while the first polymer sample resides in the detection cavity). In yet a different variation, the second polymer sample is injected while the first polymer sample is advanced toward the detection cavity of the light-scattering detector. The preferred approach with respect to the timing of the injection of a second, successive sample in a plurality of polymer samples can vary—particularly depending on the sample size, the sustainable sampling throughput, and the actual flow-rates of the mobile phase—for advancing flow-rates, detection flow-rates, passing flowrates, and/or higher flow-rates.

The polymer sample is not narrowly critical and can, in general, be a polymer sample as described above. Preferred applications of the variable-flow light-scattering detection protocol include polymer samples comprising a polymer component having a particle that has diffusional mobility in the system mobile phase. Typical particle sizes (diameters) range, in typical mobile-phase solvents, from about 1 nm to about 500 nm and preferably from about 5 nm to about 300 nm. These ranges of particle size could be extended by changing the viscosity of the mobile phase, for DLS-detected systems, since DLS measures diffusion. The concentration of the polymer sample can generally be the same as described above, except that the lower limits may be extended to as low as detectably possible—sufficient to scatter a light signal.

The ratio of flow-rates and the actual flow-rates employed in connection with any variation of this approach are not critical. In general, however, advancing flowrate, $V_{ADVANCE}$, is greater than the detection flowrate, $V_{DETECT}$, by a factor of at least about two, more preferably by a factor of at least about five, and even more preferably by a factor of at least about ten. The advancing flowrate, $V_{ADVANCE}$, can range, for example, from about 1 ml/min to about 25 ml/min, preferably from about 1 ml/min to about 10 ml/min, more preferably from about 1 ml/min to about 5 ml/min and even more preferably, from about 1 ml to about 3 ml. The first flowrate is most preferably about 1.5 ml/min. The detection flowrate, $V_{DETECT}$, can range from about zero to about 1 ml/min, and preferably ranges from about 0.1 ml/min to about 0.5 ml/min, and more preferably, from about 0.1 ml/min to about 0.3 ml/min.

The continuous-flow light-scattering detector can be a static-light-scattering (SLS) detector or a dynamic-light-scattering DLS detector. In preferred embodiments, both a SLS detector and a DLS detector can be employed, with the SLS being used primarily for flow-control purposes, and the DLS detector data being used for determining a characterization property of interest (e.g., weight-average molecular weight, particle size distribution, molecular weight distribution or other property derivable from the distribution of the diffusion constant). For flow-injection analysis systems having a DLS detector, the detection flowrate is preferably a constant flowrate during the period of time when the polymer sample or a component thereof is detected. For systems having a DLS detector or a SLS detector, the flow through the detection cavity is preferably non-turbulent.

Control of the flowrates can be effected by a number of different control schemes. According to one control approach, the advancing flowrate, $V_{ADVANCE}$, is reduced to the detection flowrate, $V_{DETECT}$, when a leading edge of the polymer sample enters the detection cavity of the light-scattering detector. The detection flowrate, $V_{DETECT}$, is then maintained for a detecting period of time ranging from about 1 second to about 60 seconds or for a period of time ranging from about 3 seconds to about 40 seconds. The detecting period more preferably ranges from about 5 seconds to about 20 seconds, even more preferably from about 7 seconds to about 15 seconds, and most preferably from about 10 seconds to about 12 seconds. As noted, the leading edge can be detected with a static-light scattering detector or a dynamic light-scattering detector signal that causes a change in a detector output signal (e.g., scattered-light intensity, voltage), thereby indicating the presence of the polymer sample in the detection cavity. The leading edge can also be detected with other detectors, such as an ELSD, or RI detector. The aforedescribed control approach is represented schematically in FIG. 7D. (See also Ex. 24). In an alternative control scheme, the timing for lowering the flowrate from the advancing flowrate to the lower detection flowrate can be based entirely on system mechanics: primarily flow-rates and residence times in the flow path. The detecting period is preferably sufficient to obtain scientifically meaningful data. The flush-out period can be a predetermined period (e.g., from about 5 seconds to about 10 seconds) or can be controlled based on detector output, results, etc.

In one configuration, a continuous-flow light-scattering detection system for effecting the variable-flow light-scattering protocols comprises, with reference to FIG. 2B, an injection valve 100 having an injection port 108, optionally a loading port 204 (FIG. 7) in fluid communication with the injection port 108 via a transfer line 206 (FIG. 7), for injecting a sample into the mobile phase. The system 20 also comprises a light-scattering detector 130 having a detection cavity 131. The detection cavity 131 has an inlet port and an outlet port through which a sample-containing mobile phase can flow. A mobile-phase fluid source (e.g., reservoir 114) is in fluid communication with the inlet port of the detection cavity, and a pump 116 provides the motive force for flow of the mobile phase from the source to the detection cavity 130. The system 20 further comprises, a detector (not shown) for indicating the position of an injected sample relative to the detection cavity, and a flow-control element (not shown) for controlling the flowrate of the mobile phase. A flow-controller is preferably in communication with the detector and with the flow-control element. Flow can be initiated by a pump or by the auto-sampler, optionally using an injection valve 100 (valve 210) similar to that described above in FIG. 3. In the embodiments that use a pump, the pump would be connected to the valve at the inlet port 101. If no pump is used, the inlet port 101 is plugged and the liquid medium is provided by the sampler through the loading port 204, preferably with volume control of the injected sample.

High-Temperature Characterization

A number of commercially important polymers are preferably characterized at temperatures above room temperature. For example, polymers that are insoluble at room temperatures, but soluble at higher temperatures in a particular solvent, can be conveniently characterized at such higher temperatures. Exemplary polymers that can be characterized at temperatures above about 75° C. include aqueous-associated or physically-gelling polymers (e.g., gelatin, polyvinyl alcohols). Some polymers are preferably characterized at even higher temperatures—above about 125° C., including for example, polyethylene (typically about 130° C.), polypropylene (typically about 150° C.) and polyphenylenesulfide (typically about 200° C.).

Accordingly, a number of methods, systems and devices have been developed to effect high-temperature characterization of single polymer samples and/or of a plurality of polymer samples. As used herein, the term "high-temperature characterization" refers to characterization of a polymer sample at temperatures that are above about 75° C. and typically ranging from about 75° C. to about 225° C., or higher temperatures—limited by the integrity of the separation medium and mobile phase at such higher temperatures. For many commercially-important polymers, high-temperature characterization can be effected at temperatures ranging from about 100° C. to about 200° C., or from about 125° C. to about 175° C. Methods, systems and devices are discussed below that relate to improved aspects of polymer sampling, chromatographic separation and detection for high-temperature characterization. Those methods, systems and devices that are directed to polymer sampling or detection will have applications for flow characterization systems generally (i.e., for both liquid chromatography systems and flow-injection analysis). Moreover, while the approaches discussed below are advantageous in connection with high-temperature characterization, some of the approaches have applications outside of high-temperature characterization, and, therefore, should not be categorically limited to high-temperature applications unless specifically required by the claims. Likewise, while some of the approaches are described in connection with characterizing a single polymer, they can be and for many applications are preferably, likewise applicable to characterizing a plurality of polymer samples.

Auto-Sampling with an External, Heated Injection Probe

Automated sampling of polymer samples for high-temperature characterization is preferably effected with an auto-sampler having a heated injection probe (tip). With reference to FIG. 4 and to FIGS. 5A through 5C, such an auto-sampler can comprise a probe 201 mounted on a support arm 203, a microprocessor 222 for controlling three-dimensional motion of the probe between various spatial addresses, and a pump (not shown) for withdrawing a polymer sample into the probe. The probe 201 has a surface defining a sample-cavity 2014 and a sampling port 2016 for fluid communication between the sample cavity 2014 and a polymer sample 20. The probe also preferably comprises a solvent port 2015 for fluid communication between a solvent supply reservoir and line (not shown) and the sample cavity 2014. The probe 201 is adapted for fluid communication with an injection port 108 or a loading port 204 of a continuous-flow polymer characterization system.

Figure 5C:
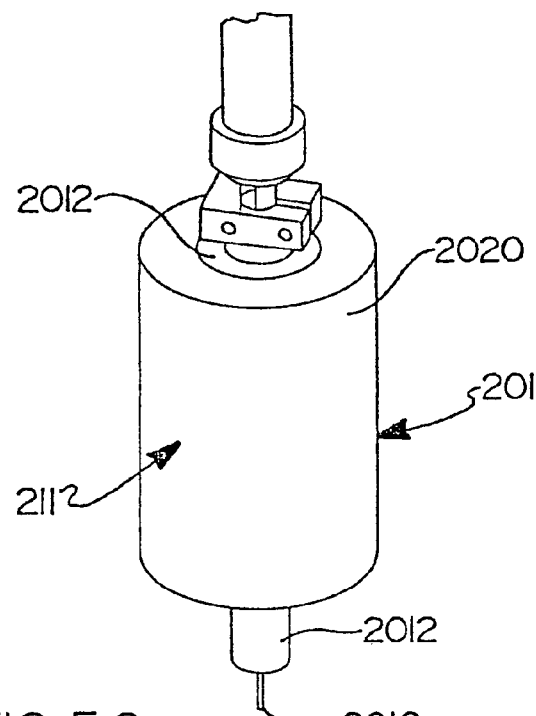

Significantly, the auto-sampler further comprises a temperature-control element 211 in thermal communication with the auto-sampler probe 201 for maintaining a drawn polymer sample residing in the probe at a predetermined temperature or within a predetermined range of temperatures—preferably a temperature of not less than about 75° C., or if necessary, not less than about 100° C. or not less than about 125° C. The temperature-control element 211 can be, in the general case, a heating element or a cooling element (for low-temperature characterizations). The particular design of the heating element or cooling element is not critical. With reference to FIGS. 5A through 5B, the heating element 211 can be, for example, a resistive-heating element such as a resistive wire 213 in adjacent proximity to the sample cavity 2014 of the probe 201 (FIG. 5A). The heating element 211 can alternatively be a fluid-type heat-exchanger heating element having a fluid-containing tubular coil 215 around the probe 201 (FIG. 5B). In any case, the temperature-controlled probe 201 can have a body 2012 encasing the heating element 211, and preferably a thermocouple 2018 for temperature monitoring and control. In another alternative embodiment, with reference to FIG. 5C, the heating element 211 can be the body 2012 of the probe itself, where the body 2012 comprises a large thermal mass, preferably surrounded by an insulator 2020. The large-thermal-mass body 2012 can be heated (or in the general case, cooled) by periodically allowing the body to thermally equilibrate with a hot environment such as a surface or fluid via conduction, convection or thermal radiation (or generally, with an cold environment).

Advantageously, such a heated probe can maintain the sample at the required temperature while the sample resides in the sample-cavity of the probe. As such, unlike conventional high-temperature characterization systems, the auto-sampler probe, as well as associated robotic support arm, can be located external to (outside of) a heated environment (e.g., oven).

Hence, referring to FIG. 6, a polymer sample 20 can be characterized by withdrawing a polymer sample from a sample container into a heated auto-sampler injection probe 201. The heated probe 201 and, typically, the sample container (e.g., a library of polymer samples 106) are resident in a first environment maintained at about ambient temperature—external to a heated second environment (e.g., oven 112) maintained at a temperature of not less than about 75° C., in which other components (e.g., chromatographic column 102) of the chromatographic system 10 reside. The polymer sample 20 is maintained, generally, at a temperature of not less than about 75° C. during a period of time including from when the sample is withdrawn from the sample container to when the sample is within the heated second environment. In some applications, such as for flow-injection analysis, the sample is preferably maintained at a temperature of not less than about 75° C. during a period of time including from when the sample is withdrawn from the sample container to when the property of the sample or of a component thereof is detected. More specifically, the sample container, if external to the second heated environment, is preferably heated to maintain the polymer sample at a temperature of not less than about 75° C. while the sample is resident in the container. The injection probe is likewise heated to maintain the withdrawn sample at a temperature of not less than about 75° C. while the sample is resident in the probe 201. A preparation station comprising one or more preparation containers can also be heated to the required high-temperatures.

At least a portion of the withdrawn, high-temperature sample is loaded into an injection port 108 of a flow characterization system (e.g., a liquid chromatography system or a flow-injection analysis system), either directly or through a loading port 204 and a transfer line 206. The injection port is adaptable for fluid communication with a downstream elements (e.g., chromatographic column 102 and/or continuous-flow detector 230), and can reside internal to or external to the heated second environment. If the injection port resides external to the heated second environment—in the first, near-ambient environment—the injected sample is preferably advanced (e.g., toward the chromatographic column) through a transfer line providing fluid communication between the injection port and the chromatographic column and/or detector 230 while heating the transfer line to maintain the injected sample at a temperature of not less than about 75° C. while resident in the transfer line. In a preferred sample loading configuration, a sample can be loaded with an external auto-sampler 104' by inserting the probe 201 of the auto-sampler 104' through an aperture 113 in the heated-environment enclosure (e.g., oven 112) and into a loading port 204 within the heated environment. In such a configuration, the probe 201 can be sufficiently long to reach into the loading port 204 within the heated environment. The loaded sample is, in any case, injected into a mobile phase of the flow characterization system. If the flow characterization system is a liquid chromatography system 10, the sample is chromatographically separated. If the flow characterization system is a flow-injection analysis system, the sample is optionally filtered. In any case, a property of the sample or of a component thereof is then detected with one or more detectors 130, 132.

For polymer samples being characterized at even higher temperatures, the injection probe can be heated to maintain the withdrawn sample at a temperature of not less than about 100° C., or if necessary, not less than about 125° C., while resident in the injection probe. The heated second environment can be maintained at a temperature of not less than about 100° C., or, if necessary, not less than about 125° C. The sample is, in such cases, respectively maintained at a temperature of not less than about 100° C., or if necessary, not less than about 125° C., during the period of time including from when the sample is withdrawn from the sample container to when the sample is injected into the portion of the flow characterization system (e.g., liquid chromatography system) residing in the heated second environment.

Rapidly Heated/Cooled Column and System

According to another high-temperature characterization protocol, a polymer sample can be characterized in a liquid chromatography system that is readily adapted to high-temperature characterization protocols. Specifically, a chromatographic column is prepared for separation by heating the column from about ambient temperature to about 75° C. in less than about 1 hour. A polymer sample is injected into the mobile phase of the liquid chromatography system and loaded onto the heated column. At least one sample component of the polymer sample is chromatographically separated from other sample components thereof in the heated chromatographic column, and a property of at least one of the separated sample components is then detected.

If necessary for a particular application, the chromatographic column can be heated from about ambient temperature to about 100° C., or alternatively, to about 125° C. in less than about 1 hour. Higher rates of heating can also be employed, as necessary. For example, the chromatographic column can be heated from about ambient temperature to about 75° C., or if necessary, to about 100° C. or to about 125° C. in less than about 30 minutes. Advantageously, the chromatographic column can be readily cooled back to ambient temperatures at similar rates, such that the system is prepared for lower-temperature characterization.

In a preferred embodiment for this characterization protocol, the chromatographic column is preferably the relatively high-aspect ratio chromatographic column discussed above. The relatively low mass of such a column enables it to be rapidly heated (and/or cooled) relative to conventional columns employed for high-temperature characterization. Additionally, the detector can be a temperature-insensitive detector, such as described below, that can reside external to a heated environment. In such liquid chromatography systems, the column can be the only component thereof in the heated environment. Hence, the liquid chromatography system, as a whole, can be rapidly prepared for high-temperature characterization, and if desired, rapidly converted back to ambient-temperature conditions.

Mobile Phase Composition Gradient

In a further high-temperature characterization protocol, a polymer sample can be characterized in a liquid chromatographic system that employs a compositional gradient to the mobile phase for selectively eluting one or more components of polymer sample from the chromatographic column. While such an approach has been employed in connection with ambient-temperature systems, methods and apparatus for high-temperature liquid chromatography with a mobile-phase compositional gradient have not been heretofore employed.

Hence, in a preferred approach, a polymer sample can be characterized by loading the polymer sample onto a chromatographic column, and maintaining the loaded polymer sample at a temperature of not less than 75° C. One or more sample components of the loaded polymer sample are then eluted with a mobile-phase eluant having a temperature of not less than about 75° C. while the composition of the mobile-phase eluant is controlled to vary over time to separate at least one sample component of the sample from other sample components thereof. A property of at least one of the separated sample components is detected. As desired, the loaded polymer sample can be maintained at a temperature of not less than 100° C., or not less than about 125° C., and the mobile-phase eluant can have a temperature of not less than about 100° C., or not less than about 125° C.

With reference to FIG. 6, such a preferred mobile-phase gradient approach can be effected with a liquid chromatography system 10 comprising an enclosure defining a heated environment (e.g. oven 112), where the heated environment is maintained at a temperature of not less than about 75° C. A chromatographic column 102 resides in the heated environment. The chromatographic column 102 can comprise a surface defining a pressurizable separation cavity, an inlet port for receiving a mobile phase and for supplying a polymer sample to the separation cavity, an effluent port for discharging the mobile phase and the polymer sample or separated components thereof from the separation cavity, and a stationary-phase within the separation cavity. The system 10 also comprises an injection valve 210 (100) having one or more injection ports 108 adaptable for fluid communication with the chromatographic column 102 for injecting polymer samples into the mobile phase. The system 10 further comprises two or more reservoirs and pumps adequate to establish a mobile-phase compositional gradient—more specifically, a first reservoir 114 containing a first mobile-phase fluid, and a second reservoir 120 containing a second mobile-phase fluid. First and second pumps 116, 118 are dedicated to first and second reservoirs, 114, 120, respectively. The system 10 also comprises one or more mixing zones 144 adapted for or adaptable for fluid communication with the first reservoir 114 and the second reservoir 120 for mixing of the first and second mobile-phase fluids to form a mobile-phase eluant having compositions (and/or temperatures) that can vary over time. The one or more mixing zones 144 are further adapted for or adaptable for fluid communication with the inlet port of the chromatographic column 102 for eluting one or more sample components of the sample with the mobile-phase eluant to separate at least one sample component of the sample from other sample components thereof. One or more detectors 130, 132 are in fluid communication with the effluent port of the chromatographic column 102 for detecting a property of at least one of the sample components.

The system 10 can optionally comprise a third reservoir and/or a fourth reservoir (not shown) having a third and/or a fourth dedicated pump, respectively) for containing a third and/or a fourth mobile-phase fluid, with such third and/or fourth reservoir being adaptable for fluid communication with a mixing zone for mixing of the third and/or fourth mobile-phase fluid with one or both of the first or second mobile-phase fluids. Each of the reservoirs 114, 120 and associated pumps 116, 118 are preferably isolable from each other, for example, with valves 124.

The location of the one or more mixing zones 144 within the liquid chromatography system 10 is not narrowly critical. The mixing zones 144 can be, for example, directly upstream of the inlet port to the chromatographic column 102. In another embodiment, the mixing zone 144 can be located in a mobile-phase column-supply line upstream and/or downstream of the injection valve 100. In a further embodiment, the chromatographic column 102 can comprise two inlet ports, each of which is in fluid communication with a different mobile-phase reservoir 114, 120, 129, and the mixing zone is within the chromatographic column 102.

Mobile-Phase Temperature Gradient

In yet another polymer characterization protocol, a polymer sample can be characterized in a liquid chromatographic system that employs a temperature gradient to the mobile phase for selectively eluting one or more components of polymer sample from the chromatographic column. While such an approach may have primary applications in connection with high-temperature polymer characterization, the protocols can also be advantageously employed in connection with ambient-temperature and/or cold-temperature protocols.

According to one method for characterizing a polymer sample, a polymer sample is loaded onto a chromatographic column. One or more sample components of the loaded polymer sample are eluted with a mobile-phase eluant while the temperature of the mobile-phase eluant is controlled to vary over time to separate at least one sample component of the sample from other sample components thereof. A property of at least one of the separated sample components is detected.

In practice, such a method can be used for precipitation-redissolution chromatography or adsorption chromatography where the solubility or adsorptivity of the polymer sample components are controlled by mobile-phase temperature—alone or in combination with a change in mobile-phase composition. Briefly, a polymer sample is injected into a mobile phase having a temperature less than the temperature at which one or more components of the polymer sample (e.g., a polymer component, a monomer component) are soluble or not adsorbed, such that the one or more polymer sample components precipitate and forms a separate gel-phase or become adsorbed—typically depositing onto the stationary-phase media of the column. The temperature of the mobile phase is then gradually increased such that the one or more precipitated or adsorbed components will selectively redissolve into the mobile phase based on its respective solubility therein. Since the temperature-dependence of the solubility or adsorptivity is a function of both molecular weight and the particular chemistry of the component, meaningful resolution of polymer sample components and molecular-weight distributions can be obtained.

In preferred applications, therefore, the polymer sample preferably comprises at least one precipitated sample component after being loaded onto the chromatographic column. For high-temperature characterization applications, the polymer sample can comprise one or more sample components that are insoluble at a temperature of less than about 75° C., or alternatively, at a temperatures of less than about 100° C., or of less than about 125° C. Moreover, because desorption from the stationary-phase of the column is based on selective resolubilization of sample components, one or more sample components are preferably non-desorbing from the stationary-phase media at a temperature of less than about 75° C., or alternatively, at a temperatures of less than about 100° C., or of less than about 125° C.

The method described in the immediately-preceding paragraphs can be advantageously effected with a liquid chromatography system such as is depicted in FIG. 6, and described above in connection with liquid chromatography based on mobile-phase compositional gradients. Referring to FIG. 6, a mobile-phase temperature gradient can be achieved over time by heating a first reservoir 114 to maintaining a first mobile-phase fluid at a first (e.g., hot) temperature, and heating a second reservoir 120 to maintaining a second mobile-phase fluid at a second (e.g., cold) temperature that is different from the first temperature. The temperature of the mobile phase supplied to the column 102 can then be controlled by varying the relative amounts of the first and second mobile-phase fluids supplied to a mixing zone 144. For high-temperature characterization applications, where the column 102 resides in a heated environment (e.g., oven 112), a mixing zone 144 is preferably situated immediately upstream of the inlet port to the column 102, and moreover, the system 10 preferably has a short transfer line from a reservoir (e.g., the third reservoir 129) to the mixing zone 144, such that the temperature-normalizing effects of the heated environment are minimized.

More generally, a liquid chromatography system for effecting separation with a mobile-phase temperature gradient can comprise, referring to FIG. 6, a chromatographic column 102, and an injection valve 100 having one or more injection ports 108. The system 10 also comprises a reservoir (e.g., 114) for containing a mobile-phase fluid. The reservoir is adapted for or adaptable for fluid communication with the inlet port of the chromatographic column. The system 10 further comprises a heater for controlling the temperature of the mobile-phase fluid such that one or more sample components of the polymer sample can be eluted with a mobile-phase fluid having a temperature that varies over time to separate at least one sample component of the sample from other sample components thereof, and a detector in fluid communication with the effluent port of the chromatographic column for detecting a property of at least one of the sample components.

The particular design for the mobile-phase heater is not critical. The heater can be, for example, an enclosure defining a heated environment (e.g., oven 112) in which the chromatographic column resides, or alternatively, in which a length of a mobile-phase fluid transfer line resides. In some cases, the heated environment can be maintained at a temperature of not less than about 75° C., or alternatively, not less than about 100° C., or not less than about 125° C. The heater can also be a heating element (e.g. resistive-heating element or a fluid-heat-exchanger) in thermal communication with the reservoir, or alternatively, in thermal communication with a mobile-phase fluid transfer line.

Column/Stationary-Phase Temperature Gradient

In a related, alternative approach, the solubility of a polymer sample component can be controlled with temperature to effect a chromatographic separation by controlling the temperature of the chromatographic column directly— through a temperature-control elements such as heating and/or cooling elements. The temperature of the column and its stationary-phase media can be directly controlled either alternatively to or in addition to controlling the temperature of the mobile phase. In preferred embodiments, the temperature of the column and/or stationary-phase are controllably varied while maintaining the temperature of the mobile phase approximately constant. Moreover, the temperature of the column and/or stationary-phase can be controllably varied not only with time, but also with relative position over the length of the column.

Hence, in another preferred protocol, a polymer sample can be characterized by loading a polymer sample onto a chromatographic column. The loaded sample is then eluted with a mobile-phase eluant. The temperature of the column and/or stationary-phase is controllably varied—directly by a temperature control element in thermal communication with the column—while eluting the column with the mobile-phase eluant, such that at least one sample component of the loaded sample is separated from other sample components thereof. A property of at least one of the separated sample components is detected.

The mobile-phase eluant can be supplied to the column at a temperature that is constant over time or alternatively, that varies over time. To effect precipitation of a sample component in a precipitation-redissolution chromatographic separation, the temperature of the column can also be directly controlled while loading the sample onto the column, such that at least one sample component precipitates or adsorbs onto the stationary-phase media.

A number of system configurations can be employed to achieve direct temperature control of the chromatographic column. Preferably, for example, the temperature of the column is directly controlled with a temperature-control element in direct thermal communication with the column. The temperature-control element can be a heating element or a cooling element. Exemplary temperature-control elements can include, for example, a resistive-heating element or a fluid-heat-exchanger in thermal communication with the column.

Reduced-Sensitivity Detectors

In yet another polymer characterization protocol, a polymer sample can be characterized in a flow characterization system (e.g., liquid chromatographic system) that employs a detector that is less temperature sensitive than conventional detectors. That is, the detector (e.g., a mass detector) can encounter larger variations in sample temperature without substantially affecting detection of a property of interest. Moreover, the detector preferably does not have to be equilibrated to the same temperature as the sample being characterized. A system having such a detector is advantageous in several aspects. First, a detector having a reduced temperature-sensitivity allows for a greater degree of variation of the heated environment (e.g., oven). As such, a less expensive heated environment can be employed. Moreover, the heated environment can be accessed, at least briefly, during a high-temperature characterization protocol without substantially impacting the detection data. As an additional advantage, the temperature-insensitive detector can, in some cases, be located external to the heated environment. As such, the size of the heated environment can be reduced, allowing less expensive equipment. Moreover, the rate at which the components of the characterization system can be heated up and/or cooled down is improved, since thermal equillibration of the detector will not be required.

Hence, a flow characterization system (e.g., liquid chromatography system 10) effective for high-temperature characterization of a polymer sample can comprise, with reference to FIG. 6, a enclosure defining a heated environment (e.g., oven 112). The heated environment is maintained at a temperature of not less than about 75° C. and has at least about ±0.5° C. variation in temperature. A liquid chromatography system 10 also comprises a chromatographic column 102 residing in the heated environment. The flow characterization system further comprises an injection valve 100 having one or more injection ports 108, a reservoir (e.g., 114) in fluid communication with the inlet port of the chromatographic column 102 and/or with detector 130, and one or more detectors 130 132 in fluid communication with the effluent port of the chromatographic column 102 or the injection port 108 for detecting a property of at least one of the sample components. At least one of the detector is insensitive to variations in temperature of about ±0.5° C.

In some embodiments for the flow characterization system, the heated environment is maintained at a temperature of not less than about 100° C., or alternatively, at a temperature of not less than about 125° C. Moreover, the heated environment can have a variation in temperature of at least about ±1° C., with the detector being insensitive to the variations in temperature of about ±1° C. Alternatively, the heated environment can have a variation in temperature of at least about ±2° C., or in some applications, at least about ±5° C., with the detector being insensitive to the variations in temperature of about ±2° C. or in some applications, of about ±5° C., respectively. The detector is most preferably an evaporative light scattering detector (ELSD).

Hence, in a preferred liquid chromatography protocol, a polymer sample can be characterized by separating at least one sample component of a polymer sample from other sample components thereof in a chromatographic column residing in a heated environment. The heated environment is maintained at a temperature of not less than about 75° C., while a variation in the temperature of the heated environment of at least about of at least about ±0.5° C. is allowed. A property of at least one of the separated sample components is detected with a detector insensitive to the about ±0.5° C. variation in temperature of the heated environment.

In variations of the preferred protocol, the allowed variation in temperature of the heated environment can be at least about ±1° C., or in some cases, at least about ±2° C. or at least about ±5° C., and the detector is insensitive to the about ±1° C., or in some cases, at least about ±2° C. or at least about ±5° C. variation in temperature of the heated environment, respectively. In any of such cases, the heated environment can be maintained to be not less than about 100° C., or alternatively, not less than about 125° C.

High-Temperature Flow-Injection Analysis

In a preferred high-temperature flow-injection analysis protocol, a polymer sample can be characterized by serially injecting a plurality of polymer samples into a mobile phase of a continuous-flow detector. A property of the injected samples or of components thereof is detected with a continuous-flow detector. The polymer samples are maintained at a temperature of not less than about 75° C. during a period of time including from when the samples are injected into the mobile phase of the continuous-flow detector to when the property of the injected samples or of a component thereof is detected.

In alternative approaches, the polymer samples can be maintained at a temperature of not less than about 100° C., or of not less than about 125° C. during the period of time including from when the samples are injected into the mobile phase of the continuous-flow detector to when the property of the injected samples or of a component thereof is detected.

Calibration Methods and Standards for Flow Characterization Systems

Flow characterization systems are typically calibrated using calibration standards having known properties. For gel permeation chromatography (GPC), for example, calibration standards comprising known molecular weights can be used to calibrate the GPC system. Typically, a calibration standard comprises a heterogeneous polymer component having a number of polymer subcomponents that differ with respect to the calibrating property. Such subcomponents are typically referred to as "known standards" or, simply, "standards" that are well characterized with respect to the calibrating property of interest. For molecular weight (or hydrodynamic volume), for example, a calibration standard typically comprises polymer standards having the same repeat unit, but having well-defined and well-characterized differences with respect to molecular weight (or hydrodynamic volume).

It is generally preferred to calibrate a flow characterization system with calibration standards comprising a polymer component that has polymer molecules with the same repeat units as the as the target polymer molecule being characterized by the system. For example, if polymer samples comprising polyisobutylene polymer components are the target polymer samples being characterized, the calibration standard also preferably comprises polyisobutylene polymer components.

However, because adequate standards are not generally available for each of the many different polymers being investigated, investigators have long employed "universal calibration" approaches. For GPC, universal calibration is based on the premise that the multiplication products of intrinsic viscosities and molecular weights (hydrodynamic volumes) are independent of polymer type. Mark-Houwink parameters, which describe the molecular weight dependence on intrinsic viscosity for a particular polymer, can be used to create universal calibration plots from actual calibrations performed with available calibration standards such as polystyrene. Although such "universal calibration" approaches can be used to calibrate for polymer molecules for which direct physical standards are not available, are difficult to obtain, are expensive and/or are unstable, such practices typically introduce errors—particularly if values of intrinsic viscosities are taken from literature rather than measured directly under the particular conditions to be use for the polymer characterization system.

Despite such inaccuracies, such "universal" standards are frequently employed because they offer another desirable attribute—extremely narrow polydispersities that enable the convenience of a "single-shot" calibration. That is, calibration of the flow characterization system can be effected by introducing a single polymer sample having, and typically consisting essentially of a single polymer component, the polymer component comprising a number of subcomponents (e.g., standards), each of which comprises polymer molecules having the same repeat unit but varying with respect to molecular weight (hydrodynamic volume) of those polymer molecules. However, such a "single-shot" or "one-shot" calibration approach is most practical if the determined molecular weight (hydrodynamic volume) distribution peaks are very narrow—with polydispersity indexes of about 1.0. Single-shot calibration with polymer components having broad-band distributions, rather than narrow-band distributions are generally ineffective for calibration purposes due to inadequate resolution. See, for example, FIG. 22A and Example 25. Presently, calibration standards comprising polymer components having narrow-band distributions are available for relatively few types of polymer molecules, such as polystyrene—commonly used for organic solvent systems and poly(ethylene oxide) or poly(ethyleneglycols)—commonly used in aqueous systems.

While polystyrene or other narrow-band calibration standards can be used directly, with molecular weights (hydrodynamic volumes) or other properties reported as, for example, "polystyrene-equivalent" molecular weights (hydrodynamic volumes), such an approach does not provide accurate absolute values for the property of interest, and as such, may not necessarily provide a meaningful basis for direct comparison between systems.

The options based on conventional methodologies for calibrating characterization systems for target polymer samples for which polymer components with narrow-band distributions are not available are not attractive for combinatorial polymer chemistry applications. One could (1) calibrate with a mixture of narrow-band standards comprised of polymer molecules having different repeat units than those of the target polymer sample; (2) rely on universal calibration and/or (3) perform repetitive, "multi-shot" calibration runs with calibration polymer samples consisting of a single, broader-band polymer component. As noted, the former alternatives have inherent inaccuracies. The latter alternative is time consuming. The latter approach can also be expensive—particularly where repetitive calibrations are required and the standards are not reusable, for example, due to degradation over time and/or during the calibration process. Hence, while such alternatives may have been acceptable for conventional polymer chemistry research, they are inadequate for applications that demand both accuracy and high-speed calibration at reasonable costs—such as combinatorial polymer research applications.

Accordingly, compositions and methods are disclosed herein that allow for accurate, rapid, "single-shot" characterization of polymer characterization systems. The compositions disclosed herein are "single-shot" calibration standards that provide calibration accuracy equivalent to a series of "multi-shot" calibrations with polymer components having the target polymer being characterized.

Briefly, an indirect calibration standard of the present invention is a composition that consists essentially of a polymer component. The polymer component comprises a plurality of narrow-band polymer subcomponents, each of which can be a narrow-band polymer standard. Each of the narrow-band polymer standards preferably has a different known molecular weight, a polydispersity index ranging from about 1.00 to about 1.10, and a hydrodynamic volume that is substantially equivalent to the hydrodynamic volume of a series of broad-band target-polymer standards. The target-polymer standards are preferably target-polymer standards, each having a different known molecular weight, and having a polydispersity index of more than about 1.10. Because the polymer molecule of the narrow-band polymer standards is different the polymer molecule of the broad-band target polymer standards (i.e., the narrow-band polymer standards have a different repeat structure from the broad-band polymer standards) the actual molecular weights of the corresponding polymer standards will be different.

More specifically, an indirect calibration standard is a composition that consists essentially of a heterogeneous polymer component. The polymer component comprises a plurality of first, narrow-band polymer standards (subcomponents) and a continuous liquid-phase in which the narrow-band polymer standards can be dissolved, emulsified and/or dispersed. Each of the narrow-band polymer standards has a polydispersity index of about 1 and each comprises polymer molecules—with the same repeat structure as, but with a different hydrodynamic volumes than— the polymer molecules of other narrow-band polymer standards. Significantly, the hydrodynamic volume of each polymer molecule for a given standard is substantially equivalent to (i.e., the same as) the hydrodynamic volume of a corresponding target polymer standard molecule. Each of a plurality of target polymer standards comprise one of the corresponding target polymer molecules. The target polymer standards are typically wide-band polymer standards, and are, in any case, preselected to include target polymer molecules having the same repeat structure, but with hydrodynamic volumes that vary over a range of hydrodynamic volumes sufficient to prepare an effective calibration curve (e.g., molecular weight vs. retention time). The actual molecular weights of the narrow-band polymer molecules will typically be different than the actual molecular weights of the corresponding target-polymer molecules.

In a preferred application, for example, where the first, narrow-band polymer component is a polystyrene component, the indirect calibration standard is a composition that comprises two or more polystyrene standards and a continuous liquid-phase. Each of the polystyrene standards have a polydispersity index of about 1 and comprise polystyrene molecules having a hydrodynamic volume substantially equivalent to the hydrodynamic volume of a preselected target polymer standards. The target polymer standards are a preferably a polymer other than polystyrene. A set of the two or more target-polymer standards can comprise the two or more preselected target-polymer molecules. The two or more target polymer molecules are preselected to have hydrodynamic volumes that vary over a range of hydrodynamic volumes sufficient to prepare an effective calibration curve (e.g., molecular weight vs. retention time).

The number of narrow-band polymer components generally corresponds to the number of target-polymer components, and can generally range from two to about ten, but can be 5 or more, or 10 or more, and is preferably about 5. The polydispersity index of the narrow-band polymer standards can range from about 1.0 to about 1.10, and preferably ranges from about 1.0 to about 1.05. Preferred target polymers include polymers for which presently available polymer standards have a polydispersity index of less than about 1.10, are not readily available, are prohibitively expensive and/or are not stable under the anticipated characterization conditions. Exemplary target polymers include polyisobutylene, polyethylene, polybutylacrylate, polypropylene, polymethylmethacrylate, polyvinylacetate, polystyrene sulfonic acid, and polyacrylamide, among others.

The indirect calibration standards of the present invention can be prepared as follows. In one set of steps, two or more target-polymer standards with known molecular weights (e.g., peak molecular weight and/or average molecular weight) are serially and individually loaded into a polymer characterization system—preferably a liquid chromatography system, and more preferably a size exclusion chromatography system. Each of the target polymer standards comprises target polymer molecules. Each of the target polymer molecules is a polymer other than a narrow-band polymer, preferably with a polydispersity index of more than about 1.10, and each target polymer molecule has the same repeat structure as, but a different hydrodynamic volume than, other target polymer molecules. The hydrodynamic volume of the target polymer molecules is determined for each of the individually loaded target polymer standards (subcomponents).

In a second set of steps, performed before or after the first set of steps, two or more narrow-band polymer standards are loaded into the polymer characterization system. Each of the loaded narrow-band polymer standards has a polydispersity index of about 1 and comprises a narrow-band polymer molecule. Each narrow-band polymer molecule has the same repeat structure as, but a different hydrodynamic volume than, other narrow-band polymer molecules. The hydrodynamic volume of the narrow-band polymer molecules is determined for each of the loaded narrow-band polymer standards.

After the first and second set of steps, two or more narrow-band polymer standards that comprise narrow-band polymer molecules having a hydrodynamic volume substantially equivalent to the hydrodynamic volume of a target polymer molecule are selected. A composition comprising the selected narrow-band polymer standards is then formed. The composition preferably consists essentially of the selected narrow-band polymer standards and a continuous liquid-phase, but may include other additives, etc. for control purposes.

In an exemplary method for preparing preferred polystyrene calibration protocols, a first target-polymer standard is loaded into a polymer characterization system. The first target-polymer standard comprises target-polymer molecules other than the narrow-band polymer. The hydrodynamic volume of the target polymer molecules are determined. A second target polymer subcomponent is loaded into the polymer characterization system. The second target polymer component comprises target polymer molecules other than polystyrene. The second target polymer molecules have the same repeat structure as, but a different molecular weight than, the first target polymer molecules. The hydrodynamic volume of the second target polymer molecules is determined. Preferably, one or more additional target polymer standards are serially loaded into the polymer characterization system. The one or more additional target polymer standards each comprise one or more additional target-polymer molecules other than polystyrene. The one or more additional target polymer molecules each have the same repeat structure as, but a different molecular weight than, the first target polymer molecule, the second target polymer molecules and other additional target polymer molecules. The hydrodynamic volumes of the one or more additional target polymer molecule are determined. A series of polystyrene standards are loaded into the polymer characterization system. Each of the loaded polystyrene standards has a polydispersity index of about 1 and comprises polystyrene molecules having a different hydrodynamic volume than other polystyrene molecules. The hydrodynamic volume of the polystyrene molecules is determined for each of the loaded polystyrene standards. Polystyrene standards having polystyrene molecules with a hydrodynamic volume substantially equivalent to the determined hydrodynamic volumes of the target polymer molecules are selected. A composition comprising the selected polystyrene standards (subcomponents) is then formed.

A polymer characterization system can be calibrated with the indirect calibration standards described above and/or prepared as described above. Briefly, the calibration composition is loaded into a polymer characterization system. A property of the narrow-band (e.g., polystyrene) components of the injected composition is detected and/or determined. A correlation is prepared by assigning the value for the detected property of each of the narrow-band standards to the corresponding target polymer standards.

Once a polymer characterization system has been calibrated, a plurality of target polymer samples can be screened as described herein.

Multi-System, Rapid-Serial Polymer Characterization

The high-throughput rapid-serial flow characterization systems can be advantageously applied in combination with other polymer characterization systems for effectively and efficiently characterizing a plurality of polymer samples.

In a general case, a plurality of polymer samples, preferably four or more polymer samples (e.g., in a library of polymer samples) are serially screened (characterized) for a first property of interest with a first characterization system. The first characterization system has an average sample-throughput of not more than about 10 minutes per sample, and in preferred approaches, is a flow characterization system. At least one of the four or more samples screened with the first characterization system is then screened for a second property of interest with a second characterization system. Additional screenings with additional characterization systems can also be effected.

The second polymer characterization system can be, but is not necessarily a flow characterization system, and moreover, can have, but does not necessarily have, an average sample-throughput of not more than about 10 minutes per sample. The first and second properties of interest can be the same or different. The first and second characterization systems can likewise be the same or different. For example, each characterization system can be a liquid chromatography system, each can be a flow-injection analysis system, or one can be a liquid chromatography with the other being a flow-injection analysis system.

In one approach, the two or more characterization systems can be used to screen each of a plurality of polymer samples for two or more properties of interest—one property being determined by one system, another property being determined by a second system, etc. More specifically, each of the four or more samples screened with the first characterization system can be screened for the second property of interest with the second characterization system.

In a preferred application of such approach, in which two liquid chromatography systems are employed, a polymer sample is withdrawn from a sample container, and a first portion of the withdrawn sample is injected into a mobile phase of the first liquid chromatography system. A second portion of the withdrawn sample is then injected into a mobile phase of the second liquid chromatography system. Each of the injected samples are then separated, and a property of the samples or of a component thereof is detected in each of the respective systems. These steps can be repeated in series for additional polymer samples.

In an alternative approach, a first characterization system can be used to prescreen each of a plurality of polymer samples for a first property of interest, and then a second characterization system can be used to rescreen certain selected polymer samples—for the same or for a different property of interest—with the selection for the second screen being based on results from the first prescreening. Briefly, four or more samples are screened to determine a first property of interest in a first screen. A figure of merit is determined for the four or more samples. The figure of merit is preferably based, at least in part, on the first determined property of interest. The determined figure of merit for the four or more samples is compared with a predetermined threshold value for the figure of merit. The threshold value can be based, for example, on results with a then-best-known system. Those samples of the four or more samples that favorably compare with the predetermined threshold value for the figure of merit are then screened with the second characterization system. In a preferred embodiment, only those samples that favorably compare to the predetermined figure of merit are screened with the second characterization system.

Non-Flow Characterization Systems

In non-flow polymer characterization systems, the polymer sample is detected statically without flow of the sample. With reference to FIG. 1A, non-flow characterization processes may be effected with a sample preparation (steps A, D and E) or without a sample preparation (steps D and E).

For rapid screening of combinatorial libraries of polymers, is it often not necessary to know the polydispersity index (PDI). In such cases, parallel light scattering systems may be advantageously employed. Preferably, the polymer samples are diluted in preparation for light-scattering detection, as described for the serial flow characterization approach. The preparation step can be effected in a rapid-serial, a parallel or a serial-parallel manner.

In a rapid-serial embodiment, a light-scattering detector, such as a dynamic light-scattering (DLS) detector, can be mounted on a platform for staging over an array of polymer samples. The DLS detector can then serially detect the light scattered from each of the samples in sequence. Automated relative motion can be provided between the DLS-platform and the array of polymer samples by robotically controlling the DLS-platform and/or the array of sample containers.

In one parallel embodiment, an entire library of polymers can be illuminated and scattered light can be detected from every sample at the same time. The concentration of polymer in each well may be derived in parallel by using parallel absorbency or refractive index measurements. In this embodiment, the detector can be a static light-scattering (SLS) detector or a dynamic light-scattering (DLS) detector.

In another parallel embodiment, a property of two or more polymer samples is detected simultaneously (i.e., in parallel) with two or more light-scattering detectors positioned in appropriate relation to the samples. In a preferred system, the light-scattering detectors are dynamic light-scattering (DLS) detectors, and preferably, fiber-optic DLS detectors. Such a system can also be employed in a pure-parallel, a serial-parallel or hybrid serial-parallel detection approach for screening four or more polymer samples, such as a combinatorial library of polymerization product mixtures arranged in an array of sample containers. Here, two or more DLS detectors can be mounted on a common platform for staging over the array of polymer samples. The two or more DLS detectors can detect the light scattered from two or more of the samples in parallel, and then the DLS-platform (or the array) can be moved such that the two or more DLS detectors can be serially advanced to the next subset of polymer samples. Automated relative motion can be provided between the DLS-platform and the array of polymer samples by robotically controlling the DLS-platform and/or the array of sample containers. The number of DLS probes employed in the system can range from 2 to the number of polymer samples included within a plurality of polymer samples (as generally discussed above).

A preferred configuration thereof can be a non-flow, immersion or non-immersion parallel DLS configuration. Briefly, with reference to FIG. 24, a parallel DLS system can comprise an array 410 of two or more DLS probes 420, 420', 420" configured in a spatial relationship with respect to each other. Each probe 420, 420', 420" can include a transmitting optical fiber 425, 425', 425" and a receiving optical fiber 430, 430', 430". Although shown in FIG. 24 as being immersed, the probes 420, 420', 420" can also be positioned over the samples of interest in a non-immersed configuration. Each probe 420, 420', 420" further comprises a single-mode fiber coupler, also referred to as an optic (not shown), suitable for transmitting incident light to a sample and/or collecting scattered light from a sample. These couplers can preferably consist, for example, of a gradient refractive index (GRIN) lens aligned to a single-mode optical fiber—and be mounted at an angle of 45 degrees with respect to each other to provide for a measurement angle of 135 degrees. Other couplers and/or configurations known in the art can also be effectively employed. A laser light can be provided from laser 435 and coupled into the transmitting optical fibers 425, 425', 425" by means of the fiber-optics array 440. The coupled laser light can be delivered into the sample 20 and scattered by one or more particles of the polymer sample. The scattered light can be collected via one or more optics, as described above, and coupled into the receiving optical fiber 430, 430', 430". The receiving optical fiber 430, 430', 430" can be in optical communication with a detector array 450 (e.g., an array of avalanche photodiodes (APD)). Measurements and photon autocorrelation can be taken in a serial manner using commercially-available autocorrelator boards, such as the ALV 5000/E (ALV GmbH, Langen, Germany). The hydrodynamic radius, $R_h$, and the polydispersity index (PDI) can be determined from the detected scattered light with commercially-available software. Other suitable configurations can also be arranged by a person of skill in the art.

In each of the aforementioned embodiments, the light-scattering detector can, depending on its design characteristics, be immersed in the polymer sample during detection or, alternatively, be positioned near the surface of the polymer sample for detection without immersion therein.

The following examples illustrate the principles and advantages of the invention.

EXAMPLES

Example 1
Auto-Sampling with Single Robotic Arm

This example demonstrates rapid, automated (robotic) preparation and sampling of polymer libraries using one robotic arm.

Conventional, Commercially-Available Auto-Sampler

A conventional, commercially-available auto-sampler was evaluated. A Gilson®, (Middleton, Wis.) Model 215 is described by Gilson® as a computer-controlled XYZ robot with stationary rack. It was mounted with a steel needle probe, a syringe pump, and a valve and sample loop connected to an HPLC system. This auto-sampler, as programmed by Gilson®, required slightly more than 90 seconds to perform the following sequence of operations: (1) drawing 100 µL water from position 1 of a microtiter plate; (2) loading a 50 µL sample loop with the water; (3) actuating the injection valve to inject the sample into the flow system; (4) cleaning the probe needle by flushing in preparation for the next sample; and (5) repeating steps (1) through (4) with water from a second position 2 of the same microtiter plate. The Gilson auto-sampler's computer interface did not allow the user to program a new sample container (e.g., reactor block or sample block) configurations—geometries or locations. Also, the robotic arm speed was not controllable, and the probe was incapable of liquid level-sensing.

Auto-Sampler of the Invention

The following describes the design and operation of the auto-sampler 200, probe 201, loading port 204, and injection valve 210 (100) shown in FIG. 4 and discussed in connection therewith.

A programmable XYZ robotic arm (RSP 9651, Cavro Scientific Instruments, Inc., Sunnyvale, Calif.) mounted on a platform was fitted with a fluoropolymer-coated steel needle probe (Cavro part # 722470), a 500 μL piston syringe pump (Cavro, model XL 3000) connected to the needle probe by flexible fluoropolymer tubing, and a fluoropolymer probe wash/waste station was mounted on the platform. Features of the RSP-9651 include capacitance based liquid-level sensing, optical step loss motion detection and completely programmable motor speeds and acceleration profiles. A serial interface, electrically actuated 8-port valve (model EHC8W, Valco Instruments Co. Inc.) was mounted to the platform, controlled by the same computer as the sampler. The valve was mounted with two 50 μL sample loops, a waste line, and a port comprising a fluoropolymer liner in a steel nut (Valco, VISF-1), sized to fit a 22 gauge needle (0.028 in. O.D.) for manual loading of samples with a syringe. The inner diameter of the steel nut was milled larger (from 0.0645 in. to 0.076 in.), and the outermost 0.25 in of the fluoropolymer liner was enlarged within the nut to an inner diameter of ca. 0.042 in, to accommodate the coated sampler probe needle, which has an outer diameter of 0.0425 in. With the probe needle inserted 0.20 in into the port, it was found that the mating fluoropolymer surfaces prevented any leaking of fluid as the sample introduced fluid into the port, even at flow rates exceeding 60 mL/min. In this configuration, it was still possible to manually load individual samples into the loops on the valve without leaking, using a hand-held syringe with a 22-gauge needle inserted fully into the same port.

The valve was also fitted with inlet and outlet flow lines leading to an HPLC system. The flow was provided by two pumps (Waters, model 515) capable of generating a solvent gradient, and the chromatography system was provided with fittings for inserting columns, filters, and detection systems including a light scattering detector (Precision Detectors, model PD 2020) enclosed within the housing of a refractive index detector (Waters, model 410). The systems also had a UV detector (Waters, model 486). The light-scattering detector simultaneously measured the static light scattering signals at 15 and 90 degrees, and the dynamic light scattering signal at 90 degrees. An interface box (264 in FIG. 2) acquires signals from all detectors.

A 96-well microtiter plate filled with water was placed on the platform, the syringe pump and probe were primed with water, and the computer was programmed with the locations and of the plate, the wash and waste stations, and the valve port. The instrument was programmed, and the following sequence of operations were executed: (1) drawing a 100 μL sample from position 1 of the microtiter plate; (2) loading the 50 μL sample loop with 80 μL of the drawn sample; (3) actuating the valve to inject the sample into the flow system; (4) expelling the remaining sample to waste and rinsing the inlet port of the valve with 200 μL of fresh diluent; (5) moving the probe to the cleaning station and cleaning with an additional 200 mL of diluent in preparation for the next sample; and (6) repeating steps (1) through (5) with each samples from positions 2–96 of the microtiter plate.

All of these operations were performed with an average sample-throughput of less than 8 seconds per sample. Such rapid-sampling rate is well suited to the rapid characterization methods of this invention.

Example 2
Auto-Sampler with Two Robotic Arms

This example demonstrates rapid, automated (robotic) preparation and sampling of combinatorial libraries using two robotic arms, allowing for multiple, simultaneous analyses.

A robotic sampler was prepared in a similar manner to Example 1, except using a two-arm XYZ robot (Cavro, model RSP 9652), two injection valves (Valco, model EHC8W), and four pumps (Cavro, model XL 3000). For each arm, two pumps were connected in series to a single probe needle on the arm, one pump fitted with a 500 μL syringe, and one pump with a 5000 μL syringe. In this configuration, good flow precision was obtained with the smaller volume pump when needed, while the larger volume pump can deliver instantaneous flow rates of approximately 300 mL/min and overall flow rates greater than 100 mL/min, allowing for very rapid rinsing, washing, and sample manipulation.

Liquid samples from an array of vessels were rapidly loaded and injected using this system, with intermittent steps including washing and rinsing, in a manner similar to that described in Example 1. These operations were performed with an average sample-throughput of about 4 seconds per sample.

Example 3
Precipitation—Redissolution Chromatography

This example demonstrates the use of a liquid chromatography system for rapid chromatographic separation of polystyrene polymer standards using precipitation-redissolution chromatography with a mobile-phase composition gradient. The results provided a calibration for the chromatographic system and conditions.

The robotic auto-sampler and injection valve set-up as in Example 1 was fitted with two sample loops (each having 50 microliter volume) in combination with a high-pressure liquid chromatographic (HPLC) apparatus comprising a two-pump gradient chromatography system, primed with methanol and tetrahydrofuran (THF) solvent. A porous crosslinked polystyrene monolithic column was utilized, prepared as described in Fréchet et al., *Journal of Chromatography A,* 752 (1996) 59–66 and Fréchet et al., *Anal. Chem.* 1996, 68, 315–321. The HPLC system was configured such that the combined flow of the pump system passed through the valve, the column, and then to a UV chromatographic detector. The entire system, including pump control and data acquisition from the detector was computer-controlled.

Filtered solutions in THF of 12 commercially available (Aldrich Chemical Co. Inc.) narrow molecular weight distribution polystyrene standards of various molecular weights were dissolved in THF at a nominal concentration of 5.0 mg/mL. Nominal molecular weights ranged from 760 g/mol to 1,880,000 g/mol. Each of these polymer samples were serially injected into the mobile phase of the liquid chromatography system while varying a range of chromatographic parameters, including total pump flow and gradient composition and speed, to obtain reasonable separation of the various standards in a short time.

In one experiment, the following conditions were chosen:

TABLE 1

Mobile-Phase Conditions

| Time (min) | Parameter | Value |
|---|---|---|
| 0.0 | Total flow | 10 mL/min. |
| 0.0 | Starting Solvent Composition | 30% THF:70% Methanol |
| 0.35 | Begin Linear Gradient | To 70% THF:30% Methanol |
| 1.20 | End Gradient | maintain at 70% THF: 30% Methanol |

TABLE 1-continued

Mobile-Phase Conditions

| Time (min) | Parameter | Value |
|---|---|---|
| 1.50 | Begin Linear Gradient | to initial solvent composition |
| 1.60 | Initial Solvent Composition | Reestablished (30% THF: 70% Methanol) |

The resulting chromatographic traces showed a linear increase in UV absorbance during the gradient due to the linear change in solvent composition. The profile of this gradient, measured with no sample injected, can be subtracted from each chromatogram to simplify the appearance of the raw data obtained for each sample. Using the chromatographic conditions described above, the following peak retention times for the standards were measured:

TABLE 2

Peak Retention Times for Polystyrene Standards

| Nominal Molecular Weight | Retention Time (min) |
|---|---|
| 760 | Not observed |
| 3700 | Not observed |
| 13700 | 0.7987 |
| 18700 | 0.8785 |
| 29300 | 0.9323 |
| 44000 | 0.9794 |
| 114200 | 1.0440 |
| 212400 | 1.0849 |
| 382100 | 1.1195 |
| 679000 | 1.1430 |
| 935000 | 1.1458 |
| 1880000 | 1.1650 |

The results of Table 2 comprise a calibration of the column and chromatographic conditions—thereby allowing subsequent determination of peak molecular weight or molecular weight distribution for samples of unknown molecular weight.

Example 4
Rapid Flow-Injection Light Scattering

The example demonstrates a rapid flow-injection light-scattering (FILS) technique in which light-scattering measurement techniques were used to determine an average molecular weight of a polymer sample without chromatographic separation of the sample.

The general layout of the system was generally as described in Example 1, and as shown in FIG. 7, including an eight-port injection valve 210 (See FIG. 3), a filter 212, and no column 214. A light scattering detector 216 and a RI detector 218 were used. Samples were injected with a syringe, by hand, into the 8-port injection valve, the valve having two 50-$\mu$l injection valves. The system was maintained at a temperature of 36° C.

$M_w$ for each sample was calculated using an algorithm incorporated in the analysis software ("Precision Analyze", version 0.99.031(Jun. 8, 1997), Precision Detectors) accompanying the PD2020. In order to determine $M_w$, points in the chromatogram representing the baseline of the 15 and 90 degree signals and the RI signals were first selected ("baseline regions"). Linear least-squares fits of these points defined the three baselines. Then, an integration region encompassing the main sample peak was chosen. The software then calculated $M_w$ based on the SLS and RI data and baseline values in this integration region. The calculation was performed in the limit of the radius of gyration, $R_g$, being much less than the measurement wavelength, and the polymer concentration in the dilute limit representing isolated molecules. This calculation also used the angular form-factor, $P(\theta)$, appropriate for a Gaussian-coil molecule, and fitted it to the SLS signals to extract $M_w$. For polymers with $M_w$ less than about 10,000 kD, this method determined values of $M_w$ within less than 5% of values calculated assuming non-Gaussian-coil forms of $P(\theta)$.

$R_h$ was calculated from the diffusion constant of the polymer molecules, which is obtained by fitting the photon-photon correlation function to an exponential. The PD2020 system was designed to allow for measurements of $R_h$ at each time-slice of the chromatogram for sufficiently low flow rates.

A series of polystyrene Mw-standards in THF as described in Example 3 were measured using the system just described. The solvent flow rate was 0.5 ml/min, and the injection volume was 50 $\mu$l. The width of the signal peaks in the flow-injection analysis output data were typically 0.3 min. The centers of the SLS peaks appeared at about 0.35 min after each injection. For comparison, the same series of standards was run with the same system altered to include a set of conventional GPC columns (Polymer Laboratories, 1110-6500) placed between the filter and the light-scattering cell.

Table 3 shows the experimental $M_w$ values for each of the standards, determined with a liquid chromatography system with the control conventional GPC columns in place, and with the flow-injection analysis method disclosed herein. The $M_w$ values measured followed the expected overall trend except for the 13.7 kD and 0.760 kD samples. There was fairly close quantitative agreement between measured and nominal values over most of the range of molecular weights. Note that there was very good quantitative agreement between the values measured with the conventional GPC columns and the nominal values.

TABLE 3

Rapid Flow-Injection Analysis versus Conventional GPC

| Nominal $M_w$ (kD) | Measured $M_w$ (kD) (conventional GPC. Columns) | Rapid Light Scattering Method measured $M_w$ (kD) |
|---|---|---|
| 0.76 | 0.72 | 35 |
| 2.36 | 2.04 | 17 |
| 3.70 | 3.88 | 21 |
| 13.7 | 12.3 | 56 |
| 18.7 | 18.6 | 53 |
| 29.3 | 25.3 | 63 |
| 44.0 | 44.2 | 80 |
| 114 | 106 | 134 |
| 212 | 220 | 171 |
| 382 | 385 | 240 |
| 679 | 704 | 285 |
| 935 | 954 | 421 |
| 1880 | 1709 | 1760 |

The following Table 4 shows a comparison of the $R_h$ values of the same samples using (1) conventional GPC chromatography, (2) the RFLS method of this Example and (3) the literature values of the samples. There was good quantitative agreement across all three sets of values for the 44 kD through 935 kD samples. For samples with weights 29.3 kD and below, reliable measured values were not acquired. Literature values of $R_h$ were derived from a fit to data published in: W. Mandema and H. Zeldenrust, Polymer, vol. 18, p.835, (1977). (In Table 4, NA=not available)

TABLE 4

Comparison of Nominal and Measured $R_h$ of Polystyrene Standards

| Nominal $M_w$ (kD) | Literature $R_h$ (nm) (T = 24 deg C.) | measured $R_h$ (nm) (conven. columns) | measured $R_h$ (nm) (no columns) |
|---|---|---|---|
| 0.76 | NA | NA | NA |
| 2.36 | NA | NA | NA |
| 3.70 | NA | NA | NA |
| 13.7 | NA | NA | NA |
| 18.7 | 3.8 | NA | NA |
| 29.3 | 4.9 | NA | NA |
| 44.0 | 6.1 | 6.5 | 9 |
| 114 | 10 | 8.8 | 12 |
| 212 | 15 | 13 | 15 |
| 382 | 21 | 17 | 20 |
| 679 | 29 | 23 | 25 |
| 935 | 34 | 27 | 30 |
| 1880 | 51 | 37 | 35 |

These data demonstrate that rapid, meaningful measurements of molecular weight are available by the methods of the invention, with no chromatographic separation of polymeric components. In this example, the average sample-throughput (i.e., measurement time) was about 0.3 min/sample (about 20 seconds per sample).

As disclosed herein, other variations can be effected to achieve even faster measurements, for example, by controlling flow rate, sample size, acquisition times and other parameters. It is also possible to measure the radius of gyration, $R_g$, using this experimental set-up by comparing the relative amplitudes of the 15 and 90 degree SLS signals. The system should preferably be calibrated with high precision using a low-$M_w$ polymer standard in order to measure $R_g$ successfully, as the angular anisotropy of the scattering is weak.

Example 5
Rapid Size Exclusion Chromatography

This example demonstrates a rapid liquid-chromatography light-scattering measurement using the short, high-aspect ratio column using the same 12 commercially available polystyrene standards as used in Example 4.

The set-up was the same as in Example 4, with the exception of the presence of a short chromatographic column (Polymer Laboratories, 1110-1520, sold as a GPC "guard column") inserted in-line between the filter and the light-scattering cell. Briefly, the column was 7.5 mm in diameter and 5 cm height and was packed with polystyrene beads targeted to pass sample components having a molecular weight greater than about 1000 without substantial separation thereof.

$M_w$ was calculated using the algorithm in Precision Analyze, version 0.99.031(Jun. 8, 1997), in the same way as in Example 4 over an integration region (including elution times between 0.2 and 0.36 minutes). The software allowed for automatic analysis of a series of files without requiring the operator to manually choose integration and baseline regions for each file individually.

A set of polystyrene standards in THF were prepared and measured as described in Example 4. In addition, mixtures of polystyrene with varying amounts of styrene monomer and polymerization catalyst (oxidized form of CuCl with 2 equivalents of 4,4'-bis(5-nonyl)2-2'-bipyridine) were also measured. The flow rate was set to 4 ml/min in all cases.

In the case of pure polystyrene in THF, Table 5 below shows that the measured molecular weights agree the nominal weights, with generally better agreement than in Example 4. In the case of the highest $M_w$, the integration region partially encompassed an extraneous peak in the DRI signal at 0.34 min, possible due to contamination. Manually setting the integration region in this case to exclude the extraneous peak yields a more accurate (1740 kD) value. In all cases, the characteristic peak in the RI signal due to the carrier solvent eluted at times later than the polymers. Consequently, the solvent peak could be excluded from the $M_w$ calculation, thereby improving the accuracy of the weight determination.

TABLE 5

Nominal and Measured $M_w$ of Pure Polystyrene Standards

| Nominal $M_w$ (kD) | Measured $M_w$ (kD) |
|---|---|
| 0.760 | 2.5 |
| 2.36 | 5.0 |
| 3.70 | 3.7 |
| 13.7 | 14 |
| 18.7 | 18 |
| 29.3 | 27 |
| 44.0 | 43 |
| 114 | 100 |
| 212 | 200 |
| 382 | 300 |
| 679 | 560 |
| 935 | 710 |
| 1880 | 860 |

For solutions containing polystyrene and styrene monomer, Table 6 confirms that the measured molecular weights are independent of the monomer concentration, because the polymer (elution times ranging between 0.23 and 0.31 min) eluted separately from the monomers and other small molecule components of the sample, which elute at about 0.39 min.

TABLE 6

Nominal and Measured Mw of Polystyrene Standards with Varying Styrene (Monomer)-to-Polystyrene Ratios

| Nominal $M_w$ (kD) | styrene/polystyrene (weight ratio) | Measured $M_w$ (kD) (short column) |
|---|---|---|
| 2.36 | 0.5 | 6.5 |
| 2.36 | 1 | 2.5 |
| 2.36 | 2 | 1.7 |
| 2.36 | 4 | 1.6 |
| 2.36 | 8 | 2.0 |
| 29.3 | 0.5 | 26 |
| 29.3 | 1 | 26 |
| 29.3 | 2 | 26 |
| 29.3 | 4 | 25 |
| 29.3 | 8 | 25 |
| 679 | 0.5 | 560 |
| 679 | 1 | 580 |
| 679 | 2 | 600 |
| 679 | 4 | 590 |
| 679 | 8 | 580 |

The chromatograms of the polystyrene-catalyst mixtures do not show clear peaks attributable to the catalyst molecules. Furthermore, the heights and shapes of the polymer SLS and DRI traces do not change appreciably with the concentration of catalyst. Table 7, below, shows that the measured molecular weights are independent of the catalyst concentration.

TABLE 7

Nominal and Measured Mw of Polystyrene Standards with Varying Amounts of Catalyst

| Nominal $M_w$ (kD) | catalyst weight % | measured $M_w$ (kD) (short column) |
|---|---|---|
| 2.36 | 0.5 | 4.0 |
| 2.36 | 1 | 4.7 |
| 2.36 | 5 | 5.7 |
| 29.3 | 0.5 | 25 |
| 29.3 | 1 | 28 |
| 29.3 | 5 | 28 |
| 679 | 0.5 | 580 |
| 679 | 1 | 570 |
| 679 | 5 | 570 |

Thus, these data demonstrate rapid characterization of polymer samples and good correlation between the measured and nominal molecular weights of polystyrene standards, with and without added monomer and catalyst components, using a short, high-aspect ratio chromatographic column. The sample-throughput for the plurality of samples was about 18 seconds per sample.

Example 6
Flow-Injection Light-Scattering w/Emulsion Polymer Samples

This example demonstrates flow-injection light-scattering (FILS) using a dynamic light-scattering detector (DLS) to determine particle size ($R_h$) for an array of emulsion polymers.

An array of emulsion polymers was prepared as in Example 10, below, with the following change. Solution No. 8 was replaced with water in rows 7 and 8. Diluted samples of these emulsions were prepared in water by serial dilution in three stages to 1/30,000 of the library as synthesized. Using the auto-sampler described in Example 1, with a flow rate of 0.3 mL/min. of water, a sample volume of 50 μL and an in-line 2 μm filter, the sample was introduced directly into the DLS detector—without any chromatographic separation column. Samples were injected at 2 min. intervals. The instrument was calibrated with known polystyrene particle size standards (Duke Scientific, Palo Alto, Calif., nominal $R_h$ of 9.5 nm, 25 nm, 51 nm and 102 nm).

As each sample moved through the detector, between 15 and 50 independent measurements of $R_h$ were obtained. Statistically invalid measurements were removed and the remaining results were averaged. These $R_h$ values (in nm) are shown below in Table 8.

These data show that the flow-injection light-scattering methods of this invention usefully screen emulsion samples for variation in particle size. Rows 7 and 8, which contained water and no surfactant, produced unstable emulsions, as predictable, and no meaningful DLS correlation was obtained, as was predicted.

Example 7
High-Temperature Characterization with Rapid Liquid-Chromatography

This example demonstrates rapid liquid-chromatography with a short, high-aspect ratio column and light-scattering detectors to determine the molecular weight of polymers soluble at high-temperatures.

The experimental apparatus for this example was as shown in FIGS. 7A and 7B and discussed in connection therewith, except for the following deviations: (1) the auto-sampler probe 201 was equipped with a thermostatically controlled heating element to form a heated probe (tip); (2) the sample container 202 was likewise equipped with a thermostatically controlled heating element; and (3) the loading port 204 and external portions of the transfer line 206 were also heated with a thermostatically controlled heating element. The remaining components of the system were in a temperature-controlled oven (high-temperature GPC (Polymer Laboratories model 210)). The temperature of the oven was maintained at about 140° C. (but the oven could vary in temperature from 35° C. to 210° C.). The injection valve was a six-port valve with the sample loop of the injection valve having volume of about 20-μl. A filter was employed. The mobile-phase flow rate was about 4 ml/min.

The polymer samples were injected into the system at intervals of about 60 seconds, filtered in-line and then chromatographically separated with a short, high-aspect ratio column packed with traditional high temperature GPC packing material (Polymer Laboratories, 1110-1520). The separated sample was detected with a static light scattering detector (Precision Detectors light-scattering system (PD2040)) and a RI detector (supplied from Polymer Laboratories with the oven) configured in series in that order. Two computers were used to controlled the system substantially as described in connection with FIG. 7B.

$M_w$ was calculated using the algorithm in Precision Analyze, version 0.99.031(Jun. 8, 1997), in the same way as in Experiment 4.

Commercially available polyethylene samples and a broad MWD sample available from Aldrich were evaluated in this system. Table 9 shows the results:

TABLE 8

Hydrodynamic Radius Determined by Flow-Injection Light-Scattering

| Row/Col | 1 | 2 | 3 | 4 | 5 | 6 | 7 | 8 | 9 | 10 | 11 | 12 |
|---|---|---|---|---|---|---|---|---|---|---|---|---|
| 1 | 45.2 | 42.4 | 39.7 | 76.0 | N.D. | N.D. | 43.6 | 52.3 | N.D. | 68.4 | 84.5 | N.D. |
| 2 | 40.4 | N.D. | 36.8 | N.D. | N.D. | N.D. | 39.2 | 39.5 | 58.3 | 56.6 | 63.7 | 99.6 |
| 3 | 45.2 | 44.8 | 42.0 | 48.1 | 75.8 | N.D. | 47.9 | 51.1 | 51.7 | 49.0 | 69.9 | 87.9 |
| 4 | 41.5 | 37.9 | 38.5 | 69.8 | 39.4 | 86.9 | 41.8 | 42.5 | 48.1 | 47.8 | 57.2 | 80.8 |
| 5 | 42.2 | 39.6 | 38.6 | 37.4 | 41.0 | 44.4 | 45.6 | 58.2 | 71.5 | 46.4 | 60.0 | 73.9 |
| 6 | N.D. | 38.4 | 36.2 | 40.0 | 36.6 | 37.8 | 41.5 | 42.1 | 49.4 | 42.7 | 49.9 | 62.4 |
| 7 | N.D. | N.D. | N.D. | N.D. | N.D. | N.D. | N.D. | N.D. | N.D. | N.D. | N.D. | N.D. |
| 8 | N.D. | N.D. | N.D. | N.D. | N.D. | N.D. | N.D. | N.D. | N.D. | N.D. | N.D. | N.D. |

TABLE 9

Nominal and Measured $M_w$

| Sample | nominal $M_w$ (kD) | Measured $M_w$ (kD) |
|---|---|---|
| Polyethylene-broad distribution | 35 | 24 |
| Polyethylene standard | 76.5 | 140 |
| Polystyrene standard | 68.6 | 74 |
| Polystyrene standard | 212.7 | 140 |

These results show the method is particularly useful for differentiating between polymers having approximately a factor of 2 difference in average molecular weight. Thus for libraries of polymers having molecular weights on the order of $10^3$ versus polymers having molecular weights on the order of $10^4$ versus polymers having molecular weights on the order of $10^5$ are easily distinguished. As can be seen, very rapid measurement (average sample-throughput of about 1 minute) of weight average molecular weight is possible at high temperature. The elution times of these samples were all about 0.25 min, with peak widths of 0.08 min. The solvent elutes at 0.46 min, with a width of 0.13 min. This system can also be operated faster than in this example, as discussed above.

Example 8
Characterization of a Combinatorial Polymer Library with Rapid LC

This example demonstrates the synthesis and rapid characterization of a combinatorial library of polystyrene polymers with rapid liquid chromatography.

In a dry, nitrogen atmosphere glovebox two stock solutions (I and II) were prepared. Ligand L-1 having the structure shown below was used in stock solutions I and II:

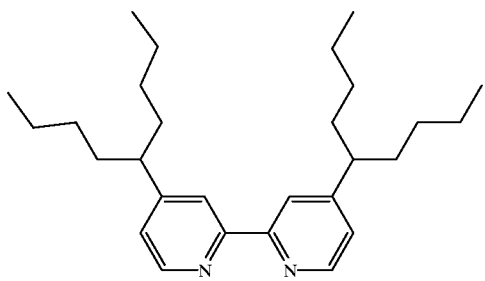

L-1

L-1 was synthesized from reductive coupling of 4-(5-nonyl) pyridine using Pd/C catalyst at 200° C. L-2 was purchased.

1-chloro-1-phenylethane (hereinafter "I-1") was synthesized by treatment of styrene with HCl and purified by distillation. I-2 was synthesized by reaction of commercially available divinylbenzene with HCl, followed by purification by distillation. I-2 had the following structure:

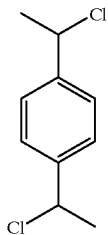

I-2

All other materials were commercially available and were purified using conventional techniques.

Solution I comprised 20.8 mg (0.21 mmol) of CuCl, 179.5 mg (0.44 mmol) of compound L-1, 10.9 g (0.105 mol) of styrene and 37.1 mg (0.21 mmol) of I-1. Solution II comprised 20.8 mg (0.21 mmol) of CuCl, 179.5 mg (0.44 mmol) of compound L-1, 10.9 g (0.105 mol) of styrene and 38.3 mg (0.105 mmol) of I-2. A 10-row by 11-column 110-vessel glass-lined aluminum reactor block array with approximately 800 uL volume per vessel, was prepared in a drybox under dry nitrogen atmosphere, and stock solutions I and II manually distributed to the vessels using a metering pipettor, such that elements 1–55 (5 rows by 11 columns) received 200 $\mu$L of solution I and elements 56–110 (also 5 rows by 11 columns) received 200 $\mu$L of solution II. To this array was added additional solvent such that each row of the two 5×11 arrays received a different solvent, with each column received a different amount of the solvent. The five solvents used were benzene (rows 1,6), o-dichlorobenzene (rows 2,7), m-dimethoxybenzene (rows 3,8), diphenyl ether (rows 4,9), and diethyl carbonate (rows 5,10). The 11 columns received a gradient of dilutions in even increments from 0 to 400 uL in steps of 40 uL. In this fashion an array of 10×11 diverse polymerization reactions were prepared, requiring a setup time of approximately 3.5 hrs.

The reactor block array was sealed, removed from the glovebox, and heated to 120° C. for 15 hrs with agitation provided by an orbital shaker. The reactor block was allowed to cool, and to each vessel was added 0.5 mL of tetrahydrofuran solvent, and the block was sealed and headed at 105° C. with orbital shaking for approximately 1 hour, to allow formation of uniform, fluid solutions, and the reactor block was allowed to cool.

Each element of the array was analyzed by rapid, automated liquid chromatography using a system substantially the same as shown in FIG. 7A and described in connection therewith and in a manner similar to that described in Example 3. Using the automated sampler, samples of each vial, ranging from 6 to 16 $\mu$L were drawn (5+column number=volume in $\mu$L, sampling more volume from higher numbered columns in order to have more equal amounts of polymer, in anticipation of lower monomer conversion with increasing dilution). Each sample was dispensed into a well containing approximately 2 mL of methanol, in a polypropylene deep-well microtiter plate, precipitating any solid polymeric product.

For each well, the methanol was robotically decanted and the solid polymeric product washed with 1 mL additional methanol. The solid polymeric product was redissolved with robotic mixing in 0.5 mL tetrahydrofuran, and a 100 $\mu$L sample of this solution was drawn and used to load a 50 $\mu$L sample loop, followed by rapid chromatographic evaluation. During the time of each chromatographic run, the steps of washing and redissolving the next sample were conducted, so that each sample injection automatically occurred at 110 sec intervals. Table 10, below, shows the peak molecular weight/1000 of the samples derived from the analysis. Where little or no polymer was detected in the analysis, a zero is indicated. In most cases this is due to samples with low molecular weight, where the polymeric product precipitated into methanol as a fine slurry that was removed during the washing step and not retained for redissolution and analysis.

TABLE 10

Peak Molecular Weight/1000

|     | Col 1 | 2 | 3 | 4 | 5 | 6 | 7 | 8 | 9 | 10 | 11 |
|---|---|---|---|---|---|---|---|---|---|---|---|
| Row 1 | 48.9 | 46.8 | 44.1 | 0.0 | 0.0 | 0.0 | 0.0 | 0.0 | 0.0 | 0.0 | 0.0 |
| 2 | 48.8 | 44.1 | 0.0 | 40.7 | 40.7 | 40.0 | 0.0 | 0.0 | 31.1 | 0.0 | 0.0 |
| 3 | 49.9 | 44.1 | 40.7 | 40.7 | 40.7 | 45.0 | 42.4 | 40.0 | 0.0 | 0.0 | 0.0 |
| 4 | 49.9 | 44.1 | 44.1 | 36.4 | 38.5 | 0.0 | 0.0 | 0.0 | 0.0 | 0.0 | 0.0 |
| 5 | 49.9 | 40.0 | 33.9 | 31.1 | 0.0 | 0.0 | 0.0 | 0.0 | 0.0 | 0.0 | 0.0 |
| 6 | 74.3 | 62.4 | 55.6 | 48.8 | 46.8 | 40.0 | 36.4 | 33.3 | 0.0 | 0.0 | 0.0 |
| 7 | 65.5 | 61.0 | 55.6 | 55.6 | 55.6 | 52.1 | 49.9 | 48.8 | 46.8 | 42.4 | 40.7 |
| 8 | 0.0 | 62.4 | 58.2 | 55.6 | 58.2 | 37.1 | 54.4 | 49.9 | 52.1 | 48.8 | 48.8 |
| 9 | 68.8 | 58.2 | 55.6 | 58.2 | 54.4 | 52.1 | 65.5 | 49.9 | 48.8 | 45.0 | 40.7 |
| 10 | 65.5 | 49.9 | 44.1 | 38.5 | 33.3 | 22.8 | 0.0 | 20.4 | 0.0 | 0.0 | 0.0 |

Each element of the array was analyzed by a second time, with the following changes in attempt to obtain more rapid analysis: samples of each vial, ranging from 10 to 60 μL were drawn (5+5×column number=volume in μL). Each sample was dispensed with agitation into a well containing approximately 2 mL of methanol, in a polypropylene deep-well microtiter plate, precipitating any solid polymeric product. For each well, the methanol was robotically decanted. With no further washing, the solid polymeric product was redissolved with robotic mixing in 0.5 mL tetrahydrofuran, and analyzed as above. Table 11, below, shows the peak molecular weight of the samples derived from this second analysis. In a few cases, polymer was detected where none was seen in the previous analysis, and the chromatographic data was more complicated due to the presence of more low-molecular weight impurities, but in general, the same molecular weight trends were observed.

more slowly and thoroughly purify the polymeric product before analysis. Samples of each vial, ranging from 10 to 60 μL were drawn (5+5×column number=volume in μL). Each sample was dispensed with agitation into a containing approximately 2 mL of methanol, in a polypropylene deep-well microtiter plate, precipitating any solid polymeric product. For each well, the methanol was botanically decanted. To each well was added 1.0 mL of additional methanol with agitation. This procedure was completed for all 110 wells before any chromatographic analysis was begun, to allow more time for extraction of low-molecular weight impurities and more efficient settling of the solid polymeric product. Then for each well, the methanol was decanted, the solid polymeric product was redissolved with robotic mixing in 0.5 mL tetrahydrofuran, and the polymer was analyzed as above. Table 12, below, the peak molecular weight of the

TABLE 11

Peak Molecular Weight/1000

|     | Col 1 | 2 | 3 | 4 | 5 | 6 | 7 | 8 | 9 | 10 | 11 |
|---|---|---|---|---|---|---|---|---|---|---|---|
| Row 1 | 49.2 | 49.2 | 46.2 | 0.0 | 0.0 | 0.0 | 0.0 | 0.0 | 0.0 | 0.0 | 0.0 |
| 2 | 49.2 | 46.2 | 41.8 | 42.6 | 44.3 | 41.8 | 0.0 | 0.0 | 30.6 | 0.0 | 0.0 |
| 3 | 49.2 | 47.2 | 44.3 | 41.8 | 44.3 | 51.4 | 46.2 | 49.2 | 0.0 | 0.0 | 0.0 |
| 4 | 47.2 | 46.2 | 51.4 | 35.2 | 40.2 | 49.2 | 49.2 | 0.0 | 0.0 | 0.0 | 0.0 |
| 5 | 47.2 | 42.6 | 33.4 | 31.7 | 21.5 | 0.0 | 0.0 | 0.0 | 0.0 | 0.0 | 0.0 |
| 6 | 64.8 | 61.7 | 61.7 | 51.4 | 47.2 | 40.2 | 36.5 | 33.4 | 0.0 | 0.0 | 0.0 |
| 7 | 61.7 | 61.7 | 61.7 | 57.5 | 57.5 | 54.9 | 49.2 | 51.4 | 49.2 | 46.2 | 41.8 |
| 8 | 46.2 | 64.8 | 61.7 | 57.5 | 61.7 | 40.2 | 54.9 | 57.5 | 57.5 | 51.4 | 51.4 |
| 9 | 64.8 | 64.8 | 58.8 | 57.5 | 58.8 | 58.8 | 66.4 | 66.4 | 47.2 | 49.2 | 42.6 |
| 10 | 61.7 | 54.9 | 44.3 | 41.8 | 33.4 | 23.4 | 17.8 | 20.9 | 0.0 | 0.0 | 0.0 |

Each element of the array was analyzed by a third time, with the following changes relative to the first analysis, to samples derived from this third analysis. In general, the same molecular weight trends were observed.

TABLE 12

Peak Molecular Weight/1000

|     | Col 1 | 2 | 3 | 4 | 5 | 6 | 7 | 8 | 9 | 10 | 11 |
|---|---|---|---|---|---|---|---|---|---|---|---|
| Row 1 | 53.7 | 49.1 | 51.3 | 0.0 | 0.0 | 0.0 | 0.0 | 0.0 | 0.0 | 0.0 | 0.0 |
| 2 | 51.3 | 49.1 | 0.0 | 46.0 | 46.0 | 46.0 | 0.0 | 0.0 | 30.2 | 0.0 | 0.0 |
| 3 | 48.0 | 51.3 | 49.1 | 44.1 | 46.0 | 51.3 | 49.1 | 43.2 | 0.0 | 0.0 | 0.0 |
| 4 | 48.0 | 48.0 | 51.3 | 37.6 | 41.5 | 41.5 | 0.0 | 0.0 | 0.0 | 0.0 | 0.0 |
| 5 | 48.0 | 48.0 | 35.5 | 32.4 | 23.7 | 0.0 | 0.0 | 0.0 | 0.0 | 0.0 | 0.0 |
| 6 | 0.0 | 74.3 | 68.6 | 57.6 | 57.6 | 44.1 | 39.9 | 35.5 | 0.0 | 0.0 | 0.0 |
| 7 | 70.4 | 74.3 | 62.0 | 65.2 | 65.2 | 62.0 | 57.6 | 55.0 | 57.6 | 49.1 | 48.0 |
| 8 | 49.1 | 70.4 | 65.2 | 65.2 | 70.4 | 70.4 | 65.2 | 60.5 | 62.0 | 57.6 | 55.0 |

TABLE 12-continued

| | | | | | Peak Molecular Weight/1000 | | | | | | |
|---|---|---|---|---|---|---|---|---|---|---|---|
| | Col 1 | 2 | 3 | 4 | 5 | 6 | 7 | 8 | 9 | 10 | 11 |
| 9 | 70.4 | 70.4 | 68.6 | 68.6 | 74.3 | 74.3 | 85.5 | 62.0 | 60.5 | 46.0 | 39.9 |
| 10 | 78.5 | 57.6 | 48.0 | 39.1 | 31.3 | 17.6 | 0.0 | 0.0 | 0.0 | 0.0 | 0.0 |

Example 9
Characterization of a Combinatorial Polymer Library with Rapid LC

This example demonstrates characterization of a combinatorial polymer library width rapid liquid chromatography using short, high-aspect ratio columns in combination with light-scattering detection. The method of screening of Example 5 was used with a combinatorial library of controlled radical polymerizations.

Materials I-1, I-2, and L-1 were prepared as in Example 8. All other materials were commercially available and were purified using conventional techniques.

Five stock solutions were prepared in a dry nitrogen atmosphere glovebox (I, II, III, IV, and V), as follows: Solution I comprised 19.8 mg (0.141 mmol) of 1-chloro-1-phenylethane (I-1) and 800 μL (6.98 mmol) of styrene. Solution II comprised 20 mg (0.2 mmol) CuCl, 174 mg of L-1 (0.42 mmol), and 3.33 mL (29.1 mmol) of styrene. Solution III comprised 14.2 mg of I-2 (0.07 mmol) and 800 μL (6.98 mmol) styrene. Solution IV comprised 14.7 mg (0.105 mmol) of I-1, 10.4 mg (0.105 mmol) CuCl, 90 mg (0.022 mmol) of L-1, and 6 mL (52.4 mmol) of styrene. Solution V comprised 10.7 mg (0.0525 mmol) of I-2, 10.4 mg (0.105 mmol) CuCl, 90 mg (0.022 mmol) of L-1, and 6 mL (52.4 mmol) of styrene.

A 7-row by 12-column 84-vessel glass-lined aluminum reactor block array with approximately 800 μL volume per vessel, was prepared in a drybox under dry nitrogen atmosphere, and stock solutions I–V were manually distributed to the vessels using a metering pipettor, such that elements 1–5 received a gradient of Solution I (100 μL, 50 μL, 33.3 μL, 25 μL, and 20 μL), 100 μL of Solution II, and a gradient of excess styrene (0 μL, 50 μL, 66.7 μL, 75 μL, 80 μL). Elements 6–10 received a gradient of Solution III (100 μL, 50 μL, 33.3 μL, 25 μL, and 20 μL), 100 μL of Solution II, and a gradient of excess styrene (0 μL, 50 μL, 66.7 μL, 75 μL, 80 μL). Elements 11–15 received a gradient of Solution I (100 μL, 50 μL, 33.3 μL, 25 μL, and 20 μL), 100 μL of Solution II, a gradient of excess styrene (0 μL, 50 μL, 66.7 μL, 75 μL, 80 μL), and 200 μL of diphenylether. Elements 16–20 received a gradient of Solution III (100 μL, 50 μL, 33.3 μL, 25 μL, and 20 μL), 100 μL of Solution II, a gradient of excess styrene (0 μL, 50 μL, 66.7 μL, 75 μL, 80 μL), and 200 μL of diphenylether. Elements 21–50 (a 5×6 array) received 150 μL of Solution IV and a gradient of dilutions along each row by adding solvent (75 μL, 150 μL, 225 μL, 300 μL, 375 μL, 450 μL) with a different solvent in each row (diethyl carbonate, benzene, o-dichlorobenzene, m-dimethoxybenzene, and diphenylether, respectively). Similarly, elements 51–80 (a 5×6 array) received 150 μL of Solution V and a gradient of dilutions along each row by adding solvent (75 μL, 150 μL, 225 μL, 300 μL, 375 μL, 450 μL) with a different solvent in each row (diethyl carbonate, benzene, o-dichlorobenzene, m-dimethoxybenzene, and diphenylether, respectively). In this fashion an array of 7×12 diverse polymerization reactions were prepared, requiring a setup time of approximately 5 hrs. The reactor block array was sealed using a Teflon membrane covering a silicon rubber sheet compressed with an aluminum plate bolted in place.

The array was then heated to 120° C. for 15 hrs with agitation provided by an orbital shaker. The reaction block was allowed to cool, and to each vessel was added THF such that the total volume reached 0.8 mL, and the block was sealed and heated at 105° C. with orbital shaking for approximately 1 hr, to allow formation of homogeneous fluid solutions. The reactor block was allowed to cool.

Each element of the array was analyzed by rapid manner as described in Example 5, with the following procedure. Using a programmable robotic sampler, 20 μL of each vial were drawn and dispensed along with 250 μL of THF into a polypropylene microtiter plate. 100 μL of this diluted sample was drawn and used to load a 50 μL sample loop on an HPLC injector, followed by rapid LS evaluation. During the time of each analysis, the step of diluting the next sample was conducted, so that each sample injection automatically occurred at 40 sec. intervals. Table 13, below, shows the average $M_w/1000$ of the samples derived from the analysis.

TABLE 13

| | | | | | | Average $M_w/1000$ | | | | | | | |
|---|---|---|---|---|---|---|---|---|---|---|---|---|---|
| Col | | 1 | 2 | 3 | 4 | 5 | 6 | 7 | 8 | 9 | 10 | 11 | 12 |
| Row | 1 | 22.2 | 35.7 | 46.3 | 55.8 | 63.7 | NR | NR | 25.9 | 47.6 | 57.3 | 72 | 78.2 |
| | 2 | 8.65 | 15 | 22.3 | 26.6 | 30.4 | NR | NR | 11.2 | 19.8 | 33.1 | 40.1 | 42.9 |
| | 3 | 28.9 | 20.2 | 16.6 | 12.6 | 12 | 11.9 | 44 | 34.3 | 29.8 | 20.9 | 17.6 | 16.4 |
| | 4 | 38.9 | 29.6 | 26.1 | 24.1 | 24.2 | 22.9 | 56 | 51.7 | 45 | 38.7 | 30.9 | 27 |
| | 5 | 47.8 | 34.8 | 23.6 | 18.6 | 15.4 | 14.1 | 59.9 | 48.3 | 33.7 | 25.2 | 22.6 | 18.3 |
| | 6 | 40.6 | 28.6 | 15.3 | 12.9 | 12 | 13.1 | 45.8 | 20.8 | 17.7 | 12.3 | 13.3 | 13.8 |
| | 7 | 40.3 | 30.2 | 23.2 | 20.9 | 19.5 | 19.2 | 46.8 | 37.4 | 34.2 | 29.7 | 28.6 | 27.8 |

The expected trends of decreasing molecular weight with increasing dilution were observed. This demonstrates very rapid molecular weight determinations in combinatorial discovery of optimal catalytic processes.

Example 10
Characterization of Emulsion Samples with Rapid SEC—Adsorption LC

This example demonstrates rapid size exclusion chromatography (SEC), combined with adsorption chromatography for determining molecular weight, MWD and residual monomer concentration (i.e., conversion) in the presence of water in a combinatorial library of emulsion polymers. More specifically, the GPC characterization of hydrophobic polymers and conversion analysis in a single run is demonstrated. In such cases, the monomer peak can often be overlapped with a peak of the solvent used for polymerization; however, the approaches disclosed herein overcome this potential pitfall.

This specific example describes a method for both molecular weight characterization of polymer as well as quantitative analysis of monomer and polymer in a sample prepared by emulsion polymerization. The technique is based on combination of size-exclusion and adsorption effects. A size separation of polymer and monomer is obtained while water is adsorbed under these conditions and not interfering with the analysis.

The system used is described in Example 3, using an eight port Valco injection valve, a Waters 515 pump, a Waters UV-VIS 486 detector, a LS detector PD 2000 built inside the RI unit. (Also, a Waters 410 RI detector was connected to the system, but not used for this particular example. It was used in a later, related example.) A series of two 50×8 mm hydrophilic columns Suprema 30 Å and 1000 Å from Polymer Standard Services were used for the analyses. (A later experiment that followed this example combined the two columns together in a single mixed bed column, which provided equivalent, but slightly better separation). The chromatography was performed using THF as the mobile phase at various flow rates (1, 2, 5, and 10 mL/min). The chromatographic separation was completed in less than 2 min per sample (at 2 mL/min) with good resolution of separation and precision of the molecular weight determination at these flow rates. The separation can be obtained in about 20 seconds (at 10 mL/min), with some impact on the precision of the method.

An 8-row by 12-column combinatorial library array of 96 emulsion polymerization reactions was prepared according to the following procedure. Nine 20 ml vials were prepared with neat monomer, 10% surfactant solutions or initiator solution as described below, all from commercially available materials without further purification. Solution vials were as follows:

Solution Vial Contents
1) styrene
2) butyl acrylate
3) methyl methacrylate
4) vinyl acetate
5) sodium dodecyl sulfate (SDS)(Aldrich, 10 wt % in water)
6) sodium dodecylbenzenesulfonate (SDBS)(Aldrich, 10 wt % in water)
7) Rhodacal A246L (A246L)(Rhone Poulenc, diluted to 10 wt % in water)
8) Dowfax 2A1 (2A1)(Dow Chemical Co., diluted to 10 wt % in water)
9) $K_2S_2O_8$ (4 wt % in water)

A 96-member array of glass vessels in an aluminum reaction block was prepared. In an oxygen-free glovebox, using an automated sampler as described in Example 1, three of the above 9 solutions were dispensed to each vessel in the array, as shown in the following Table 14. Water was added to each vessel to bring the total volume to 500 µL. Solution 9 was added last to all of the vessels. The total time required for the automated, robotic dispensing was approximately 18 minutes. Each element of the table contains the solution number-quantity of that solution, in microliters.

TABLE 14

Sample-Preparation

| Row Col | 1 | 2 | 3 | 4 | 5 | 6 | 7 | 8 | 9 | 10 | 11 | 12 |
|---|---|---|---|---|---|---|---|---|---|---|---|---|
| 1 | 1-125 | 1-150 | 1-175 | 2-125 | 2-150 | 2-175 | 3-125 | 3-150 | 3-175 | 4-125 | 4-150 | 4-175 |
|   | 5-6.3 | 5-7.5 | 5-8.8 | 5-6.3 | 5-7.5 | 5-8.8 | 5-6.3 | 5-7.5 | 5-8.8 | 5-6.3 | 5-7.5 | 5-8.8 |
|   | 9-31.3 | 9-37.5 | 9-43.8 | 9-31.3 | 9-37.5 | 9-43.8 | 9-31.3 | 9-37.5 | 9-43.8 | 9-31.3 | 9-37.5 | 9-43.8 |
| 2 | 1-125 | 1-150 | 1-175 | 2-125 | 2-150 | 2-175 | 3-125 | 3-150 | 3-175 | 4-125 | 4-150 | 4-175 |
|   | 5-12.5 | 5-15.0 | 5-17.5 | 5-12.5 | 5-15.0 | 5-17.5 | 5-12.5 | 5-15.0 | 5-17.5 | 5-12.5 | 5-15.0 | 5-17.5 |
|   | 9-31.3 | 9-37.5 | 9-43.8 | 9-31.3 | 9-37.5 | 9-43.8 | 9-31.3 | 9-37.5 | 9-43.8 | 9-31.3 | 9-37.5 | 9-43.8 |
| 3 | 1-125 | 1-150 | 1-175 | 2-125 | 2-150 | 2-175 | 3-125 | 3-150 | 3-175 | 4-125 | 4-150 | 4-175 |
|   | 6-6.3 | 6-7.5 | 6-8.8 | 6-6.3 | 6-7.5 | 6-8.8 | 6-6.3 | 6-7.5 | 6-8.8 | 6-6.3 | 6-7.5 | 6-8.8 |
|   | 9-31.3 | 9-37.5 | 9-43.8 | 9-31.3 | 9-37.5 | 9-43.8 | 9-31.3 | 9-37.5 | 9-43.8 | 9-31.3 | 9-37.5 | 9-43.8 |
| 4 | 1-125 | 1-150 | 1-175 | 2-125 | 2-150 | 2-175 | 3-125 | 3-150 | 3-175 | 4-125 | 4-150 | 4-175 |
|   | 6-12.5 | 6-15.0 | 6-17.5 | 6-12.5 | 6-15.0 | 6-17.5 | 6-12.5 | 6-15.0 | 6-17.5 | 6-12.5 | 6-15.0 | 6-17.5 |
|   | 9-31.3 | 9-37.5 | 9-43.8 | 9-31.3 | 9-37.5 | 9-43.8 | 9-31.3 | 9-37.5 | 9-43.8 | 9-31.3 | 9-37.5 | 9-43.8 |
| 5 | 1-125 | 1-150 | 1-175 | 2-125 | 2-150 | 2-175 | 3-125 | 3-150 | 3-175 | 4-125 | 4-150 | 4-175 |
|   | 7-6.3 | 7-7.5 | 7-8.8 | 7-6.3 | 7-7.5 | 7-8.8 | 7-6.3 | 7-7.5 | 7-8.8 | 7-6.3 | 7-7.5 | 7-8.8 |
|   | 9-31.3 | 9-37.5 | 9-43.8 | 9-31.3 | 9-37.5 | 9-43.8 | 9-31.3 | 9-37.5 | 9-43.8 | 9-31.3 | 9-37.5 | 9-43.8 |
| 6 | 1-125 | 1-150 | 1-175 | 2-125 | 2-150 | 2-175 | 3-125 | 3-150 | 3-175 | 4-125 | 4-150 | 4-175 |
|   | 7-12.5 | 7-15.0 | 7-17.5 | 7-12.5 | 7-15.0 | 7-17.5 | 7-12.5 | 7-15.0 | 7-17.5 | 7-12.5 | 7-15.0 | 7-17.5 |
|   | 9-31.3 | 9-37.5 | 9-43.8 | 9-31.3 | 9-37.5 | 9-43.8 | 9-31.3 | 9-37.5 | 9-43.8 | 9-31.3 | 9-37.5 | 9-43.8 |
| 7 | 1-125 | 1-150 | 1-175 | 2-125 | 2-150 | 2-175 | 3-125 | 3-150 | 3-175 | 4-125 | 4-150 | 4-175 |
|   | 8-6.3 | 8-7.5 | 8-8.8 | 8-6.3 | 8-7.5 | 8-8.8 | 8-6.3 | 8-7.5 | 8-8.8 | 8-6.3 | 8-7.5 | 8-8.8 |
|   | 9-31.3 | 9-37.5 | 9-43.8 | 9-31.3 | 9-37.5 | 9-43.8 | 9-31.3 | 9-37.5 | 9-43.8 | 9-31.3 | 9-37.5 | 9-43.8 |
| 8 | 1-125 | 1-150 | 1-175 | 2-125 | 2-150 | 2-175 | 3-125 | 3-150 | 3-175 | 4-125 | 4-150 | 4-175 |
|   | 8-12.5 | 8-15.0 | 8-17.5 | 8-12.5 | 8-15.0 | 8-17.5 | 8-12.5 | 8-15.0 | 8-17.5 | 8-12.5 | 8-15.0 | 8-17.5 |
|   | 9-31.3 | 9-37.5 | 9-43.8 | 9-31.3 | 9-37.5 | 9-43.8 | 9-31.3 | 9-37.5 | 9-43.8 | 9-31.3 | 9-37.5 | 9-43.8 |

The reactor block was sealed and heated to 80° C. for 4 hours with agitation. The resulting array of polymer emulsions was allowed to cool and the reactor block opened. Visual inspection indicated that polymer emulsions had formed in most of the vessels of the array.

The product emulsions were diluted 100 times with THF and analyzed using the system described above. Molecular-weight data were obtained both from the GPC calibration curves using polystyrene standards and from light scattering at two different angles (15° and 90°). A quantitative analysis including both monomer and polymer content can be obtained from the peak areas. FIG. 8 shows a representative rapid gel permeation/adsorption HPLC separation of a sample, under the conditions: column, 30×10 mm, mobile phase, tetrahydrofuran at 2 mL/min, RI and LS detection.

Table 15, below, shows tabulated peak molecular weight as determined by this method and the following Table 16 shows the measured conversion in each polymerization vessel determined by relative UV-VIS areas of the monomer and polymer peaks, corrected for optical absorptivity of the components. Relative molecular weight distribution information (MWD) was also obtained.

Example 12
Characterizing Emulsion Samples with Rapid-Fire Light-Scattering

This example demonstrates rapid particle-size characterization of emulsion particles with rapid-fire static-light-scattering (SLS) detection—without chromatographic separation.

In this example, both light scattering and refractive index traces of various latex particles using the same chromatographic system as described in Example 4. The particle peak areas at RI trace remained the same for particular concen-

TABLE 15

Measured Peak Molecular Weights (kD)

| Col/Row | 1 | 2 | 3 | 4 | 5 | 6 | 7 | 8 | 9 | 10 | 11 | 12 |
|---|---|---|---|---|---|---|---|---|---|---|---|---|
| 1 | 131 | 128 | 125 | 113 | 105 | 30 | 683 | 615 | 486 | 256 | 152 | 244 |
| 2 | 122 | 164 | 195 | 138 | N.D. | 15 | 993 | 599 | 615 | 220 | 357 | 270 |
| 3 | 200 | 148 | 125 | 160 | 618 | 45 | 539 | 525 | 512 | 210 | 181 | 185 |
| 4 | 215 | 238 | 160 | 148 | N.D. | N.D. | 1169 | 740 | 525 | 322 | 131 | 250 |
| 5 | 138 | 131 | 134 | 145 | 73 | 79 | 539 | 375 | 357 | 204 | 205 | 238 |
| 6 | N.D. | 168 | 168 | 164 | 172 | 22 | 1048 | 845 | 474 | 190 | 195 | 226 |
| 7 | 232 | 244 | 172 | 181 | 215 | 119 | 615 | 474 | 339 | 172 | 199 | 238 |
| 8 | 145 | 215 | 220 | 250 | 238 | 190 | 438 | N.D. | N.D. | 138 | 190 | N.D. |

TABLE 16

Conversion Data Determined from Residual Monomer Detection

| Col/Row | 1 | 2 | 3 | 4 | 5 | 6 | 7 | 8 | 9 | 10 | 11 | 12 |
|---|---|---|---|---|---|---|---|---|---|---|---|---|
| 1 | 98.74 | 99.15 | 99.12 | 93.84 | 89.83 | 85.51 | 95.01 | 95.84 | 96.12 | 3.25 | 3.27 | 2.00 |
| 2 | 96.34 | 98.48 | 97.66 | 92.33 | 0.00 | 88.96 | 95.44 | 94.56 | 95.21 | 2.01 | 3.13 | 0.69 |
| 3 | 98.44 | 98.81 | 98.36 | 92.01 | 86.31 | 81.40 | 93.85 | 94.20 | 96.77 | 3.84 | 7.98 | 3.71 |
| 4 | 98.89 | 98.80 | 97.53 | 91.28 | 0.00 | 0.00 | 93.19 | 94.98 | 95.67 | 1.90 | 0.62 | 4.73 |
| 5 | 98.61 | 89.76 | 96.06 | 91.52 | 22.60 | 3.91 | 93.67 | 94.79 | 93.66 | 6.97 | 4.44 | 6.72 |
| 6 | 0.00 | 94.81 | 86.46 | 76.26 | 82.36 | 0.00 | 91.55 | 94.19 | 95.09 | 3.10 | 5.18 | 6.06 |
| 7 | 99.13 | 89.56 | 93.87 | 84.70 | 79.54 | 68.54 | 94.17 | 63.75 | 82.35 | 5.18 | 5.08 | 5.35 |
| 8 | 98.64 | 98.16 | 97.65 | 96.07 | 81.28 | 81.97 | 94.53 | 0.00 | 0.00 | 7.04 | 2.07 | 0.00 |

Example 11
Characterizing Emulsion Samples with SEC—Adsorption Chromatography This example demonstrates rapid characterization of emulsion particles with rapid size-exclusion-chromatography (SEC) with a short, high-aspect ratio columns having a stationary-phase media with large pore sizes for separating polymer emulsion particles.

Retention times were used to determine $R_h$ values of latex particles injected into the chromatographic systems, using the equipment described in Example 3 and short, high-aspect ratio columns (described below) packed with very a large pore size stationary phase. In this example, a series of standard dispersions of polystyrene latex particles diluted with water by a factor of 200 were injected into the chromatographic system using water as a mobile phase and a 30×10 mm chromatographic column packed with GM-GEL 3000 and GM-GEL 5000 beads (Kurita, Japan). The concentration of latex was detected by both RI and LS detectors. The RI signal was determined to be linearly on the mass of polymer in the sample.

FIG. 9 shows refractive index traces for latex particles of different sizes from this example. The average sample-throughput for this example was less than 2 min. per sample.

tration of particles regardless on the particle size, while the areas of the peaks in the LS trace were affected significantly by particle size. The response of LS detector relative to that of RI is a function of the particle size. After a calibration, this dependence can be used for rapid particle size determination of unknown samples.

FIG. 10 shows LS and RI traces obtained for latex particles of different sizes under the same flow conditions as in Example 11.

Example 13
Rapid Reverse-Phase Chromatography w/Compositional Gradient

This example demonstrates rapid characterization of polymer samples using reverse phase liquid chromatographic separation of polymers based on composition differences in the mobile phase.

In a dry nitrogen atmosphere glovebox were prepared twelve stock solutions. L-1 was synthesized from reductive coupling of 4-(5-nonyl)pyridine using Pd/C catalyst at 200° C. I-2 (1-chloro-1-phenylethane) was synthesized by reaction of commercially available styrene with HCl, followed by purification by distillation. All other materials were commercially available and were purified using conventional techniques. Solution I comprised 1.5 mL of styrene.

Solution II comprised 1.35 mL styrene and 0.15 mL of n-butylacrylate. Solution II comprised 1.35 mL styrene and 0.15 mL of n-butylacrylate. Solution III comprised 1.20 mL styrene and 0.30 mL of n-butylacrylate. Solution IV comprised 1.05 mL styrene and 0.45 mL of n-butylacrylate. Solution V comprised 0.90 mL styrene and 0.60 mL of n-butylacrylate. Solution VI comprised 0.75 mL styrene and 0.75 mL of n-butylacrylate. Solution VII comprised 0.60 mL styrene and 0.90 mL of n-butylacrylate. Solution VIII comprised 0.45 mL styrene and 1.05 mL of n-butylacrylate. Solution IX comprised 0.30 mL styrene and 1.20 mL of n-butylacrylate. Solution X comprised 0.15 mL styrene and 1.35 mL of n-butylacrylate. Solution XI comprised 1.50 mL of n-butylacrylate. Solution XII comprised 90 mg (0.64 mmol) of I-2, 63.4 mg (0.64 mmol) of CuCl, 584 mg (1.344 mmol) of L-1, and 2 mL of diethyl carbonate. A 5-row by 11-column 55-vessel glass-lined aluminum reactor block array with approximately 800 uL volume per vessel, was prepared in a drybox under dry nitrogen atmosphere, and stock solutions I–XII were manually distributed to the vessels using a metering pipettor, such that column 1 elements received 200 uL of solution I, column 2 elements received 200 uL of solution II, column 3 elements received 200 uL of solution III, column 4 elements received 200 uL of solution IV, column 5 elements received 200 uL of solution V, column 6 elements received 200 uL of solution VI, column 7 elements received 200 uL of solution VII, column 8 elements received 200 uL of solution VIII, column 9 elements received 200 uL of solution IX, column 10 elements received 200 uL of solution X, column 11 elements received 200 uL of solution XI. Solution XII was then added to all elements such that row 1 received 50 µL, row 2 received 40 µL, row 3 received 30 uL, row 4 received 20 uL and row 5 received 10 uL. The reactor block array was sealed using a teflon film covering a silicon rubber against an aluminum cap.

The array was then heated to 140° C. for 15 hr with agitation provided by an orbital shaker. The reaction block was allowed to cool, and to each vessel was added THF such that the total volume reached 0.8 mL, and the block was sealed and heated at 110° C. with orbital shaking for approximately 1 hr, to allow formation of uniform, fluid solution, and the reactor block was allowed to cool. This library of random copolymers of styrene and n-butylacrylate was expected to produce polymers with a range of molecular weights and compositions, which were tested with the following system.

Adsorption chromatography was used for separation of various components of the reaction mixtures that contained the comonomers, (co)polymers, solvents and catalyst components. Good separation was achieved in 60 seconds per sample using a short, high-aspect ratio reversed-phase column and gradient of THF in water with a concave profile. The specific gradient profile allows to separate small molecules with similar retention behavior from each other as well as elute a highly retained polymer in a very short time. Columns of various sizes, porosities and chemistries were used for this purpose including polystyrene-based monoliths and silica-based porous beads.

Combination of optimum column and mobile phase parameters leads to a much faster separation then experienced before and allows the technique to be used for characterization of the polymerization libraries. The best results were achieved with short cartridges packed with 10 µm octadecylsilica beads. The library of 96 polymer sample mixtures was analyzed in 144 min (including diluting samples, chromatography and saving the chromatograms)—demonstrating an average sample throughput of about 1.5 minutes per sample.

In this example, samples containing styrene, butylacrylate, (co)polymer, initiator and solvent at various concentrations were injected into a 30×4.6 mm precolumn cartridge RP-18 (Brownlee) equilibrated by 27% tetrahydrofuran at 10 mL/min. Then the percentage of tetrahydrofuran in mobile phase was changed using a concave gradient profile from 27 to 100% tetrahydrofuran. The chromatographic system used for this example was the same as that described in Example 3, however, equipped with a UV-VIS detector only. The solvent and monomers are eluted within a first few percent of tetrahydrofuran, polymer requires much higher percentage of tetrahydrofuran to be eluted. All five peaks representing the particular components of the mixtures were eluted within 60 seconds.

Example 14
Comparison of Rapid GPC and Conventional GPC

This example demonstrates correlation between rapid liquid chromatography (using a short, high-aspect ratio column) and conventional GPC.

The same synthetic procedure as in Example 8 was carried out using a robotic sampler in an inert atmosphere drybox, requiring approximately 20 min. to prepare the reaction array. Similar processing of the array was carried out as in Example 8.

Row six of the array was analyzed by RFLS as in Examples 5 and 9 to determine values of $M_w$. Row six was also analyzed by conventional GPC using two mixed bed columns (Polymer Labs, 7.5×300 mm mixed C PL-gel). THF was used as the eluant in both cases.

Comparisons of $M_w$ values obtained by both methods are shown by the following Table 17.

TABLE 17

Comparison of $M_w$ Values from RFLS and Conventional GPC

| Sample | RFLS ($M_w$, kD) | GPC ($M_w$, kD) |
| --- | --- | --- |
| 1 | 79.7 | 83.8 |
| 2 | 45.1 | 52.4 |
| 3 | 42.8 | 46.4 |
| 4 | 38.9 | N.D. |
| 5 | 39.7 | 45.7 |
| 6 | 37.4 | 40.3 |
| 7 | 37.2 | 41.9 |
| 8 | 34.9 | 39.9 |
| 9 | 35.5 | 38.4 |
| 10 | 33.9 | 34.2 |
| 11 | 34.3 | 37.4 |

As can be seen from this table, the rapid GPC protocols disclosed herein provide $M_w$ values in agreement with traditional GPC.

Example 15
Rapid Size Exclusion Chromatography

This example demonstrates the characterization of a plurality of polystyrene standards using rapid size exclusion chromatography. The sample-throughput was 2 minutes per sample.

Two short, high-aspect ratio columns (0.8 cm×3 cm) were employed in series. The first column was packed with Suprema Gel 30 Å and the second column was packed with Suprema Gel 1000 Å (Polymer Standard Service, Germany). The mobile-phase solvent was THF at a flowrate of 2 m/min. Sample preparation was the same as in Example 17. The polymer samples (20 µl) were serially injected at two minute intervals (without being overlaid). The separated samples or components thereof were detected with a UV-VIS detector at 220 nm.

Figure 11B:
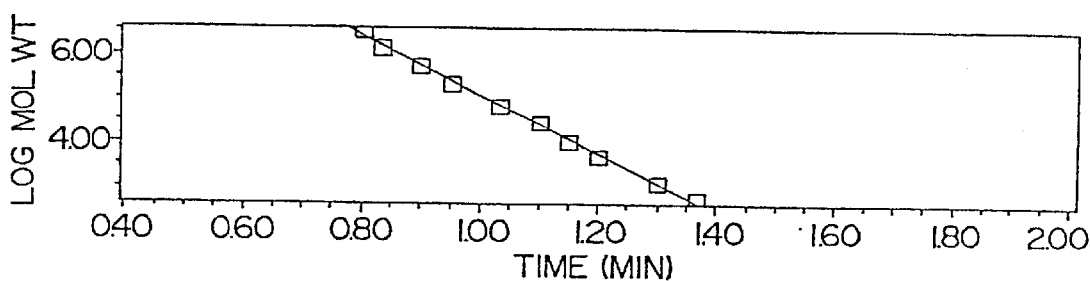
FIGS. 11A and 11B are graphs showing the results of Example 15.
Figure 11A:
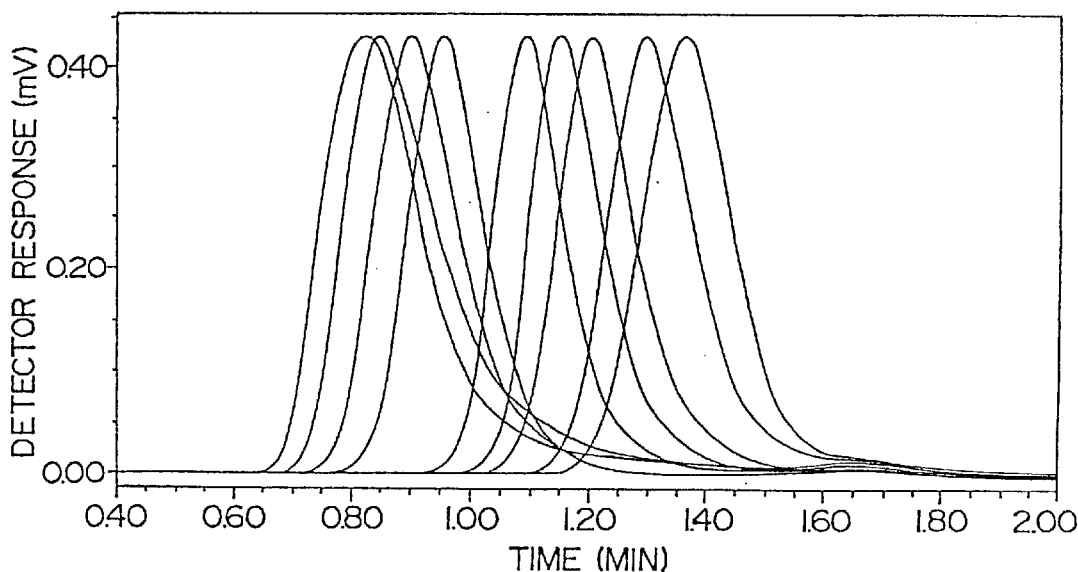

FIGS. 11A and 11B shows the results—overlaid as a single trace (FIG. 11A) and the corresponding calibration curve (FIG. 11B). Good linearity of the calibration curve is demonstrated.

Example 16
Rapid Size Exclusion Chromatography with Enhanced Resolution

This example demonstrates the characterization of a plurality of butyl rubber (polyisobutylene) samples using size exclusion chromatography with overlaid injection and enhanced resolution. The sample-throughput was 1½ minutes per sample.

A single, conventional chromatography column (0.75 cm×30 cm) was packed with PL Gel Mixed-B (Polymer Labs). The mobile-phase solvent was toluene at a flowrate of 4 ml/min. The system was calibrated using the indirect calibration polystyrene standards and protocols of Example 26. Sample preparation was the same as in Example 17. The polymer samples (50 µl) were serially injected at 90 second intervals (with overlaid injection). The separated samples or components thereof were detected with an ELSD detector at 120° C. and 7 l/min of air.

FIG. 12A through FIG. 12C show the data from the experiment. FIG. 12A shows the chromatographs of each of the samples—electronically overlaid on a single trace. The chromatograph for the "single-shot" indirect calibration standard is shown in FIG. 12B and the corresponding calibration curve is shown in FIG. 12C. Significantly, a relative high-molecular weight polyisobutylene was identified ($M_{peak}$=154,288; $M_w$=199,123; $M_n$=46,406; PDI~4.3) and distinguished from other, lower molecular weight samples.

Example 17
Rapid Size Exclusion Chromatography with Enhanced Resolution

This example demonstrates the characterization of a plurality of polyisobutylene samples using accelerated size exclusion chromatography with overlaid injection. The sample-throughput was 8 minutes per sample.

A series of three identical conventional chromatography column (0.75 cm×30 cm) were employed, each of which was packed with PL Gel Mixed-B (Polymer Labs). The mobile-phase solvent was toluene at a flowrate of 2 ml/min. The system was calibrated using polystyrene standards. Sample preparation (dilution, mixing) was effected on each succeeding sample while each preceding sample was being separated. The polymer samples (50 µl) were serially injected at 8 minute intervals (with overlaid injection). The separated samples or components thereof were detected with an ELSD detector at 120° C. and 7 l/min of air.

FIG. 13 is a representative chromatograph from one of the samples. As shown in FIG. 13, the representative sample comprised an earlier eluting polymer component ($M_{peak}$= 67,285; $M_w$=75,162; $M_n$=38,106; PDI~2.0) and a later eluting lower molecular-weight component ($M_{peak}$=1,736).

The same library of polymer samples was characterized a second time with the same liquid chromatography system except that the mobile phase was THF at 2 ml/min and the ELSD detector was at 50° C. and 7 l/min of air. Similar results (not shown) were obtained.

Example 18
Comparison of Rapid SEC, Enhanced Rapid SEC, and Accelerated SEC

This example demonstrates a comparison between three preferred embodiments of the invention: rapid size exclusion chromatography (SEC), rapid SEC with enhanced resolution and accelerated SEC. These embodiments differ, in general, with respect to sample throughput and, in some aspects, information quality, as explained below.

Example 18A
Comparison of Accelerated SEC and Rapid SEC

A combinatorial library of polystyrene polymer samples—prepared in emulsions with varying ratios of monomer to initiator—were characterized with two different liquid chromatography approaches: accelerated SEC and rapid SEC—adsorption chromatography.

The accelerated SEC liquid chromatography system was substantially similar to that described in Example 17, with a sample-throughput of 8 minutes per sample and with complete molecular weight determination ($M_{peak}$, $M_w$, $M_n$, PDI, and molecular weight distribution shape). The rapid SEC-adsorption liquid chromatography system was substantially similar to that described in Example 20, except with a sample-throughput of about 1–2 minutes per sample with limited molecular weight determination ($M_{peak}$, $M_w$, and estimate of PDI).

FIGS. 14A and 14B show the determined weight-average molecular weight for each of the samples of the library as characterized using the accelerated SEC (FIG. 14A) and the rapid SEC (FIG. 14B) systems. The weight-average molecular weight determined by these techniques is substantially the same—demonstrating that the rapid SEC system, operating with a throughput of about 1–2 minutes per sample, is rigorous for determination of $M_w$. The techniques varied, however, with respect to the accuracy of determined PDI values (data not shown).

Example 18B
Comparison of Accelerated SEC and Enhanced Rapid SEC

A combinatorial library of butyl rubber (polyisobutylene) polymer samples were prepared, and then characterized with two different liquid chromatography approaches: accelerated SEC and enhanced rapid SEC (also referred to herein as "rapid SEC with enhanced resolution").

The accelerated SEC liquid chromatography system was substantially similar to that described in Example 17, with a sample-throughput of 8 minutes per sample and with complete molecular weight determination ($M_{peak}$, $M_w$, $M_n$, PDI, and molecular weight distribution shape) and conversion determination. The rapid SEC liquid chromatography system was substantially similar to that described in Example 16, with a sample-throughput of about 1½ minutes per sample and with reasonably complete molecular weight determination ($M_{peak}$, $M_w$, and good estimate of PDI) and conversion determination.

FIGS. 15A through 15F show the resulting data. FIGS. 15A through 15C show the determined weight-average molecular weight (FIG. 15A), the determined polydispersity index (FIG. 15B) and the determined conversion (FIG. 15C) for each of the samples of the library as characterized using the accelerated SEC system. FIGS. 15D through 15F show the determined weight-average molecular weight (FIG. 15D), the determined polydispersity index (FIG. 15E) and the determined conversion (FIG. 15F) for each of the samples of the library as characterized using the enhanced rapid SEC system. Comparison of the results demonstrates that the determined weight-average molecular weight and the determined conversion are substantially the same for each of these techniques. Although differences can be observed between the determined values for the polydispersity indexes of the two characterizations systems, trends in PDI values are observable and substantially the same for the two characterization systems.

Example 19
Comparison of ELSD Detector and RI Detector

This example demonstrates a comparison between an evaporative light-scattering detector (ELSD), sometimes alternatively referred to as an evaporative mass detector (EMD), and a refractive index (RI) detector. More specifically, this example demonstrates the principle of using a low-molecular weight insensitive detector, such as an ELSD, for detection in liquid chromatography or flow injection analysis systems.

Figure 16A:
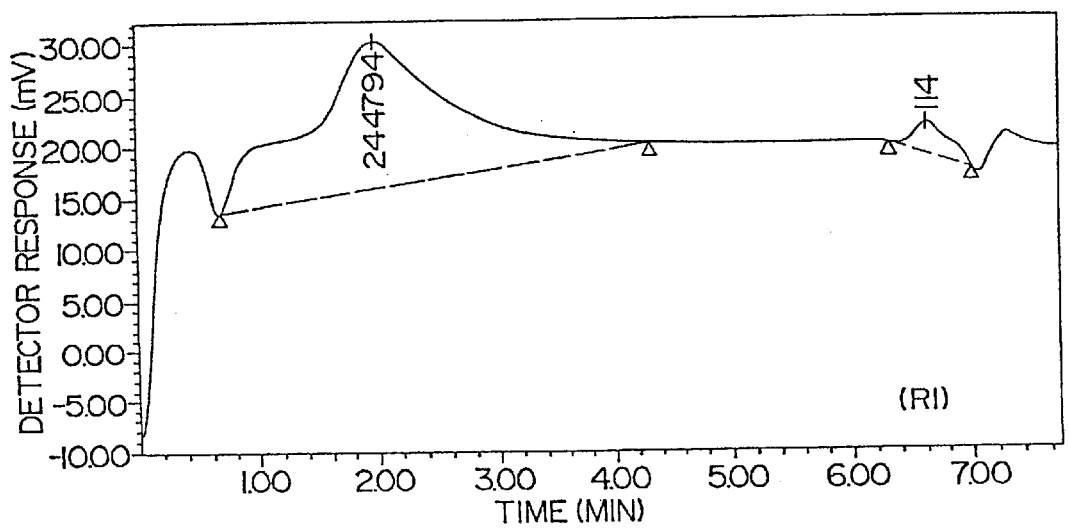
FIGS. 16A and 16B are graphs of detector response (mv) versus retention time (minutes) for a polymer sample characterized in two different liquid chromatography systems illustrated in Example 19. The systems were identical except with respect to the detector—one system employing a RI detector (FIG. 16A) and the other system employing an ELSD detector (FIG. 16B).
Figure 16B:
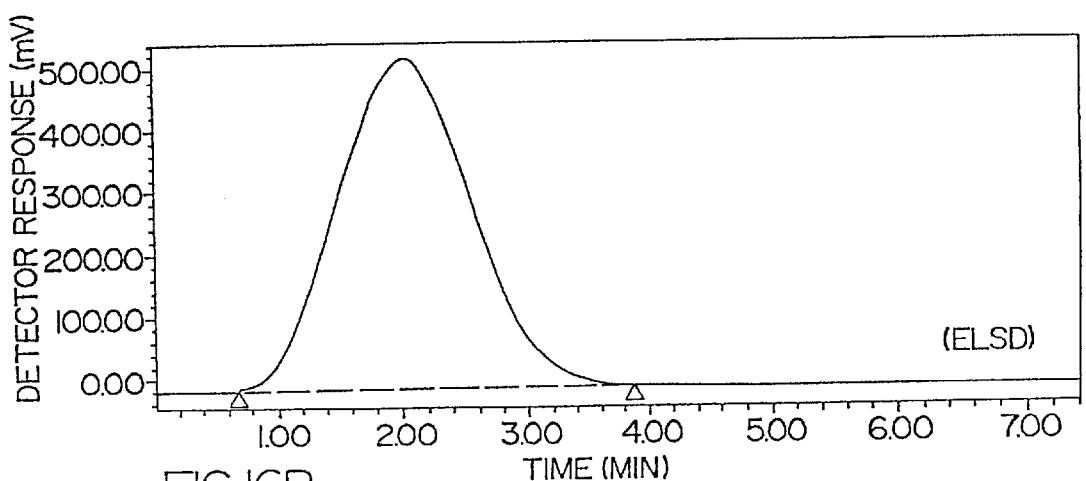

FIGS. 16A and 16B show chromatographic traces for the same polymer sample characterized in two different liquid chromatography systems that were identical except with respect to the detector—one system employing a RI detector and a second system employing an ELSD detector. Comparison of these traces (FIG. 16A, FIG. 16B) shows that the polymer sample had a relatively high-molecular weight component ($M_{peak}$=244,794) and a relatively low-molecular weight component ($M_{peak}$=114). Although both detectors characterized the relatively high-molecular weight component, the ELSD detector was insensitive to the relatively low-molecular weight component.

As discussed above, such insensitivity can be advantageously employed in connection with the invention, particularly with respect to serial overlaid injection of a preceding sample and a succeeding sample. Unlike the RI detector, the ELSD detector can detect the leading edge of the succeeding sample sooner, without interference from the trailing edge of the preceding sample.

Example 20
Rapid SEC—Adsorption Chromatography

This example demonstrates the characterization of a plurality of emulsion polymer samples using rapid size exclusion chromatography (SEC) in combination with adsorption chromatography to determine molecular weight and conversion. The sample-throughput was 2–3 minutes per sample.

Two short, high-aspect ratio columns (0.8 cm×3 cm) were employed in series. The first column was packed with Suprema Gel 30 Å and the second column was packed with Suprema Gel 1000 Å (Polymer Standard Service, Germany). The mobile-phase solvent was THF at a flowrate of 2 ml/min. Sample preparation was the same as in Example 17. The emulsion polymer samples (polystyrene, polymethylmethacrylate, polybutylacrylate and polyvinylacetate) were serially injected at 2–3 minute intervals (without being overlaid). The separated samples or components thereof were detected.

Figure 17A:
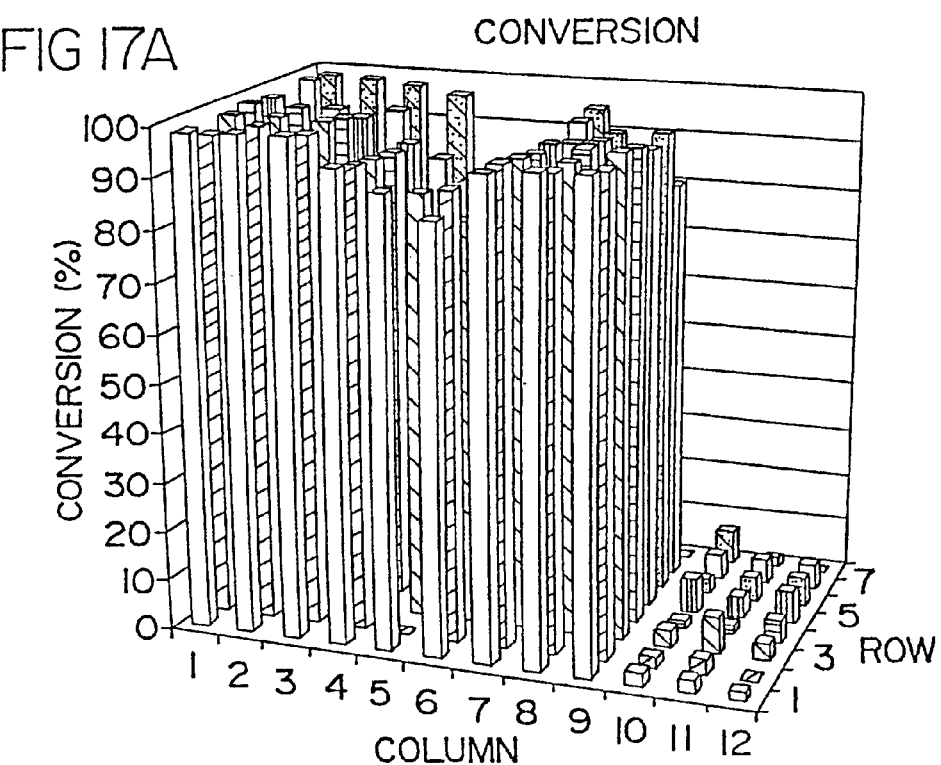
FIGS. 17A and 17B are three-dimensional bar graphs showing the determined conversion (FIG. 17A) and the determined weight-average molecular weight (FIG. 17B) for the polystyrene samples (columns 1–4), the polymethylmethacrylate samples (columns 4–6), the polybutylacrylate samples (columns 7–9) and the polyvinylacetate samples (columns 10–12) characterized with SEC-adsorption chromatography approaches illustrated in Example 20.
Figure 17B:
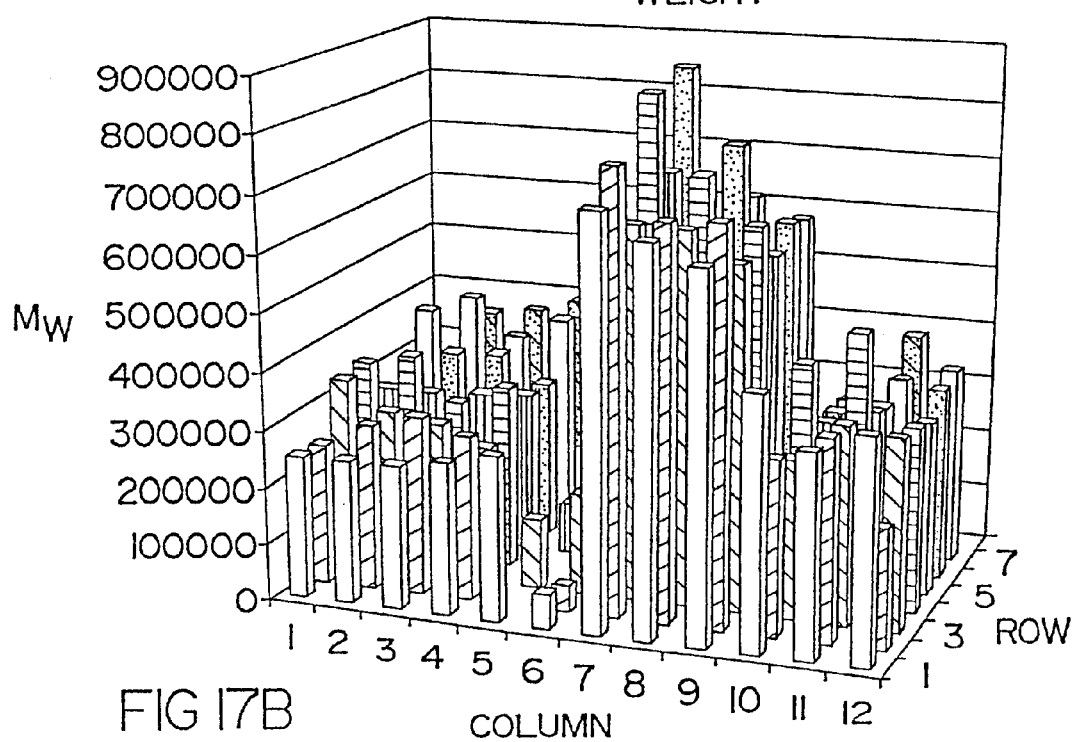

FIGS. 17A and 17B shows the determined conversion (FIG. 17A) and the determined weight-average molecular weight (FIG. 17B) for the polystyrene samples (columns 1–4), the polymethylmethacrylate samples (columns 4–6), the polybutylacrylate samples (columns 7–9) and the polyvinylacetate samples (columns 10–12). These data demonstrate that SEC-adsorption chromatography can be effectively employed to determine both molecular weight and conversion with high sample-throughput.

Example 21
High-Temperature Characterization of Polymers

This example demonstrates the characterization of a plurality of polystyrene and polyethylene calibration standards using high-temperature liquid chromatography.

The experimental set-up was substantially as shown in FIG. 6 and described in connection therewith and as follows. The auto-sampler 104' was located outside of a heated oven 112, and was equipped with a long, thermostatically-controlled heated probe 201 maintained at a temperature of 140° C. The heated probe was substantially as shown in FIG. 5A and described in connection therewith. The sample container 202 was likewise heated and maintained at a temperature of 140° C. The loading port 204, transfer line 206, injection valve 210, in-line filter (0.2 μl, not shown), and column 102 resided in the oven 112 and maintained at a temperature ranging from 140° C. to 160° C. The injection valve 210 was an eight-port valve substantially as shown in FIG. 3 and described in connection therewith, with each of the sample loops having a volume of about 200 μl. The column was a high-aspect ratio column (2.5 cm×5 cm) packed with PL Gel Mixed-B (Polymer Labs). For the experiments of Example 21A only, an in-line flow-splitter (not shown) was positioned after the column and the before the detector. The flow-splitter resided in the oven, and split the separated sample stream at a ratio of about 1:15 (detector:waste). For both examples 21A and 21B, an external ELSD detector resided outside of the heated oven 112, and was in fluid communication with the column 102 (or flow-splitter) by means of a heated transfer line.

The following commercially available calibration standards were serially introduced into the liquid chromatography system by serially withdrawing the samples from the sample container and delivering the samples through oven aperture 113 to the loading port 204:

| Polyethylene (nominal Mw) | Polystyrene (nominal Mw) |
|---|---|
| 1,230 | 1,370 |
| 2,010 | 4,950 |
| 16,500 | 10,900 |
| 36,500 | 29,000 |
| 76,500 | 68,600 |
| 91,500 | 215,000 |
| 145,500 | 527,000 |
|  | 1,253,000 |
|  | 3,220,000 |

Example 21A
Rapid Size-Exclusion Chromatography—First Conditions

In a first experiment, molecular weight was determined with a sample-throughput of 70 seconds per sample.

Briefly, the mobile-phase solvent was trichlorobenzene at a flowrate of 9 ml/min. Sample preparation (dissolution in trichlorobenzene) was effected on each succeeding sample while each preceding sample was being separated. The polymer samples were serially injected at 70 second intervals (with overlaid injection). The transfer line for transferring the samples to the ELSD was maintained at about 165° C. The samples or components thereof were detected with an ELSD detector at 180° C. (nebulizer temperature)/250° C. (evaporator temperature) and 1.8 l/min of nitrogen.

Figure 18B:
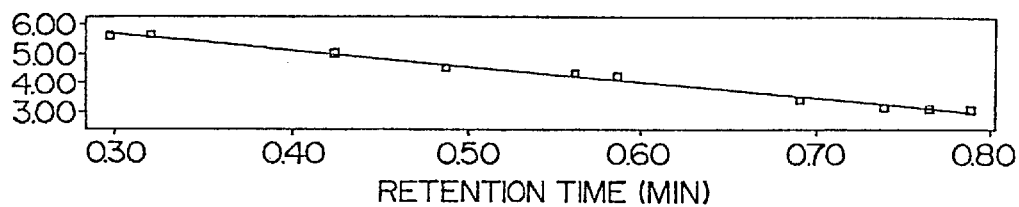
FIGS. 18A and 18B show the results of high-temperature characterization experiments of Example 21A.
Figure 18A:
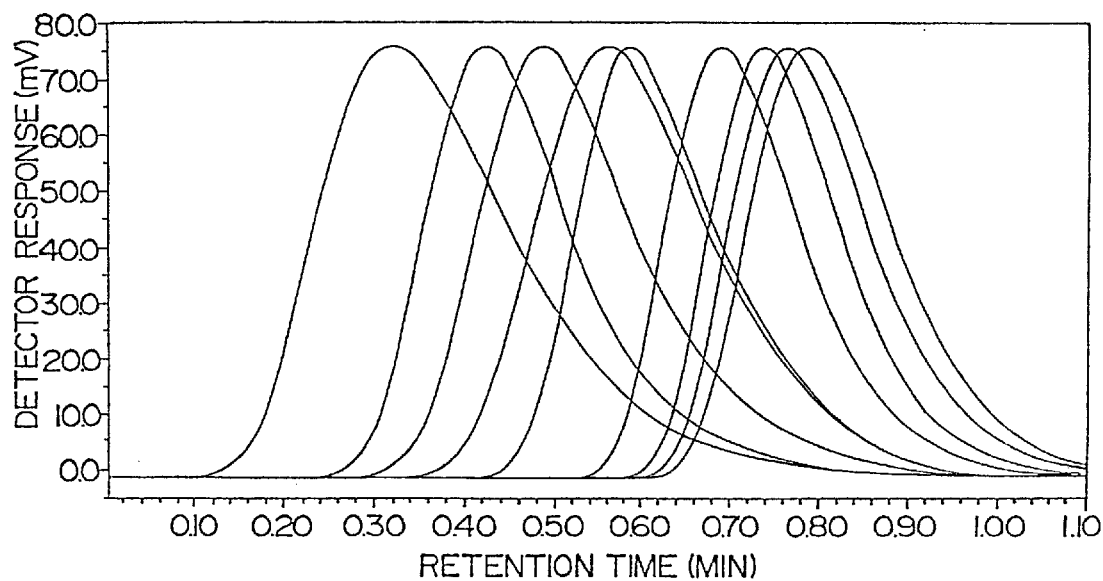

FIGS. 18A and 18B show the results as a chromatograph for the polystyrene standards overlaid as a single trace (FIG. 18A) and as a calibration curve for representative polyethylene standards (FIG. 18B). Linearity of the calibration curve is demonstrated.

Example 21B
Rapid Size-Exclusion Chromatography—Second Conditions

In a second experiment, molecular weight was determined with a sample-throughput of 2¼ minutes per sample.

Briefly, the mobile-phase solvent was o-dichlorobenzene at a flowrate of 10 ml/min. Sample preparation (dissolution in trichlorobenzene) was effected on each succeeding sample while each preceding sample was being separated. The polymer samples were serially injected at 2.2 minute intervals (without overlaid injection). The transfer line for transferring the samples to the ELSD was maintained at about 160° C. The samples or components thereof were detected with an ELSD detector at 160° C. (nebulizer temperature)/250° C. (evaporator temperature) and 2.0 l/min of nitrogen.

Figure 19B:
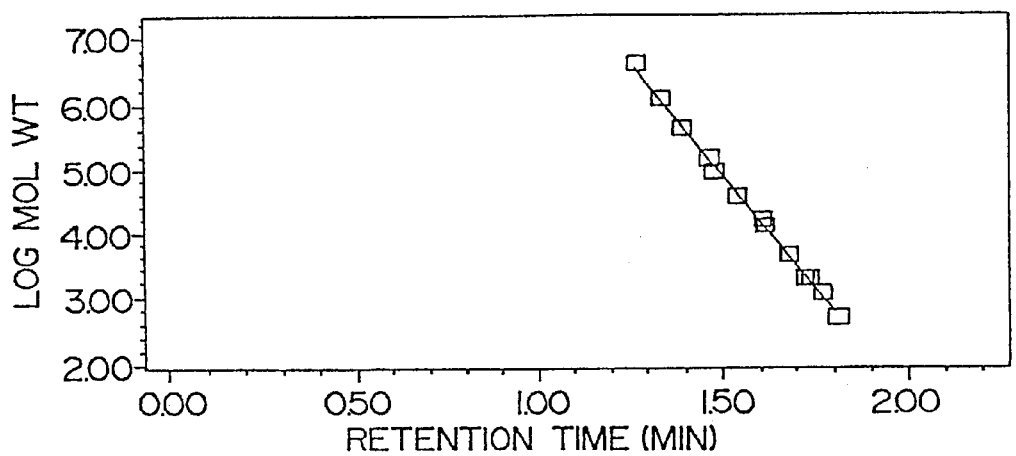
FIGS. 19A and 19B show the results of high-temperature characterization experiments of Example 21B.
Figure 19A:
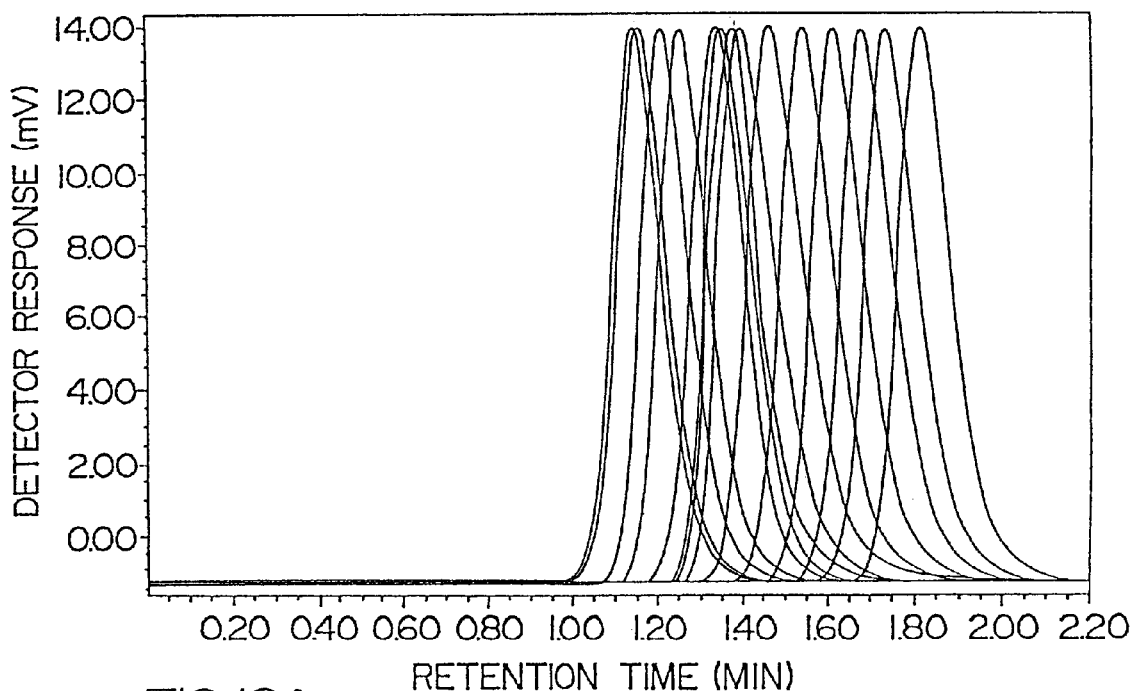

FIGS. 19A and 19B show the results as a chromatograph for representative polystyrene standards and polyethylene standards overlaid as a single trace (FIG. 19A) and as a calibration curve for representative polyethylene standards (FIG. 19B). Linearity of the calibration curve is demonstrated.

Example 22
High-Temperature HPLC with Mobile-Phase Temperature Gradient

This example demonstrates the principle for high-temperature characterization of a polyethylene polymer sample using liquid chromatography with a mobile-phase temperature gradient.

A single, short, high-aspect ratio column (0.8 cm×5 cm) contained a polystyrene monolith as the separation medium and resided in a PL-210 HT-GPC oven maintained at 140° C. The system was configured substantially as shown in FIG. 6 and described in connection therewith and as follows. Two mobile-phase reservoirs 114, 120 were provided and equipped with two Waters 515 pumps 116, 118. A "mobile-phase A" reservoir 114 feeding pump 116 (hereinafter "pump A") comprised trichlorobenzene (TCB) and, in operation, was configured to pump mobile-phase A through the injection valve 210 (100) and through the oven, whereby the mobile-phase A was heated to become the hot mobile phase (i.e., hot TCB). A "mobile-phase B" reservoir 120 feeding pump 118 (hereinafter "pump B" ) also comprised trichlorobenzene, and in operation, was configured to pump mobile-phase B to bypass most of the heated environment, and to enter the oven immediately prior to the column 102 as an essentially ambient-temperature mobile phase (i.e., cold TCB). Detection was effected with a PD 2000 light-scattering detector (90°).

In a first experiment, a polyethylene polymer sample ($M_w$=30,000) was introduced into the system with mobile-phase A (only) at a flow rate of 3 ml/min, such that the sample entered the column with the hot TCB mobile phase. The mobile-phase was maintained as the hot TCB during the entire experiment.

In a second experiment, a polyethylene polymer sample ($M_w$=30,000) was introduced into the system with mobile phase initially configured as mobile-phase B at a flow rate of 3 ml/min, such that the sample entered the column with the cold TCB mobile phase. The mobile-phase was maintained as the cold TCB for two minutes, at which time the system was reconfigured to switch to mobile-phase B at 3 ml/min such that the sample was eluted shortly thereafter with hot TCB—essentially effecting a mobile-phase temperature step-gradient (from cold TCB to hot TCB).

FIG. 20 shows the chromatograph—superimposed (overlaid) for the first and second experiments. Comparison of the two traces demonstrates that elution of the polyethylene sample was effectively controlled by controlling the temperature of the mobile phase. Hence, mobile-phase temperature gradients can be employed in connection with the high-temperature characterization of polymers.

Example 23
Very Rapid Flow-Injection Light-Scattering

This example demonstrates the characterization of polymer library using a very rapid flow-injection light-scattering (FILS) system. The sample throughput was 8 seconds per sample. This example also demonstrates the advantage of using a low-molecular weight insensitive detector, particularly an ELSD, over a static light-scattering (SLS) detector (90°) in such a FILS system. This example demonstrates, moreover, that the data from an entire 96-member library of polymer samples can be collected, processed and then stored in a single data file.

Figure 7C:
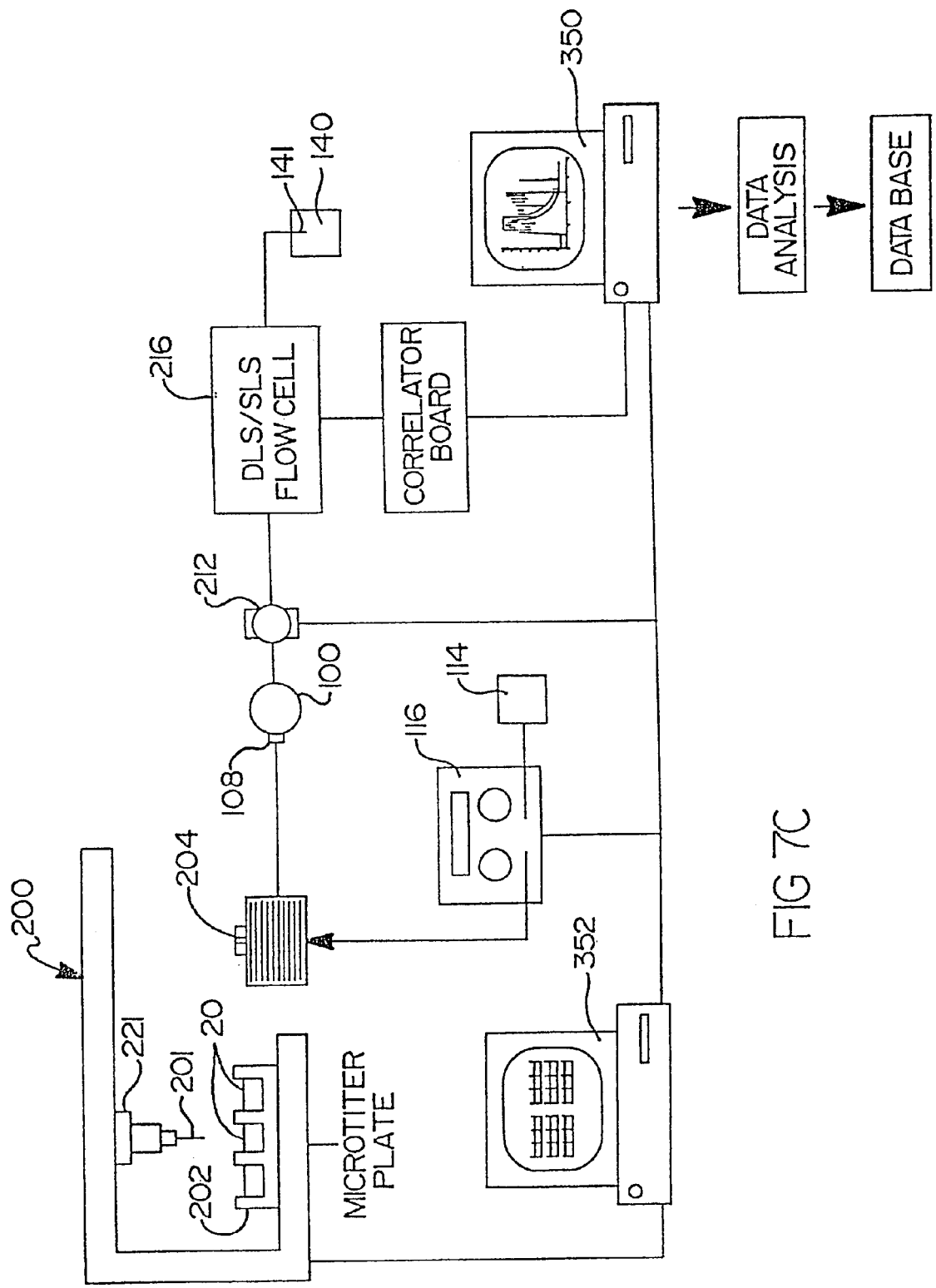
Figure 7D:
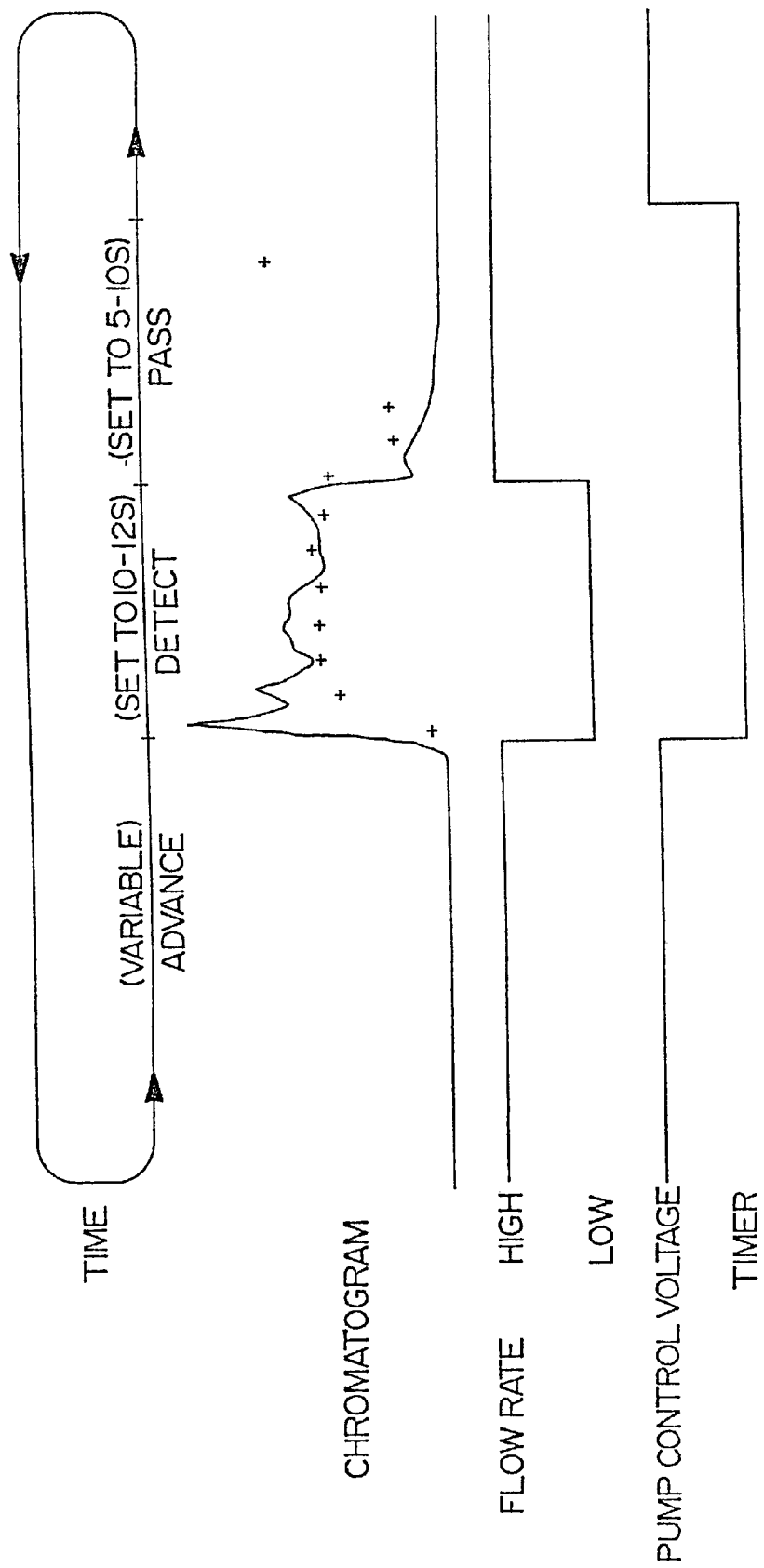

A 96-member polymer library was introduced into a flow-injection light-scattering system configured substantially as shown in FIG. 7C and described in connection therewith—with a 0.2 µl in-line filter in place, but no chromatographic column. The polymer samples were serially injected at intervals of 8 seconds into a methyl-tert-Butyl Ether mobile phase at a flow rate of 4 ml/min.

In a first experiment, the polymer samples were detected with a 90° SLS (using Wyatt's MiniDawn). In a second experiment, the polymer samples were detected with an ELSD (PL-1000) at 50° C. and 1.5 l/min gas flowrate. In both the first and second experiments, the data for the entire polymer library (96 samples) was collected and stored as a single data file (in about 13 minutes total cumulative time).

Figure 21A:
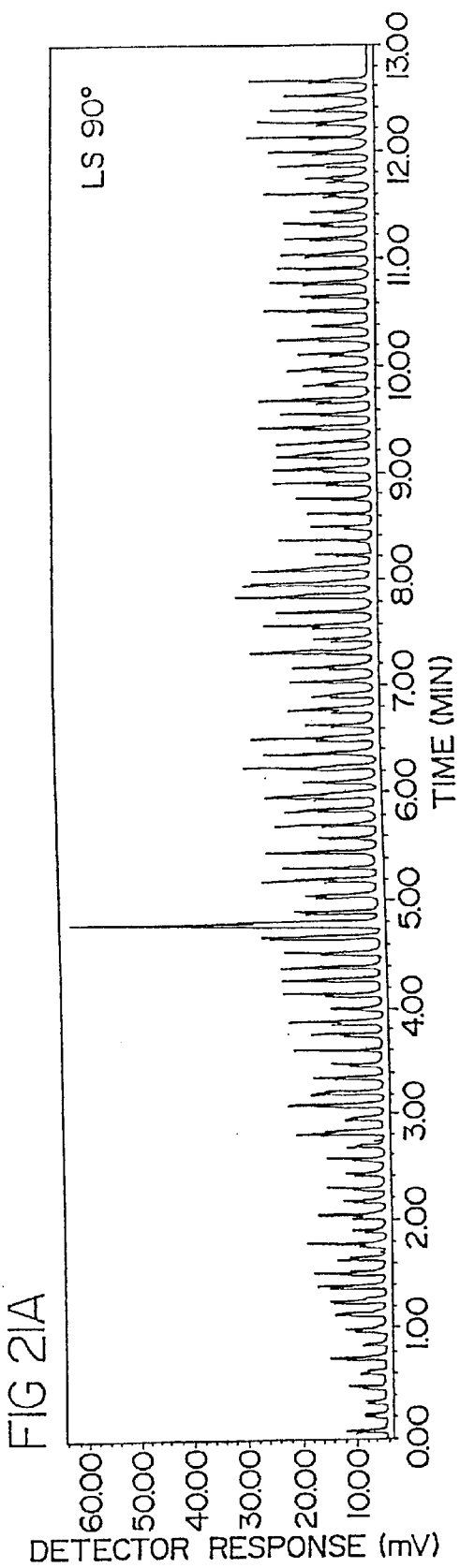
FIGS. 21A and 21B are graphs of detector response (mv) versus retention time (minutes) and show the resulting chromatographs for the characterization of 96 polymer samples using the SLS detector (FIG. 21A) and the ELSD (FIG. 21B) in the very rapid flow-injection light-scattering approach illustrated in Example 23.
Figure 21B:
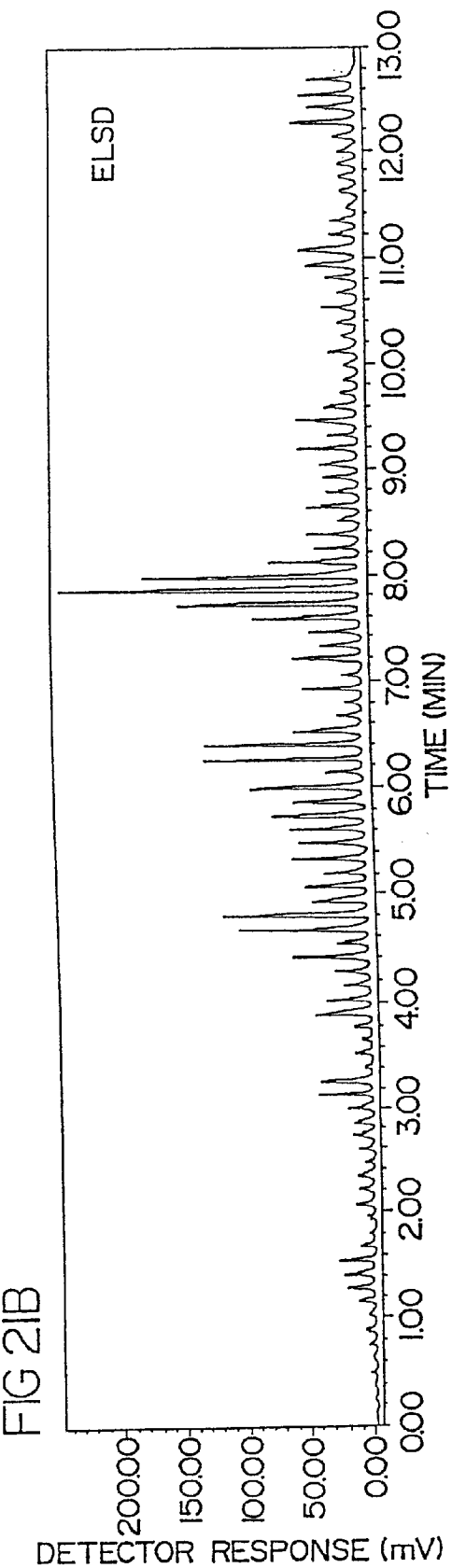

FIGS. 21A and 21B show the resulting chromatographs for the 96 polymer samples using the SLS detector (FIG. 21A) and the ELSD (FIG. 21B). Comparison of these chromatographs demonstrates that the ELSD was able to differentiate between various polymer samples of the library with a sample-throughput of 8 seconds per sample.

Example 24
Variable-Flow Light-Scattering

This example demonstrates variable-flow light scattering approaches for characterizing a library of methacrylate emulsion polymers prepared by batch free-radical emulsion polymerization. The sample-throughput was 35 seconds per sample.

The flow-injection analysis system was substantially as shown in FIG. 7C and described in connection therewith. Specifically, the system included an eight-port injection valve 210 (Valco Instruments), an HPLC pump 116 (Waters 515), stainless steel capillaries, an in-line filter 212 (2 µm, Valco Instruments), and a combined SLS/DLS/RI flow-through detector (Precision Detectors, PD2000/QELS)—with no chromatographic column.

The system was calibrated with monodisperse PS latex standards having $R_h$ of 9.5, 25, 51, and 102 nm in ultrapure water (Duke Scientific, Palo Alto, Calif.).

The emulsion samples were prepared (substantially in the manner described in Example 17) by dilution with ultrapure water to a concentration of about 0.001 wt % using an auto-sampler substantially as shown in FIG. 4 and described in connection therewith. The emulsion polymer samples (20 µl) were serially injected into an ultra-pure water mobile phase at intervals of 35 seconds. The mobile-phase flow rate was controlled by the pump 116 which, in turn, was controlled by microprocessors 350, 352, to provide an advancing flowrate, $V_{ADVANCE}$ of 1.5 l/min that advanced the sample into the detection cavity of the light-scattering cell very rapidly—within about a few seconds. The static light-scattering detector signal was monitored as an indication of the leading edge of the sample entering the detection cavity. An increase of the static light-scattering detector signal to 2.5 V above the baseline voltage caused the microprocessor to reduce the flowrate of the mobile phase to a detection flow rate $V_{DETECT}$ of 0.1 ml/min, which was subsequently maintained for a detection period of 15 seconds.

During this detection period, dynamic light-scattering measurements were taken at a temperature of 35° C. using the correlator board of the PD2000/QELS instrument (Software NTP32, version 0.98.005) as follows: 10 μsec sampling times; dilation factor of 4; and a total measurement time of 1.5 seconds per data point. Hence, 10 independent measurements of $R_h$ were taken per sample during the 15 second detection period.

Following the detection period, the flow-rate was increased to a passing flowrate, $V_{PASS}$ of 1.5 l/min—the same as the advancing flowrate, $V_{ADVANCE}$ for a period of about 15 seconds. The whole cycle, represented schematically in FIG. 7D, was then repeated for each of the polymer samples.

The post-acquisition data analysis and processing for the polymer library was performed automatically. To ensure that measurements corresponded to a particular sample in the detection cavity (i.e., in the scattering volume), measurements taken during the detection period are only considered for further processing and analysis when the SLS signal clearly exceeds the aforementioned baseline voltage. From those considered measurements, the first 3 measurements taken during the detection period were discarded to ensure that uniform flow-conditions had been established with respect to the processed data. The $R_h$ for a single measurement point for the sample were then determined by averaging the remaining 7 individual measurements and removing erroneous spikes and noise, where applicable.

The determined hydrodynamic radius $R_h$ (nm) for each of the members of the emulsion library are shown in Table 18.

as a single-shot standards for polyisobutylene were developed as follows.

A set of nine commercially available polyisobutylene standards having known molecular weights were individually and serially characterized with the liquid chromatography system (in toluene and under the same conditions) to determine the retention time of the individual standards. The nine polyisobutylene standards and their corresponding (known) molecular weight were:

Polyisobutylene Standards ($M_{peak}$)
(1) 1000
(2) 4,000
(3) 9,500
(4) 26,000
(5) 67,000
(6) 202,500
(7) 539,500
(8) 1,300,000
(9) 3,640,000

After all of the standards had been run individually through the system (nine runs total), the data was assembled to form an absolute polyisobutylene (PIB) calibration based on the individual runs. FIG. 23A shows the individually determined retention-time data plotted against the corresponding known molecular weight—referred to herein as an "absolute" or "direct" polyisobutylene (PIB) calibration curve. The data for each of the PIB standards ((1) through (9)) are labeled on the chromatograph.

A set of commercially available polystyrene standards having known molecular weights were then evaluated with the same system under the same conditions (data not shown). Those polystyrene standards having retention times

TABLE 18

Determined Average $R_h$ (nm) for Emulsion Library

|   | 1 | 2 | 3 | 4 | 5 | 6 | 7 | 8 | 9 | 10 | 11 | 12 |
|---|---|---|---|---|---|---|---|---|---|----|----|----|
| A | 40.3 | 43.8 | 48.3 | 50.6 | 50.4 | 56.5 | 56.6 | 56.6 | 54.1 | 56.9 | 56.9 | 61.6 |
| B | 48.3 | 51.8 | 52.5 | 53.4 | 54.0 | 55.4 | 54.7 | 53.8 | 59.4 | 59.8 | 50.9 | 48.7 |
| C | 53.1 | 53.8 | 54.2 | 54.2 | 55.9 | 55.0 | 56.4 | 61.0 | 55.1 | 52.4 | 47.2 | 48.2 |
| D | 52.6 | 53.9 | 56.1 | 55.4 | 56.0 | 60.7 | 57.6 | 56.0 | 48.9 | 50.7 | 49.4 | 47.8 |
| E | 56.3 | 55.7 | 56.4 | 56.9 | 55.5 | 57.7 | 54.8 | 52.4 | 51.4 | 50.9 | 48.7 | 49.3 |
| F | 56.7 | 56.5 | 57.2 | 62.4 | 55.3 | 54.0 | 52.2 | 51.9 | 53.0 | 49.9 | 50.2 | 49.4 |
| G | 56.8 | 59.7 | 59.3 | 57.9 | 54.5 | 52.9 | 50.3 | 48.4 | 48.8 | 46.7 | 51.3 | 50.1 |
| H | 63.3 | 61.5 | 58.7 | 58.9 | 52.7 | 52.4 | 52.4 | 49.1 | 50.3 | 48.8 | 47.6 | 48.4 |

Example 25
Single-Shot Indirect Calibration

This example demonstrates single-shot indirect calibration of a liquid chromatography system.
Conventional Commercially-Available Calibration Standards FIG. 22A shows the chromatograph resulting from single-shot calibration using eight pooled, commercially-available polyisobutylene standards (FIG. 22A).

Figure 22A:
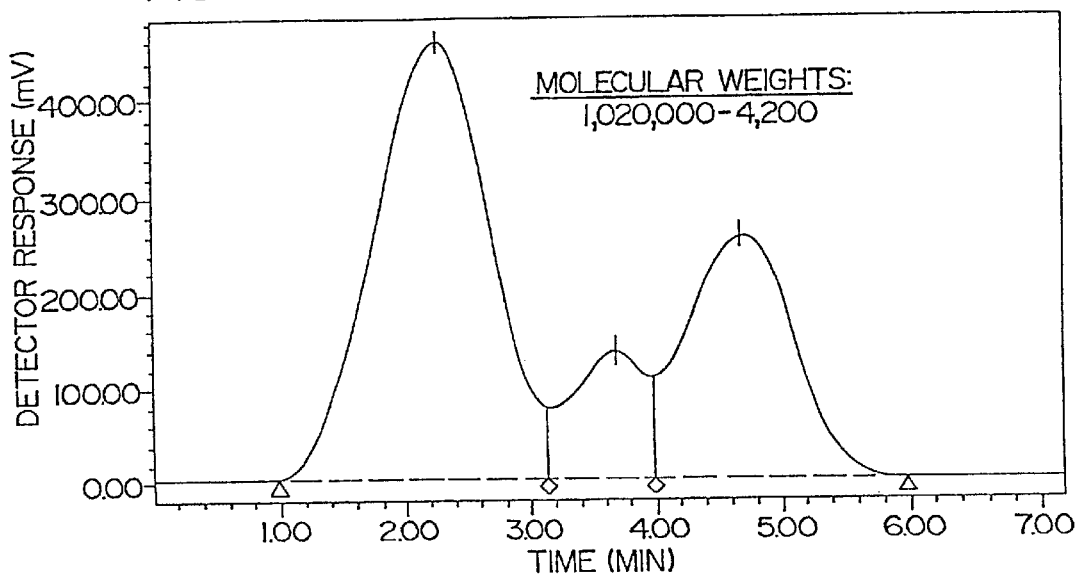
FIGS. 22A and 22B are graphs of detector response (mv) versus retention time (minutes) and are chromatographs for single-shot calibration using eight pooled, commercially-available polyisobutylene (PIB) standards (FIG. 22A), and for eight pooled, particularly-selected polystyrene standards having hydrodynamic volumes that are substantially the same as the hydrodynamic volumes for the PIB standards (FIG. 22B), as determined in Example 25.

Although the commercially available standards employed were each considered to be and were sold as "narrow-band"standards, FIG. 22A demonstrates that the polyisobutylene standards could not be effectively employed in single-shot (pooled standard) calibration. As shown therein, the chromatograph shows only three broad peaks—without resolution of at least five of the polyisobutylene standards.
Single-Shot Calibration Standards for Polyisobutylene Because a single-shot calibration is generally advantageous with respect to system accuracy, expense and speed, a set of polystyrene standards suitable for use, when pooled, that were substantially the same as the retention times for the nine PIB standards were selected, with the resulting correlation being as follows:

| Polyisobutylene Standards ($M_{peak}$) | | Selected Polystyrene Standards ($M_{peak}$) | |
|---|---|---|---|
| (1) | 1000 | (1) | 1,350 |
| (2) | 4,000 | (2) | 4,950 |
| (3) | 9,500 | (3) | 10,850 |
| (4) | 26,000 | (4) | 28,500 |
| (5) | 67,000 | (5) | 70,600 |
| (6) | 202,500 | (6) | 214,500 |
| (7) | 539,500 | (7) | 520,000 |
| (8) | 1,300,000 | (8) | 1,290,000 |
| (9) | 3,640,000 | (9) | 3,220,000 |

Figure 22B:
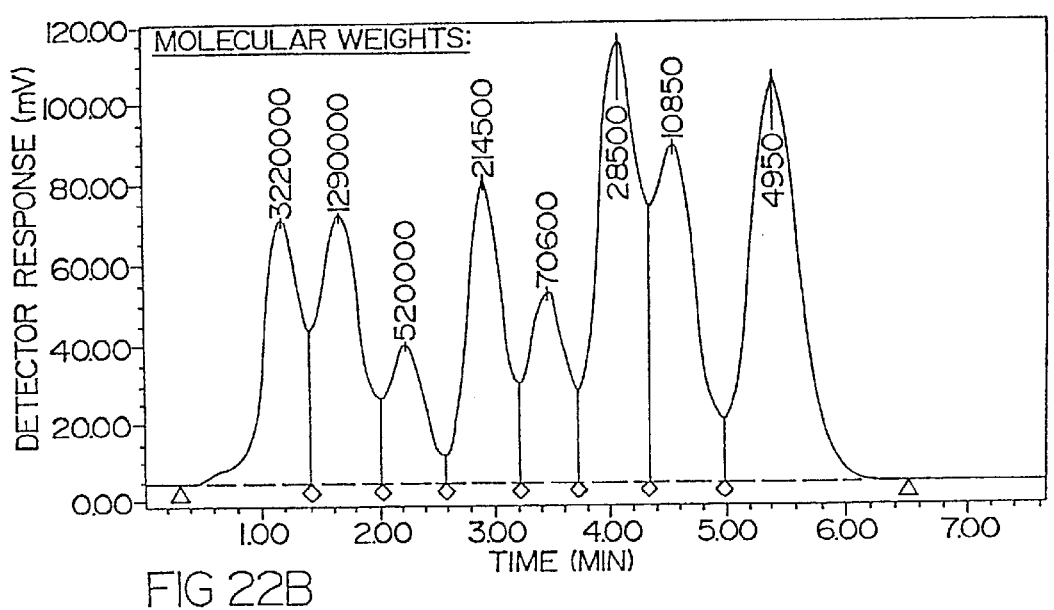

A set of eight of the nine selected polystyrene (PS) standards were then pooled to form a set of polystyrene standards (the small molecular weight standard being omitted), that were, effectively, a composition suitable for single-shot indirect calibration for polyisobutylene. These pooled PS standards were then characterized with the chromatography system with the same conditions. FIG. 22B shows the resulting chromatograph for the set of eight, pooled polystyrene standards that correspond to (i.e., have the same hydrodynamic volume as) the PIB standards of known molecular weight. As expected, the indirect PS standards for PIB are readily resolved by the chromatographic system. Significantly, however, these well-resolved samples are hydrodynamic-volume equivalents of the eight PIB standards that could not be resolved by the system when loaded as a single shot. (See FIG. 22A, and compare to FIG. 22B).

The aforementioned steps were repeated in substantially the same manner with the same system for a second set of polyisobutylene standards of known (different) molecular weights.

An indirect PIB calibration curve was then formed, by plotting the retention time determined from the single-shot run with the pool of the selected polystyrene standards—against the molecular weight of the corresponding polyisobutylene standards. FIG. 23B shows the indirect PIB calibration curve. Comparison of FIG. 23A (absolute PIB calibration curve) and FIG. 23B (indirect PIB calibration curve) demonstrates that the calibration curve determined from the single-shot indirect calibration standards for polyisobutylene is equivalent to the calibration curve laboriously derived from the serial direct calibration of the PIB standards.

Example 26
Parallel Characterization of Polymers with Dynamic Light Scattering

This example demonstrates the characterization of a 96-member library of emulsion polymers in a parallel manner—using a plurality of dynamic light-scattering (DLS) detector probes. Because the number of DLS probes was less than the total number of samples, the library was evaluated in a serial-parallel (i.e., semi-parallel) manner. The average sample-throughput for characterizing the entire library in this manner was about 5–15 seconds per sample.

The emulsion library was the same as used in connection with Example 24, and was prepared (diluted) as described therein. No filtering was performed on the dispersion before the measurements.

Figure 24:
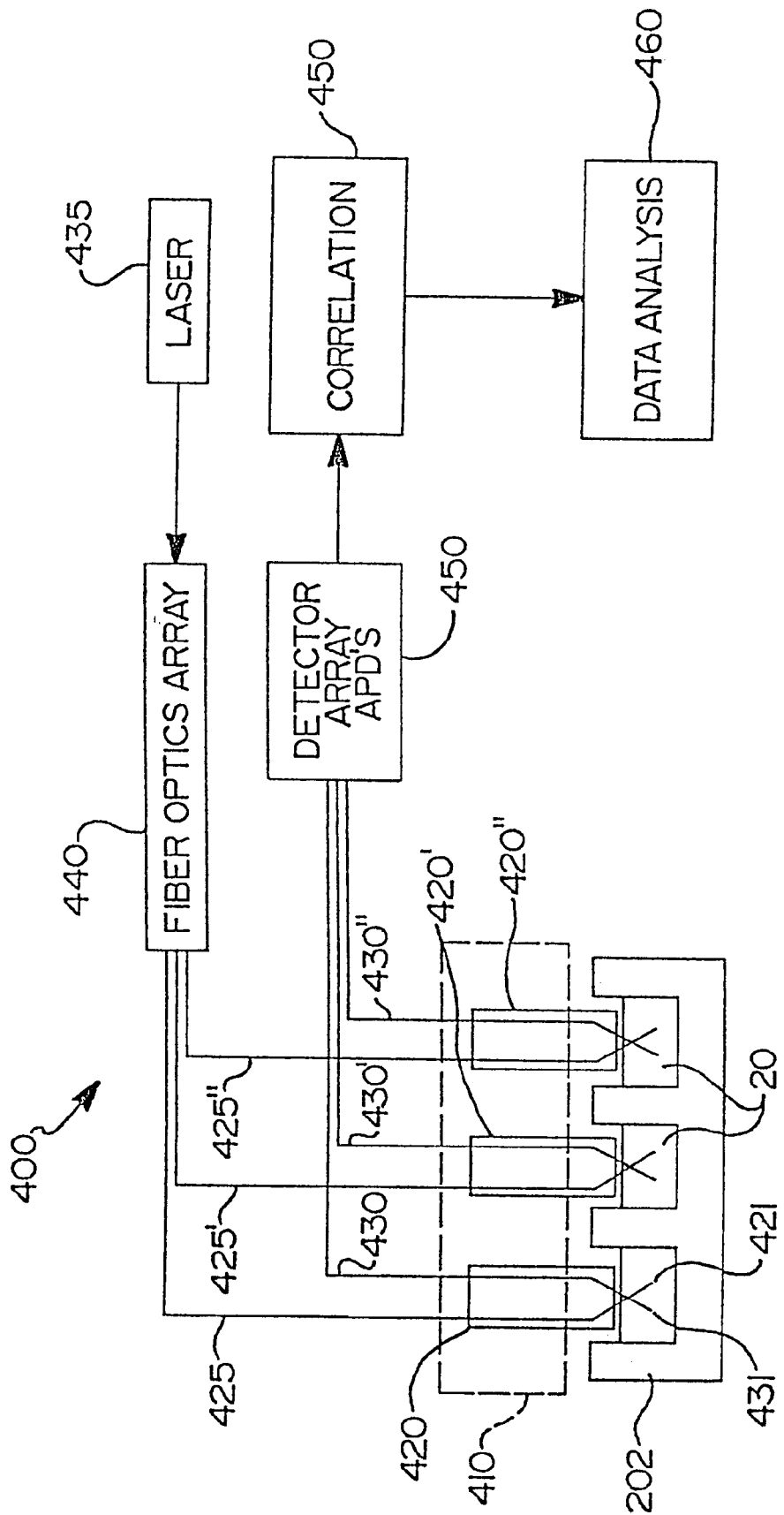
FIG. 24 is a schematic diagram illustrating a parallel, non-flow, non-immersion dynamic light-scattering (DLS) polymer characterization system.

A parallel DLS system used for characterizing the library of polymer samples was configured substantially as shown in FIG. 24 and described in connection therewith. Briefly, the system comprised an array 410 of two DLS probes 420 supported in parallel by a common support structure. Each probe 420 included a transmitting optical fiber 425, 425' and a receiving optical fiber 430, 430'.

Two single-mode fiber couplers, also referred to as optics (not shown), were used for transmitting an incident light and collecting a scattered light. These couplers consisted of a gradient refractive index (GRIN) lens aligned to a single-mode optical fiber. (Such couplers are typically used for coupling the output of a laser diode into an optical fiber.). For the DLS application, a focal length of 10 mm for both source and detector optics were chosen. The optics were mounted at an angle of 45 degrees with respect to each other giving a measurement angle of 135 degrees.

A HeNe laser 435 provided laser light at 632.8 nm wavelength (5 mW, Melles Griot). The laser light was coupled into the transmitting optical fiber in the fiber-optics array 440 and delivered into the sample 20 by the first optic. The scattered light was collected by the second optic. Unlike the immersed-probe configuration shown in FIG. 24, the measurements were done in a non-immersion, non-contact mode by mounting the probes approximately 5 mm above the liquid surface, such that the laser beam was delivered and the scattered light was collected through the liquid surface.

The scattered light collected by the second optic was coupled into the receiving optical fiber. The receiving optical fiber was connected to an avalanche photodiode (SPCM, EG&G, Canada). Measurements were performed at a temperature of 21° C. The measurements and photon autocorrelation were taken in a serial manner with a data acquisition time of 5 seconds per sample using a commercial autocorrelator board (ALV 5000/E, ALV GmbH Langen, Germany). The autocorrelation function was analyzed by a second order cumulant analysis (ALV Software, Version 2.0) and the hydrodynamic radius $R_h$ and the polydispersity index (PDI) were determined.

These data are presented in Tables 19 and 20, respectively. A comparison of Table 19 with Table 18 (Ex. 24) demonstrates that the average hydrodynamic radii determined by this parallel DLS, non-immersion detection approach correlate well with those values determined by variable flow-injection analysis.

Including time for positioning the sample under the probe, the total measurement took between 5 and 15 seconds per well.

TABLE 19

Determined Average $R_h$ (nm) for Emulsion Polymer Library

| | 1 | 2 | 3 | 4 | 5 | 6 | 7 | 8 | 9 | 10 | 11 | 12 |
|---|---|---|---|---|---|---|---|---|---|---|---|---|
| A | 38.8 | 40.4 | 45.9 | 46.4 | 49.5 | 48.9 | 50.1 | 56.2 | 50.1 | 51.9 | 53.2 | 54.8 |
| B | 43.8 | 48.1 | 52.7 | 50.6 | 50.9 | 52.5 | 52.1 | 51.3 | 54.8 | 55.8 | 48.5 | 45.2 |
| C | 48.5 | 50.4 | 51.8 | 50.3 | 53.2 | 51.2 | 54.1 | 59.2 | 54.3 | 49.3 | 48.3 | 47.2 |
| D | 50.5 | 52.2 | 52.9 | 51.7 | 52.9 | 58.1 | 59.2 | 53.9 | 49.1 | 50.8 | 48.6 | 46.2 |
| E | 56.0 | 53.6 | 54.7 | 55.0 | 58.7 | 56.3 | 52.6 | 48.6 | 47.0 | 49.1 | 47.5 | 48.4 |
| F | 51.0 | 54.2 | 56.2 | 61.0 | 54.2 | 50.9 | 50.9 | 52.2 | 49.0 | 50.3 | 46.8 | 48.2 |
| G | 53.8 | 55.5 | 56.3 | 53.6 | 53.1 | 52.8 | 49.4 | 45.6 | 48.9 | 43.8 | 45.7 | 48.2 |
| H | 58.2 | 56.1 | 54.8 | 55.1 | 50.7 | 49.1 | 49.4 | 47.1 | 49.6 | 44.7 | 44.4 | 46.3 |

TABLE 18

Determined PDI (cumulant analysis) for Emulsion Polymer Library

|   | 1 | 2 | 3 | 4 | 5 | 6 | 7 | 8 | 9 | 10 | 11 | 12 |
|---|---|---|---|---|---|---|---|---|---|----|----|----|
| A | 0.08 | 0.08 | 0.03 | 0.03 | 0.01 | 0.09 | 0.08 | 0.06 | 0.06 | 0.02 | 0.11 | 0.05 |
| B | 0.09 | 0.14 | 0.25 | 0.11 | 0.15 | 0.07 | 0.15 | 0.13 | 0.04 | 0.04 | 0.02 | 0.12 |
| C | 0.08 | 0.01 | 0.01 | 0.01 | 0.06 | 0.07 | 0.05 | 0.11 | 0.02 | 0.02 | <0.01 | 0.06 |
| D | 0.06 | 0.08 | 0.03 | 0.09 | 0.06 | 0.02 | 0.12 | 0.09 | 0.05 | 0.01 | <0.01 | 0.08 |
| E | 0.09 | 0.08 | 0.03 | 0.03 | 0.13 | 0.04 | 0.01 | 0.01 | 0.02 | 0.06 | 0.01 | 0.02 |
| F | <0.01 | 0.03 | 0.03 | 0.08 | 0.07 | 0.03 | 0.04 | 0.03 | 0.11 | 0.06 | 0.04 | 0.07 |
| G | 0.08 | 0.08 | 0.06 | 0.06 | 0.06 | 0.09 | 0.05 | <0.01 | 0.09 | 0.10 | 0.12 | 0.09 |
| H | 0.05 | 0.06 | 0.01 | 0.06 | 0.05 | 0.05 | 0.10 | 0.01 | 0.15 | <0.01 | 0.14 | 0.09 |

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

We claim:

1. A liquid chromatography system for characterizing a polymer sample, the system comprising
    an enclosure defining a heated environment, the heated environment being maintained at a temperature of not less than about 75° C.,
    a chromatographic column residing in the heated environment, the chromatographic column comprising a stationary phase within a separation cavity, an inlet port for receiving a mobile phase and a polymer sample to the separation cavity, and an effluent port for discharging the mobile phase and the polymer sample or separated components thereof from the separation cavity,
    an injection valve for injecting polymer samples into the mobile phase,
    a first reservoir for containing a first mobile phase fluid, the first reservoir being adapted to maintain the first mobile phase fluid at a first temperature,
    a second reservoir for containing a second mobile phase fluid, the second reservoir being adapted to maintain the second mobile phase fluid at a second temperature,
    a mixing zone adaptable for fluid communication with the first reservoir and the second reservoir for mixing of the first and second mobile phases, the mixing zone being further adaptable for fluid communication with the inlet port of the chromatographic column,
    a control system for controlling the temperature of the mobile phase in the mixing zone by varying the relative amounts of the first and second mobile-phase fluids supplied to the mixing zone, and
    a detector in fluid communication with the effluent port of the chromatographic column for detecting a property of at least one of the separated sample components.

2. The liquid chromatography system of claim 1 further comprising a heating element in thermal communication with at least one of the first or second reservoirs for maintaining the temperature of the mobile phase fluid in the reservoir.

3. The liquid chromatography system of claim 1 further comprising a first heating element in thermal communication with the first reservoir for maintaining the temperature of the first mobile phase fluid at the first temperature, and a second heating element in fluid communication with the second reservoir for maintaining the temperature of the second mobile phase fluid at the second temperature.

4. The liquid chromatography system of claim 1 wherein the temperature of at least one of the first or second mobile phase in the first or second reservoir is maintained to be not less than about 75° C.

5. The liquid chromatography system of claim 1 wherein the temperature of at least one of the first or second mobile phase in the first or second reservoir is maintained to be not less than about 100° C.

6. The liquid chromatography system of claim 1 wherein the temperature of at least one of the first or second mobile phase in the first or second reservoir is maintained to be not less than about 125° C.

7. The liquid chromatography system of claim 1 wherein the detector is selected from the group consisting of a refractive-index detector, an ultraviolet-visual detector, a photodiode array detector, a static-light-scattering detector, a dynamic-light-scattering detector, an evaporative-light-scattering detector and a capillary viscometer detector.

8. A method for characterizing a polymer sample, the method comprising
    injecting a polymer sample into a mobile-phase of a liquid chromatography system, the mobile-phase being supplied to a liquid chromatography column from a mixing zone, the mixing zone being in fluid communication with a first reservoir containing a first mobile phase fluid at a first temperature, and with a second reservoir containing a second mobile phase fluid at a second temperature,
    controlling the temperature of the mobile-phase in the mixing zone to vary over time by varying the relative amounts of the first and second mobile-phase fluids supplied to the mixing zone,
    separating one or more sample components of the polymer sample in the chromatography column, and
    detecting a property of at least one of the separated sample components.

9. The method of claim 8 wherein the polymer sample is characterized in the liquid chromatography system of claim 1.

10. The method of claim 8 wherein the polymer sample is selected from the group consisting of polymer solutions, polymer emulsions and polymer dispersions.

11. The method of claim 8 wherein the polymer sample is a non-biological polymer sample.

12. The method of claim 8 wherein the polymer sample comprises a copolymer.

13. A method for analyzing a plurality of non-biological polymer samples, the method comprising providing a library comprising four or more spatially separated non-biological polymer samples, and serially characterizing each of the four or more polymer samples according to the methods of claim 8.

14. The method of claim 13 wherein the library comprises four or more polymerization product mixtures in reaction vessels, the samples are withdrawn from the reaction vessels into an injection probe for delivery to the liquid chromatography system.

15. The method of claim 8 wherein the detected property is selected from the group consisting of emitted light, refracted light, absorbed light and scattered light.

16. The method of claim 8 further comprising determining a property of interest from the detected property.

17. The method of claim 16 wherein the determined property is selected from the group consisting of weight-average molecular weight, number-average molecular weight, viscosity-average molecular weight, peak molecular weight, polydispersity index and molecular-weight-distribution shape.

18. The method of claim 16 wherein the determined property is selected from the group consisting of composition and conversion.

19. The method of claim 16 wherein the determined property is particle size.

20. The method of claim 8 wherein the property is detected with a detector selected from the group consisting of a refractive-index detector, an ultraviolet-visual detector, a photodiode array detector, a static-light-scattering detector, a dynamic-light-scattering detector, an evaporative-light-scattering detector and a capillary viscometer detector.

21. The method of claim 13 wherein the chromatographic column comprises a stationary-phase and the polymer samples are separated by introducing the samples onto the stationary phase and subsequently eluting the samples or components thereof with the mobile-phase eluant, the method further comprising controlling the column geometry, stationary-phase, eluant composition, eluant temperature or eluant flow rate such that the sample-throughput is not more than about 10 minutes per sample.

22. A liquid chromatography system for characterizing a polymer sample, the system comprising an enclosure defining a heated environment, the heated environment being maintained at a temperature of not less than about 75° C., a chromatographic column residing in the heated environment, the chromatographic column comprising a surface defining a pressurizable separation cavity, an inlet port for receiving a mobile phase and for supplying a polymer sample to the separation cavity, an effluent port for discharging the mobile phase and the polymer sample or separated components thereof from the separation cavity, and a stationary-phase within the separation cavity, an injection port adaptable for fluid communication with the chromatographic column for injecting polymer samples into the mobile phase, a first reservoir for containing a first mobile phase fluid, a second reservoir for containing a second mobile phase fluid, a mixing zone adaptable for fluid communication with the first reservoir and the second reservoir for mixing of the first and second mobile phases to form a mobile-phase eluant having compositions or temperatures that can vary over time, the mixing zone being further adaptable for fluid communication with the inlet port of the chromatographic column for eluting one or more sample components of the sample with the mobile-phase eluant to separate at least one sample component of the sample from other sample components thereof, and a detector in fluid communication with the effluent port of the chromatographic column for detecting a property of at least one of the sample components.

23. The system of claim 22 further comprising a third reservoir for containing a third mobile-phase fluid, the third reservoir being adaptable for fluid communication with the mixing zone for mixing of the third mobile-phase fluid with one or both of the first or second mobile-phase fluids.

24. The system of claim 22 wherein the mixing zone is directly upstream of the column inlet port.

25. The system of claim 22 wherein the column comprises two inlet ports and the mixing zone is within the column.

* * * * *